US012590086B2

(12) United States Patent
Hasui et al.

(10) Patent No.: US 12,590,086 B2
(45) Date of Patent: Mar. 31, 2026

(54) 3-((1H-PYRAZOL-4-YL)METHYL)-6'-(PHENYL)-2H-(1,2'-BIPYRIDIN)-2-ONE DERIVATIVES AND RELATED COMPOUNDS AS GPR139 ANTAGONISTS FOR USE IN A METHOD OF TREATMENT OF E.G. DEPRESSION

(71) Applicant: TAKEDA PHARMACEUTICAL COMPANY LIMITED, Osaka (JP)

(72) Inventors: Tomoaki Hasui, Fujisawa (JP); Satoshi Mikami, Fujisawa (JP); Toru Yamashita, Fujisawa (JP); Shinji Nakamura, Fujisawa (JP); Shinji Morimoto, Fujisawa (JP); Toshihiro Imaeda, Fujisawa (JP); Kazuaki Takami, Fujisawa (JP); Masaki Daini, Fujisawa (JP); Hiroyuki Kakei, Fujisawa (JP); Minoru Nakamura, Fujisawa (JP); Fumie Yamaguchi, Fujisawa (JP); Chunxiang Wang, Fujisawa (JP); Sachie Takashima, Fujisawa (JP); Makoto Kamata, Fujisawa (JP); Yuya Oguro, Fujisawa (JP); Shuhei Ikeda, Fujisawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 618 days.

(21) Appl. No.: 17/999,514

(22) PCT Filed: May 20, 2021

(86) PCT No.: PCT/IB2021/000337

§ 371 (c)(1),
(2) Date: Nov. 21, 2022

(87) PCT Pub. No.: WO2021/234451

PCT Pub. Date: Nov. 25, 2021

(65) Prior Publication Data

US 2023/0357220 A1 Nov. 9, 2023

(30) Foreign Application Priority Data

May 22, 2020 (JP) ................................ 2020-090111

(51) Int. Cl.
*C07D 413/14* (2006.01)
*C07D 401/14* (2006.01)
*C07D 405/14* (2006.01)

(52) U.S. Cl.
CPC ......... *C07D 413/14* (2013.01); *C07D 401/14* (2013.01); *C07D 405/14* (2013.01)

(58) Field of Classification Search
CPC ... C07D 413/14; C07D 401/14; C07D 405/14
See application file for complete search history.

(56) References Cited

FOREIGN PATENT DOCUMENTS

| | | | |
|---|---|---|---|
| WO | 03/068230 | A1 | 8/2003 |
| WO | WO 2008/089005 | A1 | 7/2008 |
| WO | WO 2008/094556 | A3 | 8/2008 |
| WO | WO 2020/097609 | A1 | 5/2020 |
| WO | WO 2021/234450 | | 11/2021 |
| WO | WO 2021/234451 | A1 | 11/2021 |

OTHER PUBLICATIONS

Patel et al. In vitro antimicrobial and antitubercular studies of novel 6-substituted (pyrrolidin-1-yl)-2(1H)-pyridinones, Medical Chemistry Research vol. 21, Dec. 2011, pp. 4108-4119 (Year: 2011).*
Carlson et al., "Neural Correlates of Rapid Antidepressant Response to Ketamine in Treatment-Resistant Unipolar Depression: A Preliminary Positron Emission Tomography Study," Biol Psychiatry 2013 73(12):1213-1221.
Castellani et al., "Copy Number Variation Distribution in Six Monozygotic Twin Pairs Discordant for Schizophrenia," Twin Research and Human Genetics Apr. 2014; 17(2):108-120.
Chabchoub, F. et al., "New Method for the Synthesis of Hydrazonates. Reaction of Primary Amines With N-1-Ethoycarbonyl Hydrazonates: Synthesis of 1,2,4-Triazol-5-Ones," Journal De La Societe Chimique De Tunisie, vol. 4, No. 3, 1998, pp. 171-178.
Ebejer et al., "Genome-Wide Association Study of Inattention and Hyperactivity-Impulsivity Measured as Quantitative Traits," Twin Research and Human Genetics, 2013; 16(2):560-574.
Hu et al., "Identification of Surrogate Agonists and Antagonists for Orphan G-Protein-Coupled Receptor GPR139," Journal of Biomolecular Screening 2009 14:789-797.

(Continued)

*Primary Examiner* — Sarah Pihonak
*Assistant Examiner* — Mikhail O'Donnel Robinson
(74) *Attorney, Agent, or Firm* — Finnegan, Henderson, Farabow, Garrett & Dunner LLP

(57) ABSTRACT

The present invention refers to compounds of formula (I). The present invention also relates to compounds of formula (I) for use as G Protein coupled Receptor 139 (GPR139) antagonists in methods of medical treatment of e.g. depression, Alzheimer's disease, schizophrenia, drug addiction, sleep disorders, pain, and attention deficit hyperactivity disorder. Exemplary compounds are e.g. 3-((1H-pyrazol-4-yl)methyl)-6'-(phenyl)-2H-(1,2'-bipyridin)-2-one derivatives and related compounds. The present description discloses the synthesis and characterisation of exemplary compounds, pharmacological data thereof, as well as exemplary tablet formulations comprising the compounds of the invention (e.g. page 83 to page 110; examples 1 to 33; reference example 1; test examples 1 and 2; tables 1 to 4).

(I)

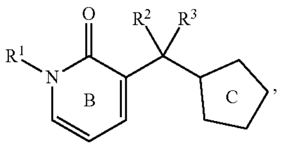

27 Claims, No Drawings

(56) References Cited

OTHER PUBLICATIONS

Kattimani, Pramod P. et al., "$C_5$-Alkyl-1,3,4-Oxadiazol-2-ones Undergo Dealkylation upon Nitrogen Insertion to Form 2H-1,2,4-Triazol-3-ones: Synthesis of 1,2,4-Triazol-3-one Hybrids with Triazolothiadiazoles and Triazolothiadiazines," Journal of Heterocyclic Chemistry, vol. 54, No. 4, Feb. 27, 2017, pp. 2258-2265.
Liu C et al., "GPR139, an Orphan Receptor Highly Enriched in the Habenula and Septum, Is Activated by the Essential Amino Acids L-Tryptophan and L-Phenylalanine," Mol Pharmacol. 2015 88(5):911-25.
Matsuo et al., "Molecular cloning and characterization of a novel Gq-coupled orphan receptor GPRg1 exclusively expressed in the central nervous system," Biochemical and Biophysical Research Communications 331 (2005) 363-369.
Nesaragi, Aravind R. et al., "Microwave assisted regioselective synthesis of quinoline appended triazoles as potent anti-tubercular and antifungal agents via copper (I) catalyzed cycloaddition," Bioorganic & Medicinal Chemistry Letters, vol. 41, 2021 (ten pages).
O'Roak et al., "Exome sequencing in sporadic autism spectrum disorders identifies severe de novo mutations," Nature Genetics, 2011; 43(6):585-589.
Patel and Sharma, "New Synthetic Approaches to Substituted Pyridine-2-(1H)-Ones Clubbed with Substituted Aryl Diazo Substituents," Synthetic Communications, 43, 1250-1262, 2013.
Sartorius et al., "Remission of Major Depression Under Deep Brain Stimulation of the Lateral Habenula in a Therapy-Refractory Patient," Biol Psychiatry 2010 67: e9-e11.
Somagond, Shilpa M. et al., "Click chemistry based on regioselective one-pot synthesis of coumarin-3-yl-methyl-1,2,3-triazolyl-1,2,4-triazol-3(4H)-ones as newer potent antitubercular agents," Arch Pharm Chem Life Sci, vol. 352, 2019, <https://doi.org/10.1002/ardp.201900013> (13 pages).
Somagond, Shilpa M. et al., "Microwave-Assisted Synthesis of Novel Symmetric Bis-1,2,4-triazolin-3-ones as Potent Inhibitors of CYP51: An Antifungal Activity Study", ChemistrySelect, vol. 3, No. 29, pp. 8529-8538, 2018.
Yang et al., "Ketamine blocks bursting in the lateral habenula to rapidly relieve depression," Nature 2018 554(7692):317-322.
U.S. Appl. No. 17/999,505, filed Nov. 21, 2022.
CAplus Registry No. RN 1174845-16-9.

* cited by examiner

3-((1H-PYRAZOL-4-YL)METHYL)-6'-(PHENYL)-2H-(1,2'-BIPYRIDIN)-2-ONE DERIVATIVES AND RELATED COMPOUNDS AS GPR139 ANTAGONISTS FOR USE IN A METHOD OF TREATMENT OF E.G. DEPRESSION

This application is a national stage filing under 35 U.S.C. § 371 of International Application No. PCT/IB2021/000337, filed May 20, 2021, which claims the benefit of priority of Japanese Patent Application No. 2020-090111, filed May 22, 2020, the contents of each of which are incorporated by reference herein in their entirety.

The present disclosure relates to heterocyclic compounds which exhibit G protein-coupled receptor (GPR) 139 receptor antagonist action and are expected to be useful in the treatment or preventing of GPR139-mediated diseases such as depression, Alzheimer's disease, schizophrenia, drug addiction, sleep disorders, pain, and attention deficit hyperactivity disorder.

GPR139 is an orphan G-protein coupled receptor that is coupled with Gs and Gq proteins (Journal of Biomolecular Screen 2009 14:789-797; Biochemical and Biophysical Research Communications 331 (2005) 363-369). The protein sequence of GPR139 is highly conserved among different species. For example, human, mouse, and rat GPR139 protein sequences share more than 94% identity at the amino acid level. Additionally, expression of GPR139 is high in the central nervous system, in particular in the striatum, septal area, hypothalamus, and habenular nucleus, and is low in peripheral tissue. The high degree of sequence homology and predominant expression in the brain across different species suggests that GPR139 plays an important role in physiology.

Variations of the GPR139 gene have been reported in psychiatric disorders such as schizophrenia, autism spectrum disorder, or attention deficit hyperactivity disorder (Twin Research and Human Genetics 2014 April; 17(2):108-120; Nature Genetics 2011 June; 43(6):585-589; Twin Research and Human Genetics 2013 April; 16(2):560-574). In addition, the habenular nucleus, which is one of the regions of the brain where GPR139 is highly expressed, is known to regulate stress response and learning; the habenular nuclei of patients with depression are thought to be hyperactive. In cases of patients who also exhibit refractory psychiatric symptoms, the HAMD21 score for evaluating depression symptoms has been reported to improve upon strong stimulation of the habenular nucleus using deep brain stimulation (DBS) (Biol Psychiatry 2010 67:e9-e11). Furthermore, when the regions of the brain where neural activity changes after ketamine administration were investigated by positron emission tomography (PET) in 20 patients with refractory depression, glucose metabolism, which reflects neural activity in regions of the brain such as the habenular nucleus, was suppressed, and depression symptoms improved (Biol Psychiatry 2013 73(12:1213-1221)). In animal tests, the neural activity of the habenular nucleus was suppressed by directly administering ketamine into the habenular nucleus, and an improvement in anhedonia-like behavior was observed (Nature 2018 554(7692): 317-322). Together, these results suggest that GPR139 activity affects the neural activity of the habenular nucleus and may dramatically alter central nervous function or neuropsychiatric state.

Antagonists (including inverse agonists) of the GPR139 receptor may be useful for treating CNS disorders such as depression, Alzheimer's disease, schizophrenia, drug addiction, sleep disorders, pain, and attention deficit hyperactivity disorder. Accordingly, there is a need for novel compounds exhibiting GPR139 receptor antagonist (including inverse agonist) action.

Certain heterocyclic compounds may be useful as antagonists of the GPR139 receptor. A method of synthesizing one class of heterocyclic compounds, derivatives of 6-(4H-1,2,4-triazol-4-yl)-2(1H)-pyridinones, has been previously described (Synthetic Communication 43:9, 1250-1262, 2013).

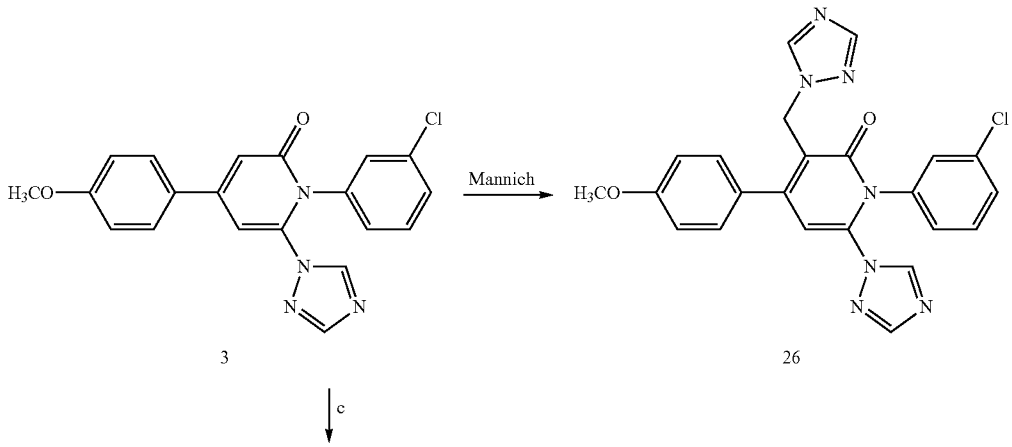

3 26

-continued

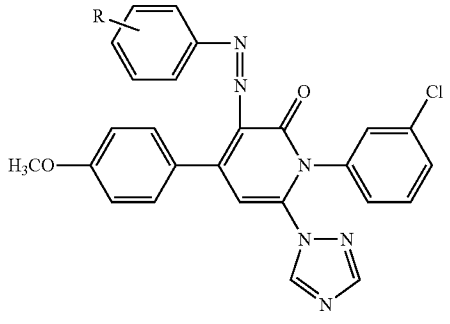

4-14

+

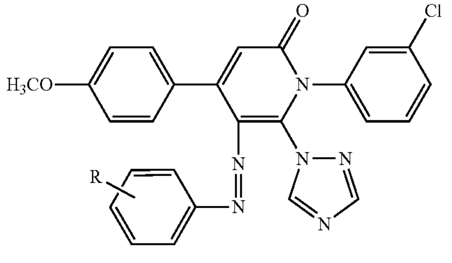

15-25

Disclosed herein are compounds exhibiting GPR139 receptor antagonist action, which may be useful in the treatment or prevention of depression, Alzheimer's disease, schizophrenia, drug addiction, sleep disorders, pain, attention deficit hyperactivity disorder, and the like.

Disclosed herein is a compound (also called Compound (I) hereinafter) of Formula (I)

(I)

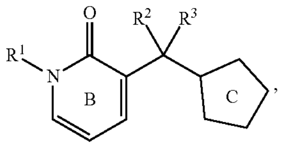

or a pharmaceutically acceptable salt thereof, wherein:

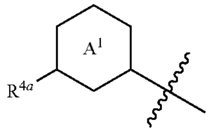

or

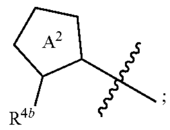

;

ring $A^1$ is chosen from optionally further substituted 6-membered aromatic rings;

ring $A^2$ is chosen from optionally further substituted 5-membered monocyclic aromatic heterocyclic rings;

ring B is chosen from pyridone rings optionally further substituted with 1 to 3 substituents chosen from halogen atoms and optionally substituted $C_{1-6}$ groups;

$R^2$ and $R^3$ are each independently chosen from hydrogen atom and substituents;

$R^{4a}$ and $R^{4b}$ are each independently chosen from substituents; and ring C is chosen from optionally further substituted 5-membered monocyclic aromatic heterocyclic rings.

In some embodiments, $R^1$ is

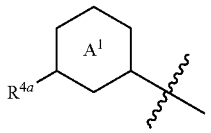

In some embodiments, $R^1$ is

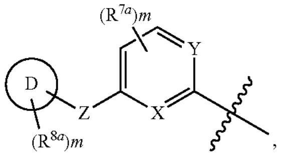

wherein:

X is CH or N;

Y is CH or N;

Z is chosen from a bond, —O—, —$OR^{9a}$—*, —NH—, and —$N(R^{9b})R^{9a}$—*, wherein * denotes the connection point to ring D;

ring D is chosen from 6- to 8-membered aromatic rings, 5- to 8-membered monocyclic aromatic heterocyclic rings, $C_{3-8}$ cycloalkyl groups, and 5- to 8-membered heterocyclic groups;

each $R^{7a}$ is independently chosen from cyano, halogen, $C_{3-6}$ cycloalkyl, $C_{1-6}$ alkyl, and $C_{1-6}$ alkoxy groups, wherein the $C_{3-6}$ cycloalkyl, $C_{1-6}$ alkyl, and $C_{1-6}$ alkoxy groups are optionally substituted with 1 to 4 halogen atoms;

each $R^{8a}$ is independently chosen from halogen, $C_{1-6}$ alkyl, and $C_{1-6}$ alkoxy groups, wherein the $C_{1-6}$ alkyl and $C_{1-6}$ alkoxy groups are optionally substituted with 1 to 4 halogen atoms;

$R^{9a}$ is chosen from $C_{1-3}$ alkyl groups;

$R^{9b}$ is chosen from hydrogen atom and $C_{1-3}$ alkyl groups;

m is 0, 1, 2, or 3; and n is 0, 1, 2, or 3.

In some embodiments, Z is chosen from a bond, —O—, —NH—, —$NHCH_2$—*, and —$N(CH_3)CH_2$—*, and all other variables are as defined above.

In some embodiments, Z is a bond, and all other variables are as defined above. In some embodiments, Z is —O—, and all other variables are as defined above. In some embodiments, Z is —NH—, and all other variables are as defined above. In some embodiments, Z is —$NHCH_2$—*, and all other variables are as defined above. In some embodiments, Z is —$N(CH_3)CH_2$—*, and all other variables are as defined above.

In some embodiments, X is N, Y is CH, and all other variables are as defined above.

In some embodiments, X is N, Y is N, and all other variables are as defined above.

In some embodiments, X is CH, Y is CH, and all other variables are as defined above.

In some embodiments, ring D is chosen from benzene, morpholine, oxane, piperidine, and cyclobutane, and all other variables are as defined above.

In some embodiments, ring D is benzene and all other variables are as defined above. In some embodiments, ring D is morpholine and all other variables are as defined above. In some embodiments, ring D is oxane and all other variables are as defined above. In some embodiments, ring D is piperidine and all other variables are as defined above. In some embodiments, ring D is cyclobutane and all other variables are as defined above.

In some embodiments, $R^1$ is

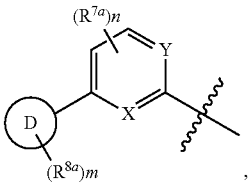
, wherein X, Y, ring D, $R^{7a}$, $R^{8a}$, m, and n are as defined above.

In some embodiments, X is N, Y is CH, and all other variables are as defined above.

In some embodiments, X is N, Y is N, and all other variables are as defined above.

In some embodiments, X is CH, Y is CH, and all other variables are as defined above.

In some embodiments, ring D is chosen from benzene, morpholine, oxane, piperidine, and cyclobutane, and all other variables are as defined above.

In some embodiments, ring D is benzene and all other variables are as defined above. In some embodiments, ring D is morpholine and all other variables are as defined above. In some embodiments, ring D is oxane and all other variables are as defined above. In some embodiments, ring D is piperidine and all other variables are as defined above. In some embodiments, ring D is cyclobutane and all other variables are as defined above.

In some embodiments, $R^1$ is

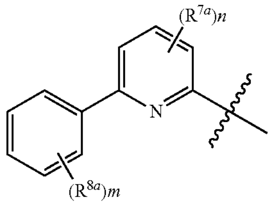
, wherein $R^{7a}$, $R^{8a}$, m, and n are as defined above.

In some embodiments, $R^1$ is

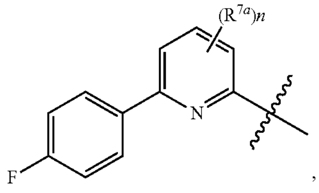
, wherein $R^{7a}$ and n are as defined above.

In some embodiments, $R^1$ is

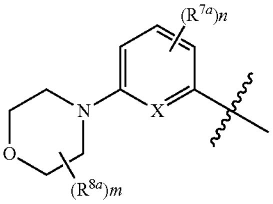
, wherein X, $R^{7a}$, $R^{8a}$, and n are as defined above. In some embodiments, X is CH. In some embodiments, X is N.

In some embodiments, $R^1$ is

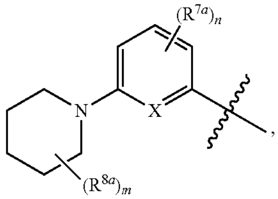
, wherein X, $R^{7a}$, $R^{8a}$, m, and n are as defined above. In some embodiments, X is CH.

In some embodiments, $R^1$ is

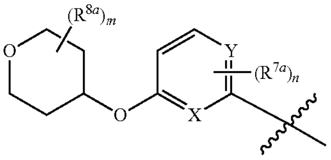
, wherein X, Y, $R^{7a}$, $R^{8a}$, m, and n are as defined above. In some embodiments, X is N and Y is CH.

In some embodiments, $R^1$ is

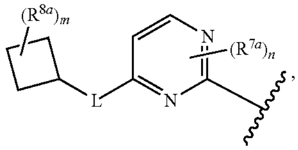
, wherein Z, $R^{7a}$, $R^{8a}$, m, and n are as defined above. In some embodiments, Z is —$NHCH_2$—*. In some embodiments, Z is —$N(CH_3)CH_2$—*.

In some embodiments, $R^1$ is

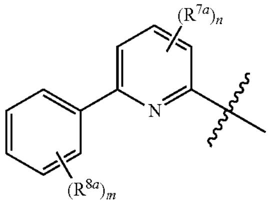
, wherein:

each $R^7$, is independently chosen from cyano, halogen, $C_{3-6}$ cycloalkyl, $C_{1-6}$ alkyl, and $C_{1-6}$ alkoxy groups, wherein the $C_{3-6}$ cycloalkyl, $C_{1-6}$ alkyl, and $C_{1-6}$ alkoxy groups are optionally substituted with 1 to 4 halogen atoms;

each $R^{8a}$ is independently chosen from halogen atoms, $C_{1-6}$ alkyl, and $C_{1-6}$ alkoxy groups, wherein the $C_{1-6}$ alkyl and $C_{1-6}$ alkoxy groups are optionally substituted with 1 to 4 halogen atoms;

m is 0, 1, 2, or 3; and n is 0, 1, 2, or 3.

In some embodiments, each $R^{7a}$ is independently chosen from cyano, halogen, $C_{1-6}$ alkyl, and $C_{1-6}$ alkoxy groups, wherein the $C_{1-6}$ alkyl and $C_{1-6}$ alkoxy groups are optionally substituted with 1 to 4 halogen atoms; each $R^{8a}$ is independently chosen from halogen atoms and $C_{1-6}$ alkyl groups, wherein the $C_{1-6}$ alkyl groups are optionally substituted with 1 to 4 halogen atoms; m is 0, 1, 2, or 3; and n is 0, 1, 2, or 3.

In some embodiments, $R^1$ is

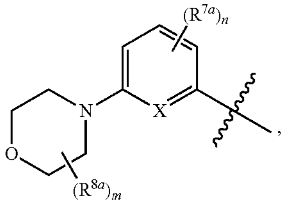

herein:

X is CH or N;

Y is CH or N;

each $R^{7a}$ is independently chosen from halogen, $C_{3-6}$ cycloalkyl, $C_{1-6}$ alkyl, and $C_{1-6}$ alkoxy groups, wherein the $C_{3-6}$ cycloalkyl, $C_{1-6}$ alkyl, and $C_{1-6}$ alkoxy groups are optionally substituted with 1 to 4 halogen atoms;

each $R^{8a}$ is independently chosen from halogen atoms, $C_{1-6}$ alkyl, and $C_{1-6}$ alkoxy groups, wherein the $C_{1-6}$ alkyl and $C_{1-6}$ alkoxy groups are optionally substituted with 1 to 4 halogen atoms;

m is 0, 1, 2, or 3; and n is 0, 1, 2, or 3.

In some embodiments, $R^1$ is

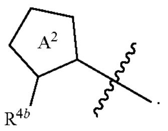

In some embodiments, ring B is

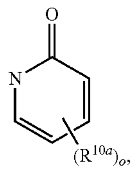

wherein:

each $R^{10a}$ is independently chosen from halogen atoms and $C_{1-3}$ alkyl groups; and o is 0, 1, or 2.

In some embodiments, o is 0.

In some embodiments, o is 1, and $R^{10a}$ is a fluorine atom or methyl.

In some embodiments, o is 2, and each $R^{10a}$ is independently chosen from a fluorine atom and methyl.

In some embodiments, $R^2$ and $R^3$ are each independently chosen from hydrogen and $C_{1-3}$ alkyl groups. In some embodiments, $R^2$ and $R^3$ are both hydrogen atoms.

In some embodiments, ring C is

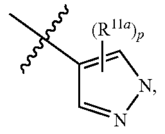

wherein each $R^{11a}$ is independently chosen from $C_{1-3}$ alkyl groups and p is 0, 1, or 2.

In some embodiments, ring C is

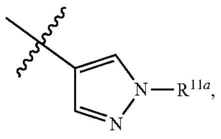

herein $R^{11a}$ is chosen from $C_{1-3}$ alkyl groups. In some embodiments, $R^{11a}$ is ethyl.

In some embodiments, the compounds of Formula (I) and pharmaceutically acceptable salts thereof are provided for use in the treatment or preventing of a disease chosen from depression, Alzheimer's disease, schizophrenia, drug addiction, sleep disorders, pain, and attention deficit hyperactivity disorder. In some embodiments, a compound chosen from Examples 1-33, or a pharmaceutically acceptable salt thereof, is provided for use in the treatment or preventing of a disease chosen from depression, Alzheimer's disease, schizophrenia, drug addiction, sleep disorders, pain, and attention deficit hyperactivity disorder.

Also disclosed herein is a pharmaceutical composition comprising at least one compound of Formula (I) or a pharmaceutically acceptable salt thereof. In some embodiments, the pharmaceutical composition comprises: at least one compound of Formula (I) or a pharmaceutically acceptable salt thereof; and at least one pharmaceutically acceptable carrier.

Also disclosed herein is a compound of Formula (I) or a pharmaceutically acceptable salt thereof for use in therapy. In some embodiments, there is provided a compound chosen from Examples 1-33, or a pharmaceutically acceptable salt thereof, for use in therapy.

In some embodiments, a compound of Formula (I) or a pharmaceutically acceptable salt thereof is combined with at least one combination drug for simultaneous, separate, or sequential use in the treatment or preventing of a disease chosen from depression, Alzheimer's disease, schizophrenia, drug addiction, sleep disorders, pain, and attention deficit hyperactivity disorder. In some embodiments, when the use is simultaneous, the compound and the at least one combination drug are in separate pharmaceutical compositions. In some embodiments, when the use is simultaneous, the compound and the at least one combination drug are together in the same pharmaceutical composition. In some embodiments, the compound is chosen from Examples 1-33 and pharmaceutically acceptable salts thereof.

In some embodiments, a combination of a compound of Formula (I) or a pharmaceutically acceptable salt thereof and a combination drug is provided for use in a method of treating or preventing a disease chosen from depression, Alzheimer's disease, schizophrenia, drug addiction, sleep disorders, pain, and attention deficit hyperactivity disorder. In some embodiments, the compound and the combination drug are prepared for administration in the same pharmaceutical composition. In some embodiments, the compound and the combination drug are prepared for administration in separate pharmaceutical compositions. In some embodiments, the compound and the combination drug are prepared for simultaneous administration. In some embodiments, the compound and the combination drug are prepared for sequential administration. In some embodiments, the compound is chosen from Examples 1-33 and pharmaceutically acceptable salts thereof.

Also disclosed herein is a pharmaceutical composition comprising a compound of Formula (I) or a pharmaceutically acceptable salt thereof for use in therapy. In some embodiments, there is provided a pharmaceutical composition comprising a compound chosen from Examples 1-33, or a pharmaceutically acceptable salt thereof, for use in therapy.

Also disclosed herein is a method of treating or preventing a disease chosen from depression, Alzheimer's disease, schizophrenia, drug addiction, sleep disorders, pain, and attention deficit hyperactivity disorder, the method comprising administering at least one compound of Formula (I) or a pharmaceutically acceptable salt thereof.

It should be understood that references herein to methods of treatment or preventing (e.g., methods of treating or preventing a disease chosen from depression, Alzheimer's disease, schizophrenia, drug addiction, sleep disorders, pain, and attention deficit hyperactivity disorder) using one or more compounds (e.g., compounds of Formula (I) and pharmaceutically acceptable salts thereof) should be interpreted as references to:

- one or more compounds for use in methods of treating and/or preventing, for example, depression, Alzheimer's disease, schizophrenia, drug addiction, sleep disorders, pain, or attention deficit hyperactivity disorder; and/or
- the use of one or more compounds in the manufacture of a medicament for treating and/or preventing, for example, depression, Alzheimer's disease, schizophrenia, drug addiction, sleep disorders, pain, or attention deficit hyperactivity disorder.

Non-Limiting Example Embodiments 1

Without limitation, some embodiments of the disclosure include:

1. A compound represented by Formula (I):

(I)

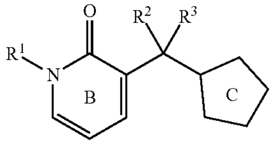, or a salt thereof, wherein:

$R^1$ is a group represented by

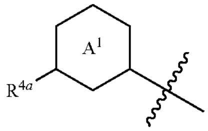 or 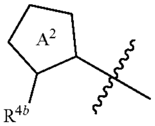;

ring $A^1$ is an optionally further substituted 6-membered aromatic ring;

ring $A^2$ is an optionally further substituted 5-membered monocyclic aromatic heterocyclic ring;

ring B is a pyridone ring optionally further substituted with 1 to 3 substituents chosen from:

(1) halogen atoms; and (2) optionally substituted $C_{1-6}$ groups;

$R^2$ and $R^3$ are each independently a hydrogen atom or a substituent;

$R^{4a}$ and $R^{6b}$ are each independently a substituent; and ring C is an optionally further substituted 5-membered monocyclic aromatic heterocyclic ring).

2. A pharmaceutical comprising the compound or salt according to Embodiment 1.
3. The pharmaceutical according to Embodiment 2, which is a GPR139 receptor antagonist.
4. The pharmaceutical according to Embodiment 2, which is a GPR139 receptor inverse agonist.
5. The pharmaceutical according to Embodiment 2, which is a drug for preventing or treating depression, Alzheimer's disease, schizophrenia, drug addiction, sleep disorders, pain, or attention deficit hyperactivity disorder.

Non-Limiting Example Embodiments 2

Without limitation, some embodiments/clauses of the disclosure include:

1. A compound of Formula (I)

(I)

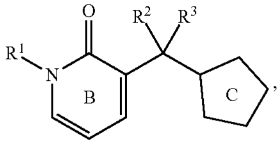, or a pharmaceutically acceptable salt thereof, wherein:

$R^1$ is

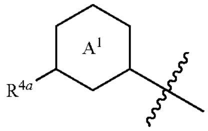 or 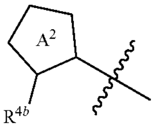;

ring $A^1$ is chosen from optionally further substituted 6-membered aromatic rings;

ring $A^2$ is chosen from optionally further substituted 5-membered monocyclic aromatic heterocyclic rings;

ring B is chosen from pyridone rings optionally further substituted with 1 to 3 substituents chosen from halogen atoms and optionally substituted $C_{1-6}$ groups;

$R^2$ and $R^3$ are each independently chosen from hydrogen atom and substituents;

$R^{4a}$ and $R^{4b}$ are each independently chosen from substituents; and ring C is chosen from optionally further substituted 5-membered monocyclic aromatic heterocyclic rings.

2. The compound or pharmaceutically acceptable salt according to Clause 1, wherein the compound is chosen from compounds of Formula (I')

(I')

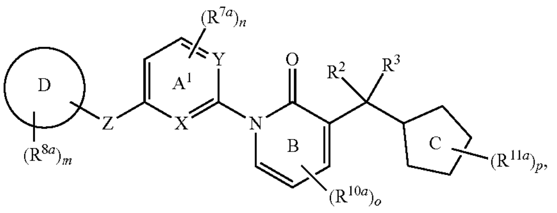

and pharmaceutically acceptable salts thereof, wherein:

X is CH or N;

Y is CH or N;

Z is chosen from a bond, —O—, —$OR^{9a}$—*, —NH—, and —$N(R^{9b})R^{9a}$—*, wherein * denotes the connection point to ring D;

ring C is chosen from 5-membered monocyclic aromatic heterocyclic rings;

ring D is chosen from 6- to 8-membered aromatic rings, 5- to 8-membered monocyclic aromatic heterocyclic rings, $C_{3-8}$ cycloalkyl groups, and 5- to 8-membered heterocyclic groups;

each $R^{7a}$ is independently chosen from cyano, halogen, $C_{3-6}$, cycloalkyl, $C_{1-6}$ alkyl, and $C_{1-6}$ alkoxy groups, wherein the $C_{3-6}$ cycloalkyl, $C_{1-6}$ alkyl, and $C_{1-6}$ alkoxy groups are optionally substituted with 1 to 4 halogen atoms;

each $R^{8a}$ is independently chosen from halogen, $C_{1-6}$ alkyl, and $C_{1-6}$ alkoxy groups, wherein the $C_{1-6}$ alkyl and $C_{1-6}$ alkoxy groups are optionally substituted with 1 to 4 halogen atoms;

$R^{9a}$ is chosen from $C_{1-3}$ alkyl groups;

$R^{9b}$ is chosen from hydrogen atom and $C_{1-3}$ alkyl groups;

each $R^{10a}$ is independently chosen from halogen atoms and $C_{1-3}$ alkyl groups;

each $R^{11a}$ is independently chosen from $C_{1-3}$ alkyl groups;

m is 0, 1, 2, or 3, n is 0, 1, 2, or 3;

o is 0, 1, or 2; and p is 0, 1, or 2.

3. The compound or pharmaceutically acceptable salt according to Clause 2, wherein:

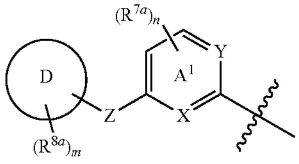

is

-continued

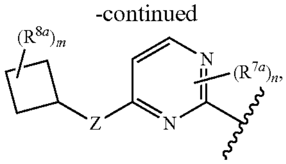

wherein Z, $R^{7a}$, $R^{8a}$, m, and n are as defined in Clause 2.

4. The compound or pharmaceutically acceptable salt according to Clause 2 or 3, wherein Z is chosen from a bond, —O—, —NH—, —$NHCH_2$—*, and —$N(CH_3)CH_2$—*.

5. The compound or pharmaceutically acceptable salt according to any one of Clauses 2-4, wherein Z is a bond.

6. The compound or pharmaceutically acceptable salt according to any one of Clauses 2-4, wherein Z is —O—.

7. The compound or pharmaceutically acceptable salt according to any one of Clauses 2-4, wherein Z is —$NHCH_2$—*.

8. The compound or pharmaceutically acceptable salt according to any one of Clauses 2-4, wherein Z is —$N(CH_3)CH_2$—*.

9. The compound or pharmaceutically acceptable salt according to Clause 2, wherein:

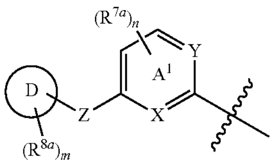

is

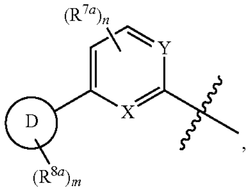

, wherein X, Y, ring D, $R^{7a}$, $R^{8a}$, m, and n are as defined in Clause 2.

10. The compound or pharmaceutically acceptable salt according to any one of Clauses 2-9, wherein ring D is chosen from benzene, morpholine, oxane, piperidine, and cyclobutane.

11. The compound or pharmaceutically acceptable salt according to Clause 2, wherein

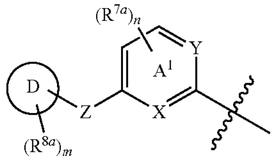

is

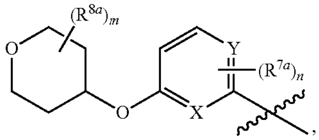

wherein X, Y, $R^{7a}$, $R^{8a}$, m, and n are as defined in Clause 2.

12. The compound or pharmaceutically acceptable salt according to any one of Clauses 2-11, wherein X is CH.

13. The compound or pharmaceutically acceptable salt according to any one of Clauses 2-11, wherein X is N.

14. The compound or pharmaceutically acceptable salt according to any one of Clauses 2-13, wherein Y is CH.

15. The compound or pharmaceutically acceptable salt according to any one of Clauses 2-13, wherein Y is N.

16. The compound or pharmaceutically acceptable salt according to Clause 2, wherein

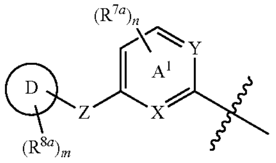

is

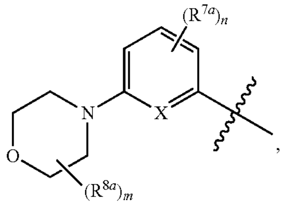

, wherein X, $R^{7a}$, $R^{8a}$, m, and n are as defined in Clause 2.

17. The compound or pharmaceutically acceptable salt according to Clause 2, wherein

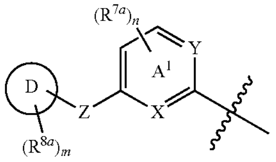

is

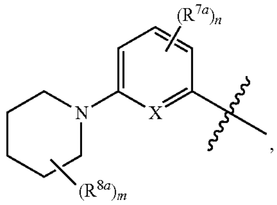

, wherein X, $R^{7a}$, $R^{8a}$, m, and n are as defined in Clause 2.

18. The compound or pharmaceutically acceptable salt according to Clause 16 or 17, wherein X is CH.

19. The compound or pharmaceutically acceptable salt according to Clause 16 or 17, wherein X is N.

20. The compound or pharmaceutically acceptable salt according to any one of Clauses 2-12, wherein $R^2$ and $R^3$ are both hydrogen atoms.

21. The compound or pharmaceutically acceptable salt according to any one of Clauses 2-20, wherein ring C is

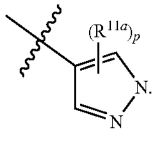

22. The compound or pharmaceutically acceptable salt according to any one of Clauses 2-21, wherein ring C is

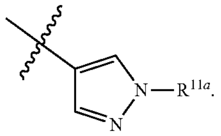

23. The compound or pharmaceutically acceptable salt according to any one of Clauses 2-22, wherein each $R^{7a}$ is independently chosen from halogen, $C_{3-6}$ cycloalkyl, $C_{1-6}$ alkyl, and $C_{1-6}$ alkoxy groups, wherein the $C_{3-6}$ cycloalkyl, $C_{1-6}$ alkyl, and $C_{1-6}$ alkoxy groups are optionally substituted with 1 to 4 halogen atoms.

24. The compound or pharmaceutically acceptable salt according to any one of Clauses 2-23, wherein o is 1 and $R^{10a}$ is methyl.

25. The compound or pharmaceutically acceptable salt according to any one of Clauses 2-23, wherein o is 1 and $R^{10a}$ is a fluorine atom.

26. The compound or pharmaceutically acceptable salt according to any one of Clauses 2-23, wherein o is 0.

27. A compound chosen from:

3-[(1-ethyl-1H-pyrazol-4-yl)methyl]-6'-(4-fluorophenyl)-4'-(trifluoromethyl)-2H-[1,2'-bipyridin]-2-one;

3-[(1-ethyl-1H-pyrazol-4-yl)methyl]-6'-(4-fluorophenyl)-2-oxo-4'-(trifluoromethyl)-2H-[1,2'-bipyridine]-3'-carbonitrile;

3-[(1-ethyl-1H-pyrazol-4-yl)methyl]-6'-(4-fluorophenyl)-2-oxo-4'-(2,2,2-trifluoroethoxy)-2H-[1,2'-bipyridine]-3'-carbonitrile;

4'-(2,2-difluoroethoxy)-3-[(1-ethyl-1H-pyrazol-4-yl)methyl]-6'-(4-fluorophenyl)-2-oxo-2H-[1,2'-bipyridine]-3'-carbonitrile;

3-[(1-ethyl-1H-pyrazol-4-yl)methyl]-6'-(4-fluorophenyl)-6-methyl-2-oxo-4'-(trifluoromethyl)-2H-[1,2'-bipyridine]-3'-carbonitrile;

4'-(difluoromethyl)-3-[(1-ethyl-1H-pyrazol-4-yl)methyl]-6'-(4-fluorophenyl)-2-oxo-2H-[1,2'-bipyridine]-3'-carbonitrile;

3-[(1-ethyl-1H-pyrazol-4-yl)methyl]-3'-fluoro-6'-[(2R)-2-methylmorpholin-4-yl]-4'-(trifluoromethyl)-2H-[1,2'-bipyridin]-2-one;

3-[(1-ethyl-1H-pyrazol-4-yl)methyl]-5'-methyl-6'-[(2R)-2-methylmorpholin-4-yl]-4'-(trifluoromethyl)-2H-[1,2'-bipyridin]-2-one;

3-[(1-ethyl-1H-pyrazol-4-yl)methyl]-1-{2-fluoro-5-[(2R)-2-methylmorpholin-4-yl]-3-(trifluoromethyl)phenyl}pyridin-2(1H)-one;

6'-[2-(difluoromethyl)morpholin-4-yl]-3-[(1-ethyl-1H-pyrazol-4-yl)methyl]-3'-fluoro-4'-(trifluoromethyl)-2H-[1,2'-bipyridin]-2-one;

3-[(1-ethyl-1H-pyrazol-4-yl)methyl]-3'-fluoro-4-methyl-6'-[(2R)-2-methylmorpholin-4-yl]-4'-(trifluoromethyl)-2H-[1,2'-bipyridin]-2-one;

3-[(1-ethyl-1H-pyrazol-4-yl)methyl]-3'-fluoro-5-methyl-6'-[(2R)-2-methylmorpholin-4-yl]-4'-(trifluoromethyl)-2H-[1,2'-bipyridin]-2-one;

3-[(1-ethyl-1H-pyrazol-4-yl)methyl]-3'-fluoro-6'-[(oxan-4-yl)oxy]-4'-(trifluoromethyl)-2H-[1,2'-bipyridin]-2-one;

3-[(1-ethyl-1H-pyrazol-4-yl)methyl]-1-[4-{[(1-fluorocyclobutyl)methyl]amino}-6-(trifluoromethyl)pyrimidin-2-yl]pyridin-2(1H)-one;

1-[4-{[(3,3-difluorocyclobutyl)methyl]amino}-6-(trifluoromethyl)pyrimidin-2-yl]-3-[(1-ethyl-1H-pyrazol-4-yl)methyl]pyridin-2(1H)-one;

1-[4-{[(3,3-difluorocyclobutyl)methyl](methyl)amino}-6-(trifluoromethyl)pyrimidin-2-yl]-3-[(1-ethyl-1H-pyrazol-4-yl)methyl]pyridin-2(1H)-one;
3-[(1-ethyl-1H-pyrazol-4-yl)methyl]-1-[4-{[(1-fluorocyclobutyl)methyl](methyl)amino}-6-(trifluoromethyl)pyrimidin-2-yl]pyridin-2(1H)-one;
1-{3-cyclopropyl-2-fluoro-5-[(2R)-2-methylmorpholin-4-yl]phenyl}-3-[(1-ethyl-1H-pyrazol-4-yl)methyl]pyridin-2(1H)-one;
1-[3-cyclopropyl-5-(2,2-dimethylmorpholin-4-yl)-2-fluorophenyl]-3-[(1-ethyl-1H-pyrazol-4-yl)methyl]pyridin-2(1H)-one;
1-{3-cyclopropyl-2-fluoro-5-[(oxan-4-yl)oxy]phenyl}-3-[(1-ethyl-1H-pyrazol-4-yl)methyl]pyridin-2(1H)-one;
1-{3-bromo-2-fluoro-5-[(oxan-4-yl)oxy]phenyl}-3-[(1-ethyl-1H-pyrazol-4-yl)methyl]pyridin-2(1H)-one;
3-[(1-ethyl-1H-pyrazol-4-yl)methyl]-1-{2-fluoro-5-[(2R)-2-methylmorpholin-4-yl]-3-(trifluoromethoxy)phenyl}pyridin-2(1H)-one;
1-{3-cyclopropyl-2-fluoro-5-[(2R)-2-methylmorpholin-4-yl]phenyl}-3-([1-(propan-2-yl)-1H-pyrazol-4-yl]methylpyridin-2(1H)-one;
1-{3-cyclopropyl-2-fluoro-5-[(2R)-2-methylmorpholin-4-yl]phenyl}-3-[(1-ethyl-1H-pyrazol-4-yl)methyl]-4-fluoropyridin-2(1H)-one;
3-[(1-ethyl-1H-pyrazol-4-yl)methyl]-1-(2-fluoro-5-[(2R)-2-methylmorpholin-4-yl]-3-(propan-2-yl)phenyl pyridin-2(1H)-one;
3-[(1-ethyl-1H-pyrazol-4-yl)methyl]-1-{2-fluoro-5-[(2R)-2-methylmorpholin-4-yl]-3-(2,2,2-trifluoroethyl)phenyl}pyridin-2(1H)-one;
1-(3-cyclopropyl-5-[(2R)-2-methylmorpholin-4-yl]phenyl)-3-[(1-ethyl-1H-pyrazol-4-yl)methyl]-6-methylpyridin-2(1H)-one;
1-[3-(2,2-difluorocyclopropyl)-5-(4,4-difluoropiperidin-1-yl)-2-fluorophenyl]-3-[(1-ethyl-1H-pyrazol-4-yl)methyl]pyridin-2(1H)-one;
1-{3-cyclopropyl-5-[(2R)-2-methylmorpholin-4-yl]phenyl}-3-[(1-ethyl-1H-pyrazol-4-yl)methyl]-6-fluoropyridin-2(1H)-one;
1-{3-cyclopropyl-2-fluoro-5-[(2R)-2-methylmorpholin-4-yl]phenyl}-3-[(1-ethyl-1H-pyrazol-4-yl)methyl]-5-methylpyridin-2(1H)-one; and
1-{3-cyclopropyl-2-fluoro-5-[(2R)-2-methylmorpholin-4-yl]phenyl}-3-[(1-ethyl-1H-pyrazol-4-yl)methyl]-4-methylpyridin-2(1H)-one, or a pharmaceutically acceptable salt of any of the foregoing.

28. A pharmaceutical composition comprising:
at least one compound or pharmaceutically acceptable salt according to any one of Clauses 1-27; and
at least one pharmaceutically acceptable carrier.

29. A method of treating or preventing a disease in a mammal in need thereof, the method comprising administering to the mammal at least one compound or pharmaceutically acceptable salt according to any one of Clauses 1-27.

30. The method according to Clause 29, wherein the disease is chosen from depression, Alzheimer's disease, schizophrenia, drug addiction, sleep disorders, pain, and attention deficit hyperactivity disorder.

31. The method according to Clause 28 or 29, wherein the mammal is a human.

32. The method according to any one of Clauses 29-31, further comprising administering to the mammal at least one combination drug.

The definitions of each of the substituents used in the present specification will be described in detail hereinafter. Unless specified otherwise, each substituent is defined as follows.

Non-limiting examples of "halogen atoms" in the present specification include fluorine, chlorine, bromine, and iodine.

Non-limiting examples of "$C_{1-6}$ alkyl groups" in the present specification include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, and 2-ethylbutyl.

Non-limiting examples of "optionally halogenated $C_{1-6}$, alkyl groups" in the present specification include $C_{1-6}$ alkyl groups which may have from 1 to 7, for example, from 1 to 5, halogen atoms. Further non-limiting examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, and 6,6,6-trifluorohexyl.

Non-limiting examples of "$C_{2-6}$ alkenyl groups" in the present specification include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, and 5-hexenyl.

Non-limiting examples of "$C_{2-6}$ alkynyl groups" in the present specification include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, and 4-methyl-2-pentynyl.

Non-limiting examples of "$C_{3-10}$ cycloalkyl groups" in the present specification include cyclopropyl, cyclobutyl, cyclopentyl, cyclohexyl, cycloheptyl, cyclooctyl, bicyclo[2. 2. 1]heptyl, bicyclo[2. 2. 2]octyl, bicyclo[3. 2. 1]octyl, and adamantyl.

Non-limiting examples of "optionally halogenated $C_{3-10}$ cycloalkyl groups" in the present specification include $C_{3-10}$ cycloalkyl groups which may have from 1 to 7, for example 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl, and cyclooctyl.

Non-limiting examples of "$C_{3-10}$ cycloalkenyl groups" in the present specification include cyclopropenyl, cyclobutenyl, cyclopentenyl, cyclohexenyl, cycloheptenyl, and cyclooctenyl.

Non-limiting examples of "$C_{6-14}$ aryl groups" in the present specification include phenyl, 1-naphthyl, 1-anthryl, 2-anthryl, and 9-anthryl. Non-limiting examples of "$C_{7-16}$ aralkyl groups" in the present specification include benzyl, phenethyl, naphthylmethyl, and phenylpropyl.

Non-limiting examples of "$C_{1-6}$ alkoxy groups" in the present specification include methoxy, ethoxy, propoxy, isopropoxy, butoxy, isobutoxy, sec-butoxy, tert-butoxy, pentyloxy, and hexyloxy.

Non-limiting examples of "optionally halogenated $C_{1-6}$ alkoxy groups" in the present specification include $C_{1-6}$ alkoxy groups which may have from 1 to 7, for example, from 1 to 5, halogen atoms. Further non-limiting examples thereof include methoxy, difluoromethoxy, tifluoromethoxy, ethoxy, 2,2,2-trifluoroethoxy, propoxy, isopropoxy, butoxy, 4,4,4-trifluorobutoxy, isobutoxy, sec-butoxy, pentyloxy, and hexyloxy.

Non-limiting examples of "$C_{3-10}$ cycloalkyloxy groups" in the present specification include cyclopropyloxy, cyclobutyloxy, cyclopentyloxy, cyclohexyloxy, cycloheptyloxy, and cyclooctyloxy.

Non-limiting examples of "$C_{1-6}$ alkylthio groups" in the present specification include methylthio, ethylthio, propylthio, isopropylthio, butylthio, sec-butylthio, tert-butylthio, pentylthio, and hexylthio.

Non-limiting examples of "optionally halogenated $C_{1-6}$ alkylthio groups" in the present specification include $C_{1-6}$ alkylthio groups which may have from 1 to 7, for example, from 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio, and hexylthio.

Non-limiting examples of "$C_{1-6}$ alkyl-carbonyl groups" in the present specification include acetyl, propanoyl, butanoyl, 2-methylpropanoyl, pentanoyl, 3-methylbutanoyl, 2-methylbutanoyl, 2,2-dimethylpropanoyl, hexanoyl, and heptanoyl.

Non-limiting examples of "optionally halogenated $C_{1-6}$ alkyl-carbonyl groups" in the present specification include $C_{1-6}$ alkyl-carbonyl groups which may have from 1 to 7, for example, from 1 to 5, halogen atoms. Further non-limiting examples thereof include acetyl, chloroacetyl, trifluoroacetyl, trichloroacetyl, propanoyl, butanoyl, pentanoyl, and hexanoyl.

Non-limiting examples of "$C_{1-6}$ alkoxy-carbonyl groups" in the present specification include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, and hexyloxycarbonyl.

Non-limiting examples of "$C_{6-14}$ aryl-carbonyl groups" in the present specification include benzoyl, 1-naphthoyl, and 2-naphthoyl.

Non-limiting examples of "$C_{7-16}$ aralkyl-carbonyl groups" in the present specification include phenylacetyl and phenylpropionyl.

Non-limiting examples of "5- to 14-membered aromatic heterocyclic carbonyl groups" in the present specification include nicotinoyl, isonicotinoyl, thenoyl, and furoyl.

Non-limiting examples of "3- to 14-membered non-aromatic heterocyclic carbonyl groups" in the present specification include morpholinylcarbonyl, piperidinylcarbonyl, and pyrrolidinylcarbonyl.

Non-limiting examples of "mono- or di-$C_{1-6}$ alkyl-carbamoyl groups" in the present specification include methylcarbamoyl, ethylcarbamoyl, dimethylcarbamoyl, diethylcarbamoyl, and N-ethyl-N-methylcarbamoyl.

Non-limiting examples of "mono- or di-$C_{7-16}$ aralkyl-carbamoyl groups" in the present specification include benzylcarbamoyl and phenethylcarbamoyl.

Non-limiting examples of "$C_{1-6}$ alkylsulfonyl groups" in the present specification include methylsulfonyl, ethylsulfonyl, propylsulfonyl, isopropylsulfonyl, butylsulfonyl, sec-butylsulfonyl, and tert-butylsulfonyl.

Non-limiting examples of "optionally halogenated $C_{1-6}$ alkylsulfonyl groups" in the present specification include $C_{1-6}$ alkylsulfonyl groups which may have from 1 to 7, for example, from 1 to 5, halogen atoms. Further non-limiting examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl, and hexylsulfonyl.

Non-limiting examples of "$C_{6-14}$ arylsulfonyl groups" in the present specification include phenylsulfonyl, 1-naphthylsulfonyl, and 2-naphthylsulfonyl.

Non-limiting examples of"substituents" in the present specification include halogen atoms, cyano groups, nitro groups, optionally substituted hydrocarbon groups, optionally substituted heterocyclic groups, acyl groups, optionally substituted amino groups, optionally substituted carbamoyl groups, optionally substituted thiocarbamoyl groups, optionally substituted sulfamoyl groups, optionally substituted hydroxy groups, optionally substituted sulfanyl (SH) groups, and optionally substituted silyl groups.

Non-limiting examples of "hydrocarbon groups," including "hydrocarbon groups" in "optionally substituted hydrocarbon groups," in the present specification include $C_{1-6}$ alkyl groups, $C_{2-6}$ alkenyl groups, $C_{2-6}$ alkynyl groups, $C_{3-10}$ cycloalkyl groups, $C_{3-10}$ cycloalkenyl groups, $C_{6-14}$ aryl groups, and $C_{7-16}$ aralkyl groups.

Non-limiting examples of "optionally substituted hydrocarbon groups" in the present specification include hydrocarbon groups which may have substituents chosen from substituent group A.

Substituent group A:

(1) halogen atoms;
(2) nitro groups;
(3) cyano groups;
(4) oxo groups;
(5) hydroxy groups;
(6) optionally halogenated $C_{1-6}$ alkoxy groups;
(7) $C_{6-14}$ aryloxy groups (for example, phenoxy or naphthoxy);
(8) $C_{7-16}$ aralkyloxy groups (for example, benzyloxy);
(9) 5- to 14-membered aromatic heterocyclic oxy groups (for example, pyridyloxy);
(10) 3- to 14-membered non-aromatic heterocyclic oxy groups (for example, morpholinyloxy or piperidinyloxy);
(11) $C_{1-6}$ alkyl-carbonyloxy groups (for example, acetoxy or propanoyloxy);
(12) $C_{6-14}$ aryl-carbonyloxy groups (for example, benzoyloxy, 1-naphthoyloxy, or 2-naphthoyloxy);
(13) $C_{1-6}$ alkoxy-carbonyloxy groups (for example, methoxycarbonyloxy, ethoxycarbonyloxy, propoxycarbonyloxy, or butoxycarbonyloxy);
(14) mono- or di-$C_{1-6}$ alkyl-carbamoyloxy groups (for example, methylcarbamoyloxy, ethylcarbamoyloxy, dimethylcarbamoyloxy, or diethylcarbamoyloxy);
(15) $C_{6-14}$ aryl-carbamoyloxy groups (for example, phenylcarbamoyloxy or naphthylcarbamoyloxy);
(16) 5- to 14-membered aromatic heterocyclic carbonyloxy groups (for example, nicotinoyloxy);
(17) 3- to 14-membered non-aromatic heterocyclic carbonyloxy groups (for example, morpholinylcarbonyloxy or piperidinylcarbonyloxy);
(18) optionally halogenated $C_{1-6}$ alkylsulfonyloxy groups (for example, methylsulfonyloxy or trifluoromethylsulfonyloxy);
(19) $C_{6-14}$ arylsulfonyloxy groups optionally substituted with $C_{1-6}$ alkyl groups (for example, phenylsulfonyloxy or toluenesulfonyloxy);
(20) optionally halogenated $C_{1-6}$ alkylthio groups;
(21) 5- to 14-membered aromatic heterocyclic groups;
(22) 3- to 14-membered non-aromatic heterocyclic groups;
(23) formyl groups;
(24) carboxy groups;
(25) optionally halogenated $C_{1-6}$ alkyl-carbonyl groups;

(26) $C_{6-14}$ aryl-carbonyl groups;
(27) 5- to 14-membered aromatic heterocyclic carbonyl groups;
(28) 3- to 14-membered non-aromatic heterocyclic carbonyl groups;
(29) $C_{1-6}$ alkoxy-carbonyl groups;
(30) $C_{6-14}$ aryloxy-carbonyl groups (for example, phenyloxycarbonyl, 1-naphthyloxycarbonyl, or 2-naphthyloxycarbonyl);
(31) $C_{7-16}$ aralkyloxy-carbonyl groups (for example, benzyloxycarbonyl or phenethyloxycarbonyl);
(32) carbamoyl groups;
(33) thiocarbamoyl groups;
(34) mono- or di-$C_{1-6}$ alkyl-carbamoyl groups;
(35) $C_{6-14}$ aryl-carbamoyl groups (for example, phenylcarbamoyl);
(36) 5- to 14-membered aromatic heterocyclic carbamoyl groups (for example, pyridylcarbamoyl or thienylcarbamoyl);
(37) 3- to 14-membered non-aromatic heterocyclic carbamoyl groups (for example, morpholinylcarbamoyl or piperidinylcarbamoyl);
(38) optionally halogenated $C_{1-6}$ alkylsulfonyl groups;
(39) $C_{6-14}$ arylsulfonyl groups;
(40) 5- to 14-membered aromatic heterocyclic sulfonyl groups (for example, pyridylsulfonyl or thienylsulfonyl);
(41) optionally halogenated $C_{1-6}$ alkylsulfinyl groups;
(42) $C_{6-14}$ arylsulfinyl groups (for example, phenylsulfinyl, 1-naphthylsulfinyl, or 2-naphthylsulfinyl);
(43) 5- to 14-membered aromatic heterocyclic sulfinyl groups (for example, pyridylsulfinyl or thienylsulfinyl);
(44) amino groups;
(45) mono- or di-$C_{1-6}$ alkylamino groups (for example, methylamino, ethylamino, propylamino, isopropylamino, butylamino, dimethylamino, diethylamino, dipropylamino, dibutylamino, or N-ethyl-N-methylamino);
(46) mono- or di-$C_{6-14}$ arylamino groups (for example, phenylamino);
(47) 5- to 14-membered aromatic heterocyclic amino groups (for example, pyridylamino);
(48) $C_{7-16}$ aralkylamino groups (for example, benzylamino);
(49) formylamino groups;
(50) $C_{1-6}$ alkyl-carbonylamino groups (for example, acetylamino, propanoylamino, or butanoylamino);
(51) ($C_{1-6}$ alkyl)($C_{1-6}$ alkyl-carbonyl)amino groups (for example, N-acetyl-N-methylamino);
(52) $C_{6-14}$ aryl-carbonylamino groups (for example, phenylcarbonylamino or naphthylcarbonylamino);
(53) $C_{1-6}$ alkoxy-carbonylamino groups (for example, methoxycarbonylamino, ethoxycarbonylamino, propoxycarbonylamino, butoxycarbonylamino, or tert-butoxycarbonylamino);
(54) $C_{7-16}$ aralkyloxy-carbonylamino groups (for example, benzyloxycarbonylamino);
(55) $C_{1-6}$ alkylsulfonylamino groups (for example, methylsulfonylamino or ethylsulfonylamino);
(56) $C_{6-14}$ arylsulfonylamino groups optionally substituted with $C_{1-6}$ alkyl groups (for example, phenylsulfonylamino or toluenesulfonylamino);
(57) optionally halogenated $C_{1-6}$ alkyl groups;
(58) $C_{2-6}$ alkenyl groups;
(59) $C_{2-6}$ alkynyl groups;
(60) $C_{3-10}$ cycloalkyl groups;
(61) $C_{3-10}$ cycloalkenyl groups; and
(62) $C_{6-14}$ aryl groups.

The number of the aforementioned substituents in the "optionally substituted hydrocarbon group" is, for example, from 1 to 5, such as, for example, from 1 to 3. When the number of substituents is 2 or greater, the respective substituents may be the same or different from one another.

Non-limiting examples of "heterocyclic groups," including "heterocyclic groups" in "optionally substituted heterocyclic groups," in the present specification include (i) aromatic heterocyclic groups, (ii) non-aromatic heterocyclic groups, and (iii) 7- to 10-membered heterocyclic bridged ring groups, each containing from 1 to 4 hetero atoms chosen from nitrogen atoms, sulfur atoms, and oxygen atoms in addition to carbon atoms as annular atoms.

Non-limiting examples of "aromatic heterocyclic groups," including "5- to 14-membered aromatic heterocyclic groups," in the present specification include 5- to 14-membered (such as, for example, 5- to 10-membered) aromatic heterocyclic groups containing from 1 to 4 hetero atoms chosen from nitrogen atoms, sulfur atoms, and oxygen atoms in addition to carbon atoms as annular atoms.

Non-limiting examples of these "aromatic heterocyclic groups" include 5- or 6-membered monocyclic aromatic heterocyclic groups such as thienyl, furyl, pyrrolyl, imidazolyl, pyrazolyl, thiazolyl, isothiazolyl, oxazolyl, isooxazolyl, pyridyl, pyradinyl, pyrimidinyl, pyridadinyl, 1,2,4-oxadiazolyl, 1,3,4-oxadiazolyl, 1,2,4-thiadiazolyl, 1,3,4-thiadiazolyl, triazolyl, tetrazolyl, and triadinyl; and 8- to 14-membered condensed polycyclic (such as, for example, 2- or 3-cyclic) aromatic heterocyclic groups such as benzothiophenyl, benzofuranyl, benzoimidazolyl, benzooxazolyl, benzoisooxazolyl, benzothiazolyl, benzoisothiazolyl, benzotriazolyl, imidazopyridinyl, thienopyridinyl, fluoropyridinyl, pyrrolopyridinyl, pyrazolopyridinyl, oxazolopyridinyl, thiazolopyridinyl, imidazopyradinyl, imidazopyrimidinyl, thienopyrimidinyl, fluoropyrimidinyl, pyrrolopyrimidinyl, pyrazolopyrimidinyl, oxazolopyrimidinyl, thiazolopyrimidinyl, pyrazolotriadinyl, naphtho[2,3-b]thienyl, phenoxathiinyl, indolyl, isoindolyl, 1H-indazolyl, purinyl, isoquinolyl, quinolyl, phthaladinyl, naphthylidinyl, quinoxalinyl, quinazolinyl, cinnolinyl, carbazolyl, β-carbolinyl, phenanthridinyl, acridinyl, phenadinyl, phenothiadinyl, and phenoxadinyl.

Non-limiting examples of "non-aromatic heterocyclic groups," including "3- to 14-membered non-aromatic heterocyclic groups," in the present specification include 3- to 14-membered (such as, for example, 4- to 10-membered) non-aromatic heterocyclic groups containing from 1 to 4 hetero atoms chosen from nitrogen atoms, sulfur atoms, and oxygen atoms in addition to carbon atoms as annular atoms.

Non-limiting examples of these "non-aromatic heterocyclic groups" include 3- to 8-membered monocyclic non-aromatic heterocyclic groups such as aziridinyl, oxylanyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperadinyl, tetrahydropyridinyl, dihydropyridinyl, dihydrothiopyranyl, tetrahydropyrimidinyl, tetrahydropyridazonyl, dihydropyranyl, tetrahydropyranyl, tetrahydrothiopyranyl, morpholinyl, thiomorpholinyl, azepanyl, diazepanyl, azepinyl, oxepanyl, azocanyl, and azocanyl; and 9- to 14-membered condensed polycyclic (such as, for example, 2- or 3-cyclic) non-aromatic heterocyclic groups such as dihydrobenzofuranyl, dihydrobenzoimidazolyl, dihydrobenzothiazolyl, dihydrobenzoisothiazolyl, dihydronaphtho[2,3-b]thienyl, tetrahydroisoquinolyl, tetrahydroquinolyl, 4H-quinolidinyl, indolinyl, isoindolinyl, tetrahydrothieno[2,3-c]pyridinyl, tetrahydrobenzoazepinyl, tetrahydroquinoxalinyl, tetrahydrophenanthridinyl, hexahydrophenothiadinyl, hexahydrophenoxadinyl, tetrahydrophthaladinyl, tetrahydronaphthylidinyl, tetrahydroquinazolinyl, tetrahydrocinnolinyl, tetrahydrocarbazolyl, tetrahydro-p-carbolinyl, tetrahydroacrydinyl, tetrahydrophenadinyl, tetrahydrothioxanthenyl, and octahydroisoquinolyl.

Non-limiting examples of “7- to 10-membered heterocyclic bridged ring groups” in the present specification include quinuclidinyl and 7-azabicyclo[2. 2. 1]heptanyl.

Non-limiting examples of “nitrogen-containing heterocyclic groups” in the present specification include “heterocyclic groups” containing at least one nitrogen atom as an annular atom.

Non-limiting examples of “optionally substituted heterocyclic groups” in the present specification include heterocyclic groups which may have substituents chosen from substituent group A. The number of substituents in the “optionally substituted heterocyclic groups” is, for example, from 1 to 3. When the number of substituents is 2 or greater, the respective substituents may be the same or different from one another.

Non-limiting examples of “acyl groups” in the present specification include formyl groups, carboxy groups, thiocarbamoyl groups, sulfino groups, sulfo groups, sulfamoyl groups, and phosphono groups which may each have 1 or 2 substituents chosen from $C_{1-6}$ alkyl groups, $C_{2-6}$ alkenyl groups, $C_{3-10}$ cycloalkyl groups, $C_{3-10}$ cycloalkenyl groups, $C_{6-14}$ aryl groups, $C_{7-16}$ aralkyl groups, 5- to 14-membered aromatic heterocyclic groups, and 3- to 14-membered non-aromatic heterocyclic groups which may each have from 1 to 3 substituents chosen from halogen atoms, optionally halogenated $C_{1-6}$ alkoxy groups, hydroxy groups, nitro groups, cyano groups, amino groups, and carbamoyl groups. Additional non-limiting examples of acyl groups include hydrocarbon-sulfonyl groups, heterocycle-sulfonyl groups, hydrocarbon sulfinyl groups, and heterocycle-sulfinyl groups.

As used herein, a hydrocarbon-sulfonyl group refers to a sulfonyl group to which a hydrocarbon group is bonded; a heterocycle-sulfonyl group refers to a sulfonyl group to which a heterocyclic group is bonded; a hydrocarbon-sulfinyl group refers to a sulfinyl group to which a hydrocarbon group is bonded; and a heterocycle-sulfinyl group refers to a sulfinyl group to which a heterocyclic group is bonded.

Additionally, non-limiting examples of “acyl groups” further include formyl groups, carboxy groups, $C_{1-6}$ alkyl-carbonyl groups, $C_{2-6}$ alkenyl-carbonyl groups (for example, crotonoyl), $C_{3-10}$ cycloalkyl-carbonyl groups (for example, cyclobutanecarbonyl, cyclopentanecarbonyl, cyclohexanecarbonyl, or cycloheptanecarbonyl), $C_{3-10}$ cycloalkenyl-carbonyl groups (for example, 2-cyclohexenecarbonyl), $C_{6-14}$ aryl-carbonyl groups, $C_{7-16}$ aralkyl-carbonyl groups, 5- to 14-membered aromatic heterocyclic carbonyl groups, 3- to 14-membered non-aromatic heterocyclic carbonyl groups, $C_{1-6}$ alkoxy-carbonyl groups, $C_{6-14}$ aryloxy-carbonyl groups (for example, phenyloxycarbonyl or naphthyloxycarbonyl), $C_{7-16}$ aralkyloxy-carbonyl groups (for example, benzyloxycarbonyl or phenethyloxycarbonyl), carbamoyl groups, mono- or di-$C_{1-6}$ alkyl-carbamoyl groups, mono- or di-$C_{2-6}$ alkenyl-carbamoyl groups (for example, diallylcarbamoyl), mono- or di-$C_{3-10}$ cycloalkyl-carbamoyl groups (for example, cyclopropylcarbamoyl), mono- or di-$C_{6-14}$ aryl-carbamoyl groups (for example, phenylcarbamoyl), mono- or di-$C_{7-16}$ aralkyl-carbamoyl groups, 5- to 14-membered aromatic heterocyclic carbamoyl groups (for example, pyridylcarbamoyl), thiocarbamoyl groups, mono- or di-$C_{1-6}$ alkyl-thiocarbamoyl groups (for example, methylthiocarbamoyl or N-ethyl-N-methylthiocarbamoyl), mono- or di-$C_{2-6}$ alkenyl-thiocarbamoyl groups (for example, diallylthiocarbamoyl), mono- or di-$C_{3-10}$ cycloalkyl-thiocarbamoyl groups (for example, cyclopropylthiocarbamoyl or cyclohexylthiocarbamoyl), mono- or di-$C_{6-14}$ aryl-thiocarbamoyl groups (for example, phenylthiocarbamoyl), mono- or di-$C_{7-16}$ aralkyl-thiocarbamoyl groups (for example, benzylthiocarbamoyl or phenethylthiocarbamoyl), 5- to 14-membered aromatic heterocyclic thiocarbamoyl groups (for example, pyridylthiocarbamoyl), sulfino groups, $C_{1-6}$ alkylsulfinyl groups (for example, methylsulfinyl or ethylsulfinyl), sulfo groups, $C_{1-6}$ alkylsulfonyl groups, $C_{6-14}$ arylsulfonyl groups, phosphono groups, and mono- or di-$C_{1-6}$ alkylphosphono groups (for example, dimethylphosphono, diethylphosphono, diisopropylphosphono, or dibutylphosphono).

Non-limiting examples of “optionally substituted amino groups” in the present specification include amino groups which may have 1 or 2 substituents chosen from $C_{1-6}$ alkyl groups, $C_{2-6}$ alkenyl groups, $C_{3-10}$ cycloalkyl groups, $C_{6-14}$ aryl groups, $C_{7-16}$ aralkyl groups, $C_{1-6}$ alkyl-carbonyl groups, $C_{6-14}$ aryl-carbonyl groups, $C_{7-16}$ aralkyl-carbonyl groups, 5- to 14-membered aromatic heterocyclic carbonyl groups, 3- to 14-membered non-aromatic heterocyclic carbonyl groups, $C_{1-6}$ alkoxy-carbonyl groups, 5- to 14-membered aromatic heterocyclic groups, carbamoyl groups, mono- or di-$C_{1-6}$ alkyl-carbamoyl groups, mono- or di-$C_{7-16}$ aralkyl-carbamoyl groups, $C_{1-6}$ alkylsulfonyl groups, and $C_{6-14}$ arylsulfonyl groups which may each have from 1 to 3 substituents chosen from substituent group A.

Non-limiting examples of optionally substituted amino groups include amino groups, mono- or di-(optionally halogenated $C_{1-6}$ alkyl)amino groups (for example, methylamino, trifluoromethylamino, dimethylamino, ethylamino, diethylamino, propylamino, or dibutylamino), mono- or di-$C_{2-6}$ alkenylamino groups (for example, diallylamino), mono- or di-$C_{3-10}$ cycloalkylamino groups (for example, cyclopropylamino, cyclohexylamino), mono- or di-$C_{6-14}$ arylamino groups (for example, phenylamino), mono- or di-$C_{7-16}$ aralkylamino groups (for example, benzylamino, or dibenzylamino), mono- or di-(optionally halogenated $C_{1-6}$ alkyl)-carbonylamino groups (for example, acetylamino or propionylamino), mono- or di-$C_{6-14}$ aryl-carbonyl groups (for example, benzoylamino), mono- or di-$C_{7-16}$ aralkyl-carbonylamino groups (for example, benzylcarbonylamino), mono- or di- 5- to 14-membered aromatic heterocyclic carbonylamino groups (for example, nicotinoylamino or isonicotinoylamino), mono- or di-3- to 14-membered non-aromatic heterocyclic carbonylamino groups (for example, piperidinylcarbonylamino), mono- or di-$C_{1-6}$ alkoxy-carbonylamino groups (for example, tert-butoxycarbonylamino), 5- to 14-membered aromatic heterocyclic amino groups (for example, pyridylamino), carbamoylamino groups, (mono- or di-$C_{1-6}$ alkyl-carbamoyl)amino groups (for example, methylcarbamoylamino), (mono- or di-$C_{7-16}$ aralkyl-carbamoyl)amino groups (for example, benzylcarbamoylamino), $C_{1-6}$ alkylsulfonylamino groups (for example, methylsulfonylamino or ethylsulfonylamino), $C_{6-14}$ arylsulfonylamino groups (for example, phenylsulfonylamino), ($C_{1-6}$ alkyl)($C_{1-6}$ alkyl-carbonyl)amino groups (for example, N-acetyl-N-methylamino), and ($C_{1-6}$ alkyl)

($C_{6-14}$ aryl-carbonyl)amino groups (for example, N-benzoyl-N-methylamino) groups.

Non-limiting examples of "optionally substituted carbamoyl groups" in the present specification include carbamoyl groups which may have 1 or 2 substituents chosen from $C_{1-6}$ alkyl groups, $C_{2-6}$ alkenyl groups, $C_{3-10}$ cycloalkyl groups, $C_{6-14}$ aryl groups, $C_{7-16}$ aralkyl groups, $C_{1-6}$ alkyl-carbonyl groups, $C_{6-14}$ aryl-carbonyl groups, $C_{7-16}$ aralkyl-carbonyl groups, 5- to 14-membered aromatic heterocyclic carbonyl groups, 3- to 14-membered non-aromatic heterocyclic carbonyl groups, $C_{1-6}$ alkoxy-carbonyl groups, 5- to 14-membered aromatic heterocyclic groups, carbamoyl groups, mono- or di-Ct-6 alkyl-carbamoyl groups, and mono- or di-$C_{7-16}$ aralkyl-carbamoyl groups which may each have from 1 to 3 substituents chosen from substituent group A.

Illustratively, non-limiting examples of optionally substituted carbamoyl groups include carbamoyl groups, mono- or di-$C_{1-6}$ alkyl-carbamoyl groups, mono- or di-$C_{2-6}$ alkenyl-carbamoyl groups (for example, diallylcarbamoyl), mono- or di-$C_{3-10}$ cycloalkyl-carbamoyl groups (for example, cyclopropylcarbamoyl or cyclohexylcarbamoyl), mono- or di-$C_{6-14}$ aryl-carbamoyl groups (for example, phenylcarbamoyl), mono- or di-$C_{7-16}$ aralkyl-carbamoyl groups, mono- or di-$C_{1-6}$ alkyl-carbonyl-carbamoyl groups (for example, acetylcarbamoyl or propionylcarbamoyl), mono- or di-$C_{6-14}$ aryl-carbonyl-carbamoyl groups (for example, benzoylcarbamoyl), and 5- to 14-membered aromatic heterocyclic carbamoyl groups (for example, pyridylcarbamoyl).

Non-limiting examples of "optionally substituted thiocarbamoyl groups" in the present specification include thiocarbamoyl groups which may have 1 or 2 substituents chosen from $C_{1-6}$ alkyl groups, $C_{2-6}$ alkenyl groups, $C_{3-10}$ cycloalkyl groups, $C_{6-14}$ aryl groups, $C_{7-16}$ aralkyl groups, $C_{1-6}$ alkyl-carbonyl groups, $C_{6-14}$ aryl-carbonyl groups, $C_{7-16}$ aralkyl-carbonyl groups, 5- to 14-membered aromatic heterocyclic carbonyl groups, 3- to 14-membered non-aromatic heterocyclic carbonyl groups, $C_{1-6}$ alkoxy-carbonyl groups, 5- to 14-membered aromatic heterocyclic groups, carbamoyl groups, mono- or di-$C_{1-6}$ alkyl-carbamoyl groups, and mono- or di-$C_{7-16}$ aralkyl-carbamoyl groups which may each have from 1 to 3 substituents chosen from substituent group A.

Illustratively, non-limiting examples of optionally substituted thiocarbamoyl groups include thiocarbamoyl groups, mono- or di-$C_{1-6}$ alkyl-thiocarbamoyl groups (for example, methylthiocarbamoyl, ethylthiocarbamoyl, dimethylthiocarbamoyl, diethylthiocarbamoyl, or N-ethyl-N-methylthiocarbamoyl), mono- or di-$C_{2-6}$ alkenyl-thiocarbamoyl groups (for example, diallylthiocarbamoyl), mono- or di-$C_{3-10}$ cycloalkyl-thiocarbamoyl groups (for example, cyclopropylthiocarbamoyl or cyclohexylthiocarbamoyl), mono- or di-$C_{6-14}$ aryl-thiocarbamoyl groups (for example, phenylthiocarbamoyl), mono- or di-$C_{7-16}$ aralkyl-thiocarbamoyl groups (for example, benzylthiocarbamoyl or phenethylthiocarbamoyl), mono- or di-$C_{1-6}$ alkyl-carbonyl-thiocarbamoyl groups (for example, acetylthiocarbamoyl or propionylthiocarbamoyl), mono- or di-$C_{6-14}$ aryl-carbonyl-thiocarbamoyl groups (for example, benzoylthiocarbamoyl), and 5- to 14-membered aromatic heterocyclic thiocarbamoyl groups (for example, pyridylthiocarbamoyl).

Non-limiting examples of "optionally substituted sulfamoyl groups" in the present specification include sulfamoyl groups which may have 1 or 2 substituents chosen from $C_{1-6}$ alkyl groups, $C_{2-6}$ alkenyl groups, $C_{3-10}$ cycloalkyl groups, $C_{6-14}$ aryl groups, $C_{7-16}$ aralkyl groups, $C_{1-6}$ alkyl-carbonyl groups, $C_{6-14}$ aryl-carbonyl groups, $C_{7-16}$ aralkyl-carbonyl groups, 5- to 14-membered aromatic heterocyclic carbonyl groups, 3- to 14-membered non-aromatic heterocyclic carbonyl groups, $C_{1-6}$ alkoxy-carbonyl groups, 5- to 14-membered aromatic heterocyclic groups, carbamoyl groups, mono- or di-$C_{1-6}$ alkyl-carbamoyl groups, and mono- or di-$C_{7-16}$ aralkyl-carbamoyl groups which may each have from 1 to 3 substituents chosen from substituent group A.

Illustratively, non-limiting examples of optionally substituted sulfamoyl groups include sulfamoyl groups, mono- or di-$C_{1-6}$ alkyl-sulfamoyl groups (for example, methylsulfamoyl, ethylsulfamoyl, dimethylsulfamoyl, diethylsulfamoyl, or N-ethyl-N-methylsulfamoyl), mono- or di-$C_{2-6}$ alkenyl-sulfamoyl groups (for example, diallylsulfamoyl), mono- or di-$C_{3-10}$ cycloalkyl-sulfamoyl groups (for example, cyclopropylsulfamoyl, cyclohexylsulfamoyl), mono- or di-$C_{6-14}$ aryl-sulfamoyl groups (for example, phenylsulfamoyl), mono- or di-$C_{7-16}$ aralkyl-sulfamoyl groups (for example, benzylsulfamoyl, or phenethylsulfamoyl), mono- or di-$C_{1-6}$ alkyl-carbonyl-sulfamoyl groups (for example, acetylsulfamoyl or propionylsulfamoyl), mono- or di-$C_{6-14}$ aryl-carbonyl-sulfamoyl groups (for example, benzoylsulfamoyl), and 5- to 14-membered aromatic heterocyclic sulfamoyl groups (for example, pyridylsulfamoyl).

Non-limiting examples of "optionally substituted hydroxy groups" in the present specification include hydroxy groups which may have substituents chosen from $C_{1-6}$ alkyl groups, $C_{2-6}$ alkenyl groups, $C_{3-10}$ cycloalkyl groups, $C_{6-14}$ aryl groups, $C_{7-16}$ aralkyl groups, $C_{1-6}$ alkyl-carbonyl groups, $C_{6-14}$ aryl-carbonyl groups, $C_{7-16}$ aralkyl-carbonyl groups, 5- to 14-membered aromatic heterocyclic carbonyl groups, 3- to 14-membered non-aromatic heterocyclic carbonyl groups, $C_{1-6}$ alkoxy-carbonyl groups, 5- to 14-membered aromatic heterocyclic groups, carbamoyl groups, mono- or di-$C_{1-6}$ alkyl-carbamoyl groups, mono- or di-$C_{7-16}$ aralkyl-carbamoyl groups, $C_{1-6}$ alkylsulfonyl groups, and $C_{6-14}$ arylsulfonyl groups which may each have from 1 to 3 substituents chosen from substituent group A.

Illustratively, non-limiting examples of optionally substituted hydroxy groups include hydroxy groups, $C_{1-6}$ alkoxy groups, $C_{2-6}$ alkenyloxy groups (for example, allyloxy, 2-butenyloxy, 2-pentenyloxy, or 3-hexenyloxy), $C_{3-10}$ cycloalkyloxy groups (for example, cyclohexyloxy), $C_{6-14}$ aryloxy groups (for example, phenoxy or naphthyloxy), $C_{7-16}$ aralkyloxy groups (for example, benzyloxy or phenethyloxy), $C_{1-6}$ alkyl-carbonyloxy groups (for example, acetyloxy, propionyloxy, butyryloxy, isobutyryloxy, or pivaloyloxy), $C_{6-14}$ aryl-carbonyloxy groups (for example, benzoyloxy), $C_{7-16}$ aralkyl-carbonyloxy groups (for example, benzylcarbonyloxy), 5- to 14-membered aromatic heterocyclic carbonyloxy groups (for example, nicotinoyloxy), 3- to 14-membered non-aromatic heterocyclic carbonyloxy groups (for example, piperidinylcarbonyloxy), $C_{1-6}$ alkoxy-carbonyloxy groups (for example, tert-butoxycarbonyloxy), 5- to 14-membered aromatic heterocyclic oxy groups (for example, pyridyloxy), carbamoyloxy groups, $C_{1-6}$ alkyl-carbamoyloxy groups (for example, methylcarbamoyloxy), $C_{7-16}$ aralkyl-carbamoyloxy groups (for example, benzylcarbamoyloxy), $C_{1-6}$ alkylsulfonyloxy groups (for example, methylsulfonyloxy or ethylsulfonyloxy), and $C_{6-14}$ arylsulfonyloxy groups (for example, phenylsulfonyloxy).

Non-limiting examples of "optionally substituted sulfanyl groups" in the present specification include sulfanyl groups and halogenated sulfanyl groups which may have substituents chosen from $C_{1-6}$ alkyl groups, $C_{2-6}$ alkenyl groups, $C_{3-10}$ cycloalkyl groups, $C_{6-14}$ aryl groups, $C_{7-16}$ aralkyl groups, $C_{1-6}$ alkyl-carbonyl groups, $C_{6-14}$ aryl-carbonyl groups, and 5 to 14-membered aromatic heterocyclic groups which may each have from 1 to 3 substituents chosen from substituent group A."

Illustratively, non-limiting examples of optionally substituted sulfanyl groups include sulfanyl (—SH) groups, $C_{1-6}$ alkylthio groups, $C_{2-6}$ alkenylthio groups (for example, allylthio, 2-butenylthio, 2-pentenylthio, or 3-hexenylthio), $C_{3-10}$ cycloalkylthio groups (for example, cyclohexylthio), $C_{6-14}$ arylthio groups (for example, phenylthio or naphthylthio), $C_{7-16}$ aralkylthio groups (for example, benzylthio or phenethylthio), $C_{1-6}$ alkyl-carbonylthio groups (for example, acetylthio, propionylthio, butylthio, isobutylthio, or pivaloylthio), $C_{6-14}$ aryl-carbonylthio groups (for example, benzoylthio), 5- to 14-membered aromatic heterocyclic thio groups (for example, pyridylthio), and halogenated thio groups (for example, pentafluorothio).

Non-limiting examples of "optionally substituted silyl groups" in the present specification include silyl groups which may have from 1 to 3 substituents chosen from $C_{1-6}$ alkyl groups, $C_{2-6}$ alkenyl groups, $C_{3-10}$ cycloalkyl groups, $C_{6-14}$ aryl groups, and $C_{7-16}$ aralkyl groups which may each have from 1 to 3 substituents chosen from substituent group A.

Illustratively, non-limiting examples of optionally substituted silyl groups include tri-$C_{1-6}$ alkylsilyl groups (for example, trimethylsilyl or tert-butyl(dimethyl)silyl).

Non-limiting examples of "hydrocarbon rings" in the present specification include $C_{6-14}$ aromatic hydrocarbon rings, $C_{3-10}$ cycloalkanes, and $C_{3-10}$ cycloalkenes.

Non-limiting examples of "$C_{6-14}$ aromatic hydrocarbon groups" in the present specification include benzene and naphthalene.

Non-limiting examples of "$C_{3-10}$ cycloalkanes" in the present specification include cyclopropane, cyclobutane, cyclopentane, cyclohexane, cycloheptane, and cyclooctane.

Non-limiting examples of "$C_{3-10}$ cycloalkenes" in the present specification include cyclopropene, cyclobutene, cyclopentene, cyclohexene, cycloheptene, and cyclooctene.

Non-limiting examples of "heterocyclic rings" in the present specification include aromatic heterocyclic rings and non-aromatic heterocyclic rings which respectively contain from 1 to 4 hetero atoms chosen from nitrogen atoms, sulfur atoms, and oxygen atoms in addition to carbon atoms as annular atoms.

Non-limiting examples of "aromatic heterocyclic rings" in the present specification include 5- to 14-membered (such as, for example, 5- to 10-membered) aromatic heterocyclic rings containing from 1 to 4 hetero atoms chosen from nitrogen atoms, sulfur atoms, and oxygen atoms in addition to carbon atoms as annular atoms. Illustratively, non-limiting examples of these "aromatic heterocyclic rings" include 5- or 6-membered monocyclic aromatic heterocyclic rings such as thiophene, furan, pyrrole, imidazole, pyrazole, thiazole, isothiazole, oxazole, isooxazole, pyridine, pyrazine, pyrimidine, pyridazine, 1,2,4-oxadiazole, 1,3,4-oxadiazolyl, 1,2,4-thiadiazole, 1,3,4-thiadiazole, triazole, tetrazole, and triazine; and 8- to 14-membered condensed polycyclic (such as, for example, 2- or 3-cyclic) aromatic heterocyclic rings such as benzothiophene, benzofuran, benzoimidazole, benzooxazole, benzoisooxazole, benzothiazole, benzoisothiazole, benzotriazole, imidazopyridine, thienopyridine, fluoropyridine, pyrrolopyridine, pyrazolopyridine, oxazolopyridine, thiazolopyridine, imidazopyradine, imidazopyrimidine, thienopyrimidine, fluoropyrimidine, pyrrolopyrimidine, pyrazolopyrimidine, oxazolopyrimidine, thiazolopyrimidine, pyrazolotriazine, naphtho[2,3-b]thiophene, phenoxathiine, indole, isoindole, 1H-indazole, purine, isoquinoline, quinoline, phthalazine, naphthylidine, quinoxaline, quinazoline, cinnoline, carbazole, O-carboline, phenanthridine, acridine, phenazine, phenothiazine, and phenoxazine.

Non-limiting examples of "non-aromatic heterocyclic rings" in the present specification include 3- to 14-membered (such as, for example, 4- to 10-membered) non-aromatic heterocyclic rings containing from 1 to 4 hetero atoms chosen from nitrogen atoms, sulfur atoms, and oxygen atoms in addition to carbon atoms as annular atoms. Illustratively, non-limiting examples of these "non-aromatic heterocyclic rings" include 3- to 8-membered monocyclic non-aromatic heterocyclic rings such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisooxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepane, diazepane, azepine, azocane, diazocane, and oxepane; and 9- to 14-membered condensed polycyclic (such as, for example, 2- or 3-cyclic) non-aromatic heterocyclic groups such as dihydrobenzofuran, dihydrobenzoimidazole, dihydrobenzothiazole, dihydrobenzoisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzoazepine, tetrahydroquinoxaline, tetrahydrophenanthridine, hexahydrophenothiazine, hexahydrophenoxazine, tetrahydrophthalazine, tetrahydronaphthylidine, tetrahydroquinazoline, tetrahydrocinnoline, tetrahydrocarbazole, tetrahydro-β-carboline, tetrahydroacridine, tetrahydrophenadine, tetrahydrothioxanthene, and octahydroisoquinole.

Non-limiting examples of "nitrogen-containing heterocyclic rings" in the present specification include "heterocyclic rings" containing at least one nitrogen atom as an annular atom.

Non-limiting examples of "6-membered aromatic rings" in the present specification include benzene, pyridine, pyridazine, pyrimidine, pyrazine, and triazine.

Non-limiting examples of "5-membered monocyclic aromatic heterocyclic rings" in the present specification include thiophene, furan, pyrrole, imidazole, pyrazole, thiazole, isothiazole, oxazole, isooxazole, 1,2,4-oxadiazole, 1,3,4-oxadiazolyl, 1,2,4-thiadiazole, 1,3,4-thiadiazole, triazole, and tetrazole.

The definitions of each of the symbols in Formula (I) will be described in further detail hereinafter.

In some embodiments, $R^1$ is

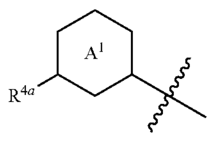

or

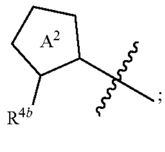

;

wherein ring $A^1$ is chosen from optionally further substituted 6-membered aromatic rings;

ring $A^2$ is chosen from optionally further substituted 5-membered monocyclic aromatic heterocyclic rings; and $R^{4a}$ and $R^{4b}$ are each independently chosen from substituents.

In some embodiments, $R^1$ is

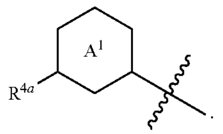

In some embodiments, the "6-membered aromatic ring" of the "optionally further substituted 6-membered aromatic ring" represented by ring $A^1$ is benzene, pyridine, or pyrimidine. In some embodiments, the "6-membered aromatic ring" of the "optionally further substituted 6-membered aromatic ring" represented by ring $A^1$ is benzene.

Non-limiting examples of optional substituents in the "optionally further substituted 6-membered aromatic ring" represented by ring $A^1$ are substituents chosen from substituent group A. In some embodiments, the number of these optional substituents is 1, 2, or 3. When the number of optional substituents is 2 or greater, the respective optional substituents may be the same or different from one another.

In some embodiments, ring $A^1$ is chosen from 6-membered aromatic rings (for example, benzene, pyridine, or pyrimidine) optionally further substituted with 1 to 3 substituents chosen from:

(a) halogen atoms (for example, fluorine atoms or bromine atoms);
(b) cyano groups;
(c) optionally halogenated $C_{1-6}$ alkyl groups (for example, methyl, isopropyl, difluoromethyl, trifluoromethyl, or 2,2,2-trifluoroethyl);
(d) optionally halogenated $C_{1-6}$ alkoxy groups (for example, trifluoromethoxy, 2,2-difluoroethoxy, or 2,2,2-trifluoroethoxy); and
(e) $C_{3-10}$ cycloalkyl groups (for example, cyclopropyl) optionally substituted with 1 to 3 halogen atoms (for example, fluorine atoms).

In some embodiments, ring $A^1$ is chosen from:

(1) benzene rings optionally further substituted with 1 to 3 substituents chosen from:
 (a) halogen atoms (for example, fluorine atoms or bromine atoms);
 (b) optionally halogenated $C_{1-6}$ alkyl groups (for example, isopropyl, trifluoromethyl, or 2,2,2-trifluoroethyl);
 (c) optionally halogenated $C_{1-6}$ alkoxy groups (for example, trifluoromethoxy); and
 (d) $C_{3-10}$ cycloalkyl groups (for example, cyclopropyl) optionally substituted with 1 to 3 halogen atoms (for example, fluorine atoms);
(2) pyridine rings optionally further substituted with 1 to 3 substituents chosen from:
 (a) halogen atoms (for example, fluorine atoms);
 (b) cyano groups;
 (c) optionally halogenated $C_{1-6}$ alkyl groups (for example, methyl, difluoromethyl, or trifluoromethyl); and
 (d) optionally halogenated $C_{1-6}$ alkoxy groups (for example, 2,2-difluoroethoxy or 2,2,2-trifluoroethoxy); and
(3) pyrimidine rings optionally further substituted with 1 or 2 optionally halogenated $C_{1-6}$ alkyl groups (for example, trifluoromethyl).

In some embodiments, ring $A^1$ is chosen from:

(1) benzene rings optionally further substituted with 1 to 3 substituents chosen from:
 (a) halogen atoms (for example, fluorine atoms or bromine atoms);
 (b) optionally halogenated $C_{1-6}$ alkyl groups (for example, isopropyl, trifluoromethyl, or 2,2,2-trifluoroethyl);
 (c) optionally halogenated $C_{1-6}$ alkoxy groups (for example, trifluoromethoxy); and
 (d) a $C_{3-6}$ cycloalkyl groups (for example, cyclopropyl) optionally substituted with 1 to 3 halogen atoms (for example, fluorine atoms);
(2) pyridine rings optionally further substituted with 1 to 3 substituents chosen from:
 (a) halogen atoms (for example, fluorine atoms);
 (b) cyano groups;
 (c) optionally halogenated $C_{1-6}$ alkyl groups (for example, methyl, difluoromethyl, or trifluoromethyl); and
 (d) optionally halogenated $C_{1-6}$ alkoxy groups (for example, 2,2-difluoroethoxy or 2,2,2-trifluoroethoxy); and
(3) pyrimidine rings optionally further substituted with 1 or 2 optionally halogenated $C_{1-6}$ alkyl groups (for example, trifluoromethyl).

In some embodiments, ring $A^1$ is chosen from pyridine rings further substituted with 1 or 2 substituents chosen from:

(a) halogen atoms (for example, fluorine atoms);
(b) $C_{1-6}$ alkyl groups (for example, isopropyl); and
(c) $C_{3-6}$ cycloalkyl groups (for example, cyclopropyl).

In some embodiments, ring $A^1$ is chosen from benzene rings further substituted with 1 or 2 substituents chosen from:

(a) halogen atoms (for example, fluorine atoms); and
(b) $C_{3-6}$ cycloalkyl groups (for example, cyclopropyl).

In some embodiments, ring $A^1$ is chosen from optionally further substituted benzene rings, optionally further substituted pyridine rings, and optionally further substituted pyrimidine rings. In some embodiments, ring $A^1$ is chosen from optionally further substituted benzene rings. In some embodiments, ring $A^1$ is chosen from further substituted benzene rings.

In some embodiments, $R^{4a}$ is chosen from:

(1) optionally substituted $C_{6-14}$ aryl groups (for example, phenyl);
(2) optionally substituted 3- to 14-membered non-aromatic heterocyclic groups (for example, 3- to 8-membered monocyclic non-aromatic heterocyclic groups (for example, morpholinyl or piperidyl));
(3) —$NR^9R^{10}$, wherein:
 $R^9$ is chosen from optionally substituted $C_{1-6}$ alkyl groups (for example, methyl); and
 $R^{10}$ is chosen from a hydrogen atom and optionally substituted $C_{1-6}$ alkyl groups (for example, methyl)); and
(4) —$OR^{11}$, wherein $R^{11}$ is chosen from optionally substituted 3- to 14-membered non-aromatic heterocyclic groups (for example, 3- to 8-membered monocyclic non-aromatic heterocyclic groups (for example, tetrahydropyranyl)).

In some embodiments, the substituents in the "optionally substituted $C_{6-14}$ aryl groups," the "optionally substituted $C_{1-6}$ alkyl groups," and the "optionally substituted 3- to 14-membered non-aromatic heterocyclic groups" are substituents chosen from substituent group A. In some embodiments, the number of these optional substituents is 1, 2, or 3. When the number of optional substituents is 2 or greater, the respective optional substituents may be the same or different from one another.

In some embodiments, the "3- to 14-membered non-aromatic heterocyclic groups" of the "optionally substituted 3- to 14-membered non-aromatic heterocyclic groups" described above include 6- to 9-membered non-aromatic spiro heterocyclic groups.

In some embodiments, $R^{4a}$ is chosen from:

(1) optionally substituted $C_{6-14}$ aryl groups (for example, phenyl);

(2) optionally substituted 3- to 14-membered non-aromatic heterocyclic groups (for example, 3- to 8-membered monocyclic non-aromatic heterocyclic groups (for example, morpholinyl or piperidyl));

(3) optionally substituted mono- or di-$C_{1-6}$ alkylamino groups (for example, methylamino or dimethylamino); and (4) optionally substituted 3- to 14-membered non-aromatic heterocyclic oxy groups (for example, 3- to 8-membered monocyclic non-aromatic heterocyclic oxy groups (for example, tetrahydropyranyloxy)).

In some embodiments, $R^4$, is chosen from:

(1) $C_{6-14}$ aryl groups (for example, phenyl) optionally substituted with 1 to 3 halogen atoms (for example, fluorine atoms);

(2) 3- to 14-membered non-aromatic heterocyclic groups (for example, 3- to 8-membered monocyclic non-aromatic heterocyclic groups (for example, morpholinyl or piperidyl)) optionally substituted with 1 to 3 substituents chosen from:

(a) halogen atoms (for example, fluorine atoms); and (b) optionally halogenated $C_{1-6}$ alkyl groups (for example, methyl or difluoromethyl);

(3) mono- or di-$C_{1-6}$ alkylamino groups (for example, methylamino or dimethylamino) optionally substituted with 1 to 3 $C_{3-10}$ cycloalkyl groups (for example, cyclobutyl) optionally substituted with 1 to 3 halogen atoms (for example, fluorine atoms); and (4) 3- to 14-membered non-aromatic heterocyclic oxy groups (for example, 3- to 8-membered monocyclic non-aromatic heterocyclic oxy groups (for example, tetrahydropyranyloxy)).

In some embodiments, $R^4$ is chosen from:

(1) phenyl groups optionally substituted with 1 to 3 halogen atoms (for example, fluorine atoms);

(2) morpholinyl groups optionally substituted with 1 to 3 optionally halogenated $C_{1-6}$ alkyl groups (for example, methyl or difluoromethyl);

(3) piperidyl groups optionally substituted with 1 to 3 halogen atoms (for example, fluorine atoms);

(4) mono- or di-$C_{1-6}$ alkylamino groups (for example, methylamino or dimethylamino) optionally substituted with 1 to 3 $C_{3-6}$ cycloalkyl groups (for example, cyclobutyl) optionally substituted with 1 to 3 halogen atoms (for example, fluorine atoms); and (5) a tetrahydropyranyloxy group.

In some embodiments, $R^{4a}$ is chosen from morpholinyl groups optionally substituted with 1 to 3 $C_{1-6}$ alkyl groups (for example, methyl).

In some embodiments, $R^{4'}$ is chosen from morpholinyl groups substituted with one $C_{1-6}$ alkyl group (for example, methyl).

In some embodiments, the group represented by:

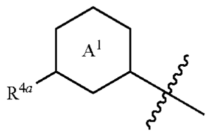

is chosen from:

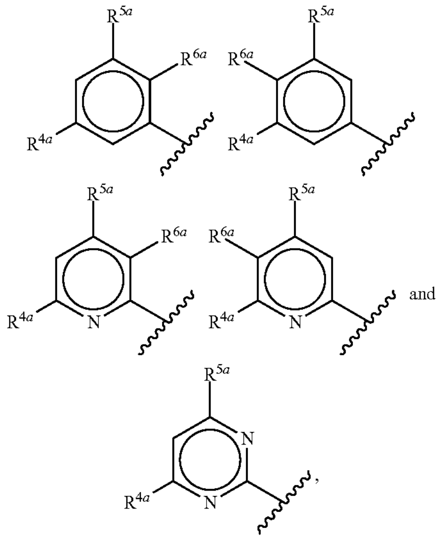

and , wherein $R^{5a}$ and $R^{6a}$ are independently chosen from a hydrogen atom and substituents, and other symbols are as defined above.

In some embodiments, $R^{5a}$ is chosen from:

(a) halogen atoms (for example, a bromine atom);

(b) optionally substituted $C_{1-6}$ alkyl groups (for example, methyl, ethyl, or isopropyl);

(c) optionally substituted $C_{1-6}$ alkoxy groups (for example, methoxy or ethoxy); and (d) optionally substituted $C_{3-10}$ cycloalkyl groups (for example, cyclopropyl).

In some embodiments, $R^{5a}$ is chosen from:

(a) halogen atoms (for example, a bromine atom);

(b) optionally halogenated $C_{1-6}$ alkyl groups (for example, isopropyl, difluoromethyl, trifluoromethyl, or 2,2,2-trifluoroethyl);

(c) optionally halogenated $C_{1-6}$ alkoxy groups (for example, trifluoromethoxy 2,2-difluoroethoxy, or 2,2,2-trifluoroethoxy); and (d) $C_{3-10}$ cycloalkyl groups (for example, cyclopropyl) optionally substituted with 1 to 3 halogen atoms (for example, fluorine atoms).

In some embodiments, $R^{5a}$ is chosen from:

(a) halogen atoms (for example, a bromine atom);

(b) optionally halogenated $C_{1-6}$ alkyl groups (for example, isopropyl, difluoromethyl, trifluoromethyl, or 2,2,2-trifluoroethyl);

(c) optionally halogenated $C_{1-6}$ alkoxy groups (for example, trifluoromethoxy 2,2-difluoroethoxy, or 2,2,2-trifluoroethoxy); and (d) $C_{3-6}$ cycloalkyl groups (for example, cyclopropyl) optionally substituted with 1 to 3 halogen atoms (for example, fluorine atoms).

In some embodiments, $R^{5a}$ is chosen from:

(a) $C_{1-6}$ alkyl groups (for example, isopropyl); and (b) $C_{3-6}$ cycloalkyl groups (for example, cyclopropyl).

In some embodiments, $R^{5a}$ is chosen from $C_3$, cycloalkyl groups (for example, cyclopropyl).

In some embodiments, $R^{5a}$ is a cyclopropyl group.

In some embodiments, $R^{6a}$ is chosen from:

(a) a hydrogen atom;

(b) a cyano group;

(c) halogen atoms (for example, a fluorine atom); and (d) optionally substituted $C_{1-6}$ alkyl groups (for example, methyl).

In some embodiments, $R^6$, is chosen from:

(a) a hydrogen atom;

(b) a cyano group;

(a) halogen atoms (for example, a fluorine atom); and (d) $C_{1-6}$ alkyl groups (for example, methyl).

In some embodiments, $R^{6a}$ is chosen from halogen atoms (for example, a fluorine atom). In some embodiments, $R^6$, is a fluorine atom.

In some embodiments, the group represented by:

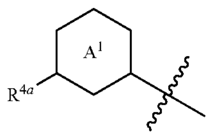

is chosen from:

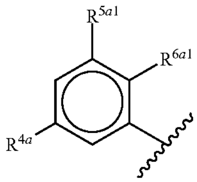

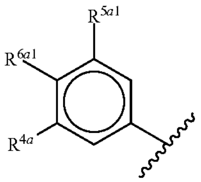

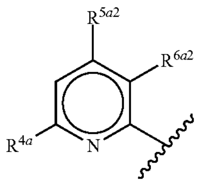

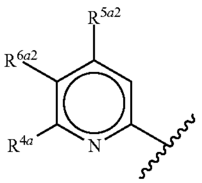

and

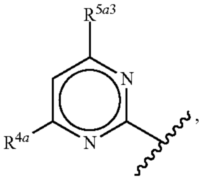

wherein $R^{5a1}$, $R^{5a2}$, $R^{5a3}$, $R^{6a1}$, and $R^{6a2}$ are each independently chosen from a hydrogen atom and substituents, and other symbols are as defined above.

In some embodiments, $R^{5a1}$ is chosen from:

(a) halogen atoms (for example, a bromine atom);

(b) optionally halogenated $C_{1-6}$ alkyl groups (for example, isopropyl, trifluoromethyl, or 2,2,2-trifluoroethyl);

(c) optionally halogenated $C_{1-6}$ alkoxy groups (for example, trifluoromethoxy); and (d) $C_{3-10}$ cycloalkyl groups (for example, cyclopropyl) optionally substituted with 1 to 3 halogen atoms (for example, fluorine atoms).

In some embodiments, $R^{5a1}$ is chosen from:

(a) halogen atoms (for example, a bromine atom);

(b) optionally halogenated $C_{1-6}$ alkyl groups (for example, isopropyl, trifluoromethyl, or 2,2,2-trifluoroethyl);

(c) optionally halogenated $C_{1-6}$ alkoxy groups (for example, trifluoromethoxy); and (d) $C_{3-10}$ cycloalkyl groups (for example, cyclopropyl) optionally substituted with 1 to 3 halogen atoms (for example, fluorine atoms).

In some embodiments, $R^{5a1}$ is chosen from:

(a) $C_{1-6}$ alkyl groups (for example, isopropyl); and (b) $C_{3-6}$ cycloalkyl groups (for example, cyclopropyl).

In some embodiments, $R^{5a1}$ is chosen from $C_{3-6}$ cycloalkyl groups (for example, cyclopropyl). In some embodiments, $R^{5a1}$ is a cyclopropyl group.

In some embodiments, $R^{5a2}$ is chosen from:

(a) optionally halogenated $C_{1-6}$ alkyl groups (for example, difluoromethyl or trifluoromethyl); and (b) optionally halogenated $C_{1-6}$ alkoxy groups (for example, 2,2-difluoroethoxy or 2,2,2-trifluoroethoxy).

In some embodiments, $R^{6a1}$ is chosen from optionally halogenated $C_{1-6}$ alkyl groups (for example, trifluoromethyl) .

In some embodiments, $R^{6a1}$ is chosen from a hydrogen atom and halogen atoms (for example, a fluorine atom).

In some embodiments, $R^{6a1}$ is chosen from halogen atoms (for example, a fluorine atom). In some embodiments, $R^{6a1}$ is a fluorine atom.

In some embodiments, $R^{6a2}$ is chosen from:

(a) a hydrogen atom;

(b) a cyano group;

(c) halogen atoms (for example, a fluorine atom); and (d) $C_{1-6}$ alkyl groups (for example, methyl).

In some embodiments, the group represented by:

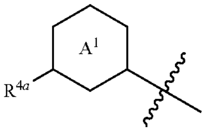

is chosen from:

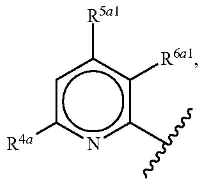

wherein the symbols in the formula are each as defined above.

In some embodiments, $R^{5a1}$ is chosen from:

(a) $C_{1-6}$ alkyl groups (for example, isopropyl); and (b) $C_{3-6}$ cycloalkyl groups (for example, cyclopropyl).

In some embodiments, $R^{5a1}$ is chosen from $C_{3-6}$ cycloalkyl groups (for example, cyclopropyl). In some embodiments, $R^{5a1}$ is a cyclopropyl group.

In some embodiments, $R^{6a1}$ is chosen from halogen atoms (for example, a fluorine atom). In some embodiments, $R^{6a1}$ is a fluorine atom.

Non-limiting examples of substituents in the "optionally further substituted 5-membered monocyclic aromatic heterocyclic ring" represented by ring $A^2$ are substituents chosen from substituent group A. In some embodiments, the number of these optional substituents is from 1 to 3. When the number of optional substituents is 2 or greater, the respective optional substituents may be the same or different from one another.

In some embodiments, ring B is chosen from pyridone rings optionally further substituted with 1 to 3 substituents chosen from:

(1) halogen atoms (for example, fluorine atoms); and (2) optionally substituted $C_{1-6}$ alkyl groups (for example, methyl).

Non-limiting examples of substituents in the "optionally substituted $C_{1-6}$ alkyl group" described above are substituents chosen from substituent group A. In some embodiments, the number of these optional substituents is from 1 to 3. When the number of optional substituents is 2 or greater, the respective optional substituents may be the same or different from one another.

In some embodiments, ring B is chosen from pyridone rings optionally further substituted with 1 to 3 substituents chosen from:

(1) halogen atoms (for example, fluorine atoms); and (2) $C_{1-6}$ alkyl groups (for example, methyl).

In some embodiments, ring B is chosen from pyridone rings optionally further substituted with one substituent chosen from:

(1) halogen atoms (for example, fluorine atoms); and (2) $C_{1-6}$ alkyl groups (for example, methyl).

In some embodiments, ring B is a pyridone ring having no additional substituents.

In some embodiments, $R^2$ and $R^3$ are each independently chosen from a hydrogen atom and substituents.

In some embodiments, $R^2$ and $R^3$ are both hydrogen atoms.

In some embodiments, ring C is chosen from optionally further substituted 5-membered monocyclic aromatic heterocyclic rings.

In some embodiments, the "5-membered monocyclic aromatic heterocyclic group" of the "optionally further substituted 5-membered monocyclic aromatic heterocyclic group" represented by ring C is pyrazole (for example, 1H-pyrazole-4-yl).

Non-limiting examples of optional substituents in the "optionally further substituted 5-membered monocyclic aromatic heterocyclic ring" represented by ring C are substituents chosen from substituent group A. In some embodiments, the number of these optional substituents is from 1 to 3. When the number of optional substituents is 2 or greater, the respective optional substituents may be the same or different from one another.

In some embodiments, ring C is chosen from 5-membered monocyclic aromatic heterocyclic rings (for example, pyrazole) optionally further substituted with 1 to 3 $C_{1-6}$ alkyl groups (for example, ethyl or isopropyl). In some embodiments, ring C is chosen from pyrazole rings (for example, 1H-pyrazole-4-yl) optionally further substituted with 1 to 3 (for example, 1) $C_{1-6}$ alkyl groups (for example, ethyl or isopropyl). In some embodiments, ring C is chosen from pyrazole rings (for example, 1H-pyrazole-4-yl) further substituted with one $C_{1-6}$ alkyl group (for example, ethyl).

In some embodiments, ring C is chosen from optionally further substituted pyrazole groups.

In some embodiments, ring C is chosen from further substituted pyrazole rings.

In some embodiments, ring C is chosen from cyclic groups represented by the formula:

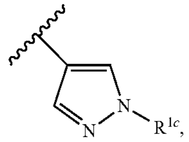

wherein $R^{1c}$ is chosen from a hydrogen atom and $C_{1-6}$ alkyl groups (for example, ethyl or isopropyl, for example, ethyl)).

In some embodiments, RIC is chosen from $C_{1-6}$ alkyl groups (for example, ethyl or isopropyl, for example, ethyl).

Also disclosed herein is a compound (also referred to herein as Compound A) chosen from compounds of Formula (IA):

(IA)

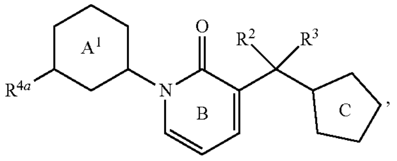

and pharmaceutically acceptable salts thereof, wherein:

ring $A^1$ is chosen from optionally further substituted 6-membered aromatic rings (for example, benzene, pyridine, or pyrimidine);

$R^{4a}$ is chosen from optionally substituted $C_{6-14}$ aryl groups (for example, phenyl), optionally substituted 3- to 14-membered non-aromatic heterocyclic groups (for example, a 3- to 8-membered monocyclic non-aromatic heterocyclic group (for example, morpholinyl or piperidyl)), optionally substituted mono- or di-$C_{1-6}$ alkylamino groups (for example, methylamino or dimethylamino), and optionally substituted 3- to 14-membered non-aromatic heterocyclic oxy groups (for example, a 3- to 8-membered monocyclic non-aromatic heterocyclic oxy group (for example, tetrahydropyranyloxy));

ring B is chosen from pyridone groups optionally further substituted with 1 to 3 substituents chosen from halogen atoms (for example, fluorine atoms) and optionally substituted $C_{1-6}$ alkyl groups (for example, methyl);

$R^2$ and $R^3$ are each independently chosen from a hydrogen atom and optionally substituted $C_{1-6}$ alkyl groups (for example, methyl); and ring C is chosen from optionally further substituted 5-membered monocyclic aromatic heterocyclic rings (for example, pyrazole).

In some embodiments, ring $A^1$ is chosen from optionally further substituted benzene, optionally further substituted pyridine, and optionally further substituted pyrimidine. In some embodiments, ring $A^1$ is chosen from benzene, pyridine, and pyrimidine.

In some embodiments, $R^{4a}$ is optionally substituted phenyl. In some embodiments, $R^{4a}$ is phenyl.

In some embodiments, $R^{4a}$ is chosen from morpholinyl and piperidyl.

In some embodiments, $R^{4a}$ is chosen from methylamino and dimethylamino.

In some embodiments, $R^{4a}$ is chosen from 3- to 8-membered monocyclic non-aromatic heterocyclic oxy groups. In some embodiments, $R^{4a}$ is tetrahydropyranyloxy.

In some embodiments, ring B is chosen from pyridone groups optionally further substituted with 1 to 3 substituents independently chosen from fluorine and methyl.

In some embodiments, $R^2$ and $R^3$ are each independently chosen from a hydrogen atom and methyl.

In some embodiments, ring C is chosen from optionally further substituted pyrazole groups. In some embodiments, ring C is pyrazole.

Also disclosed herein is a compound (also referred to herein as Compound B) chosen from compounds of Formula (IB):

(IB)

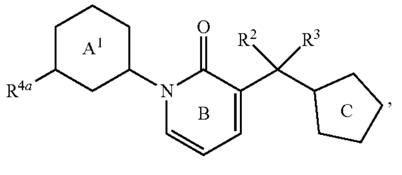

and pharmaceutically acceptable salts thereof, wherein:

- ring $A^1$ is chosen from benzene rings further substituted with 1 or 2 substituents independently chosen from halogen atoms (for example, fluorine atoms or bromine atoms), cyano groups, optionally halogenated $C_{1-6}$ alkyl groups (for example, methyl, isopropyl, difluoromethyl, trifluoromethyl, or 2,2,2-trifluoroethyl), optionally halogenated $C_{1-6}$ alkoxy groups (for example, trifluoromethoxy, 2,2-difluoroethoxy, or 2,2,2-trifluoroethoxy), and $C_{3-10}$ cycloalkyl group (for example, cyclopropyl) optionally substituted with 1 to 3 halogen atoms (for example, fluorine atoms);
- $R^{4a}$ is chosen from $C_{6-14}$ aryl groups (for example, phenyl) optionally substituted with 1 to 3 substituents independently chosen from halogen atoms (for example, fluorine atoms), 3- to 14-membered non-aromatic heterocyclic groups (for example, a 3- to 8-membered monocyclic non-aromatic heterocyclic group (for example, morpholinyl or piperidyl)) optionally substituted with 1 to 3 substituents independently chosen from halogen atoms (for example, fluorine atoms), optionally halogenated $C_{1-6}$ alkyl groups (for example, methyl or difluoromethyl), mono- or di-$C_{1-6}$ alkylamino groups (for example, methylamino or dimethylamino) optionally substituted with 1 to 3 substituents independently chosen from $C_{3-10}$ cycloalkyl groups (for example, cyclobutyl) optionally substituted with 1 to 3 substituents independently chosen from halogen atoms (for example, fluorine atoms), and 3- to 14-membered non-aromatic heterocyclic oxy groups (for example, a 3- to 8-membered monocyclic non-aromatic heterocyclic oxy group (for example, tetrahydropyranyloxy)); and
- all other symbols are as defined in an embodiment above.

In some embodiments, ring $A^1$ is chosen from benzene rings further substituted with 1 or 2 substituents independently chosen from fluorine, bromine, methyl, isopropyl, difluoromethyl, trifluoromethyl, 2,2,2-trifluoroethyl, trifluoromethoxy, 2,2-difluoroethoxy, 2,2,2-trifluoroethoxy, and cyclopropyl optionally substituted with 1 to 3 fluorine atoms.

In some embodiments, $R^{4a}$ is chosen from phenyl optionally substituted with 1 to 3 fluorine atoms.

In some embodiments, $R^{4a}$ is chosen from phenyl optionally substituted with 1 to 3 fluorine atoms.

In some embodiments, $R^{4a}$ is chosen from morpholinyl and piperidyl.

In some embodiments,

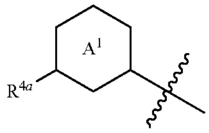

is chosen from:

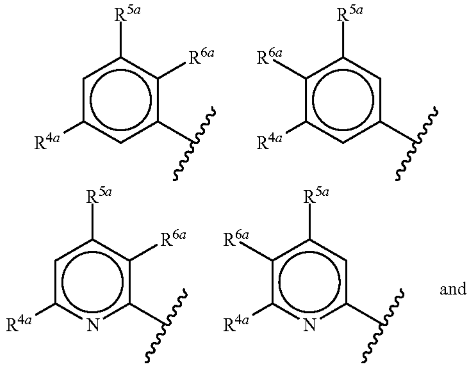

and

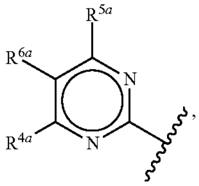

, wherein:

- $R^{4a}$ is as defined in an embodiment above;
- $R^{5a}$ is chosen from halogen atoms (for example, a bromine atom), optionally halogenated $C_{1-6}$ alkyl groups (for example, isopropyl, difluoromethyl, trifluoromethyl, or 2,2,2-trifluoroethyl); optionally halogenated $C_{1-6}$ alkoxy groups (for example, trifluoromethoxy 2,2-difluoroethoxy, or 2,2,2-trifluoroethoxy), and $C_{3-10}$ cycloalkyl groups (for example, cyclopropyl) optionally substituted with 1 to 3 substituents independently chosen from halogen atoms (for example, fluorine atoms); and
- $R^{6a}$ is chosen from a hydrogen atom, a cyano group, halogen atoms (for example, a fluorine atom); and $C_{1-6}$ alkyl groups (for example, methyl);
- ring B is chosen from pyridone groups optionally further substituted with 1 to 3 substituents independently chosen from halogen atoms (for example, fluorine atoms) and $C_{1-6}$ alkyl groups (for example, methyl);
- $R^2$ and $R^3$ are both hydrogen atoms; and
- ring C is chosen from 5-membered monocyclic aromatic heterocyclic rings (for example, pyrazole) optionally further substituted with 1 to 3 substituents independently chosen from $C_{1-6}$ alkyl groups (for example, ethyl or isopropyl).

Also disclosed herein is a compound (also referred to herein as Compound C) chosen from compounds of Formula (IC):

(IC)

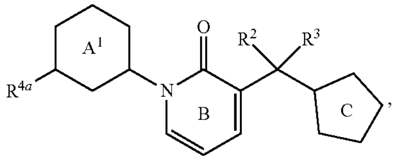

and pharmaceutically acceptable salts thereof, wherein:

ring $A^1$ is chosen from benzene rings further substituted with 1 or 2 substituents independently chosen from:

(1) benzene rings optionally further substituted with 1 to 3 substituents independently from:

(a) halogen atoms (for example, fluorine atoms or bromine atoms); and (b) optionally halogenated $C_{1-6}$ alkyl groups (for example, isopropyl, trifluoromethyl, or 2,2,2-trifluoroethyl);

(c) optionally halogenated $C_{1-6}$ alkoxy groups (for example, trifluoromethoxy); and (d) $C_{3-10}$ cycloalkyl groups (for example, cyclopropyl) optionally substituted with 1 to 3 substituents independently chosen from halogen atoms (for example, fluorine atoms);

(2) pyridine rings optionally further substituted with 1 to 3 substituents independently chosen from:

(a) halogen atoms (for example, fluorine atoms);

(b) a cyano group;

(c) optionally halogenated $C_{1-6}$ alkyl groups (for example, methyl, difluoromethyl, or trifluoromethyl); and (d) optionally halogenated $C_{1-6}$ alkoxy groups (for example, 2,2-difluoroethoxy or 2,2,2-trifluoroethoxy); and (3) pyrimidine rings optionally further substituted with 1 or 2 substituents independently chosen from optionally halogenated $C_{1-6}$ alkyl groups (for example, trifluoromethyl); $R^{4a}$ is chosen from:

(1) $C_{6-14}$ aryl groups (for example, phenyl) optionally substituted with 1 to 3 substituents independently chosen from halogen atoms (for example, fluorine atoms);

(2) 3- to 14-membered non-aromatic heterocyclic groups (for example, 3- to 8-membered monocyclic non-aromatic heterocyclic groups (for example, morpholinyl or piperidyl)) optionally substituted with 1 to 3 substituents independently chosen from:

(a) halogen atoms (for example, fluorine atoms); and (b) optionally halogenated $C_{1-6}$ alkyl groups (for example, methyl or difluoromethyl);

(3) mono- or di-$C_{1-6}$ alkylamino groups (for example, methylamino or dimethylamino) optionally substituted with 1 to 3 substituents independently chosen from $C_{3-10}$ cycloalkyl groups (for example, cyclobutyl) optionally substituted with 1 to 3 substituents independently chosen from halogen atoms (for example, fluorine atoms); and (4) 3- to 14-membered non-aromatic heterocyclic oxy groups (for example, 3- to 8-membered monocyclic non-aromatic heterocyclic oxy groups (for example, tetrahydropyranyloxy)).

In some embodiments,

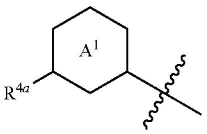

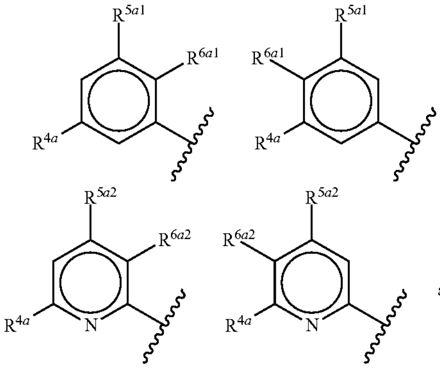

and

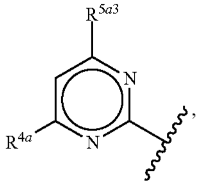

wherein:

(a) is as defined above;

$R^{5a1}$ is chosen from:

(a) halogen atoms (for example, a bromine atom);

(b) optionally halogenated $C_{1-6}$ alkyl groups (for example, isopropyl, trifluoromethyl, or 2,2,2-trifluoroethyl);

(c) optionally halogenated $C_{1-6}$ alkoxy groups (for example, trifluoromethoxy); and (d) $C_{3-10}$ cycloalkyl groups (for example, cyclopropyl) optionally substituted with 1 to 3 halogen atoms (for example, fluorine atoms);

$R^{5a1}$ is chosen from:

(a) optionally halogenated $C_{1-6}$ alkyl groups (for example, difluoromethyl or trifluoromethyl); and (b) optionally halogenated $C_{1-6}$ alkoxy groups (for example, 2,2-difluoroethoxy or 2,2,2-trifluoroethoxy);

$R^{5a3}$ is chosen from optionally halogenated $C_{1-6}$ alkyl groups (for example, trifluoromethyl);

$R^{6a1}$ at is chosen from a hydrogen atom and halogen atoms (for example, a fluorine atom); and $R^{6a2}$ is chosen from:

(a) a hydrogen atom;

(b) a cyano group;

(c) halogen atoms (for example, a fluorine atom); and (d) $C_{1-6}$ alkyl groups (for example, methyl);

ring B is chosen from pyridone rings optionally further substituted with 1 to 3 substituents independently chosen from:

(1) halogen atoms (for example, fluorine atoms); and (2) $C_{1-6}$ alkyl groups (for example, methyl);

$R^2$ and $R^3$ are both hydrogen atoms; and ring C is chosen from pyrazole rings (for example, 1H-pyrazole-4-yl) optionally further substituted with 1 to 3 (for example, 1) substituents independently chosen from $C_{1-6}$ alkyl groups (for example, ethyl or isopropyl).

In some embodiments, ring C is:

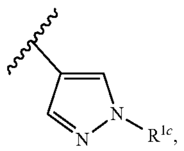

wherein $R^{1C}$ is chosen from a hydrogen atom and $C_{1-6}$ alkyl groups (for example, ethyl or isopropyl).

Also disclosed herein is a compound (also referred to herein as Compound D) chosen from compounds of Formula (ID):

(ID)

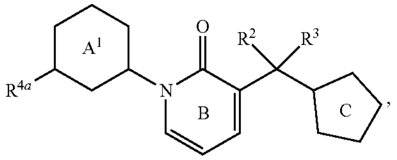

and pharmaceutically acceptable salts thereof, wherein:

ring $A^1$ is a benzene ring further substituted with 1 or 2 substituents independently chosen from:

(1) benzene rings optionally further substituted with 1 to 3 substituents independently from:
  (a) halogen atoms (for example, fluorine atoms or bromine atoms);
  (b) optionally halogenated $C_{1-6}$ alkyl groups (for example, isopropyl, trifluoromethyl, or 2,2,2-trifluoroethyl);
  (c) optionally halogenated $C_{1-6}$ alkoxy groups (for example, trifluoromethoxy); and
  (d) $C_{3-6}$ cycloalkyl groups (for example, cyclopropyl) optionally substituted with 1 to 3 substituents independently chosen from halogen atoms (for example, fluorine atoms);

(2) pyridine rings optionally further substituted with 1 to 3 substituents independently chosen from:
  (a) halogen atoms (for example, fluorine atoms);
  (b) cyano groups;
  (c) optionally halogenated $C_{1-6}$ alkyl groups (for example, methyl, difluoromethyl, or trifluoromethyl); and
  (d) optionally halogenated $C_{1-6}$ alkoxy groups (for example, 2,2-difluoroethoxy or 2,2,2-trifluoroethoxy); and (3) pyrimidine rings optionally further substituted with 1 or 2 substituents independently chosen from optionally halogenated $C_{1-6}$ alkyl groups (for example, trifluoromethyl); $R^{4a}$ is chosen from:

(1) phenyl groups optionally substituted with 1 to 3 substituents independently chosen from halogen atoms (for example, fluorine atoms);

(2) morpholinyl groups optionally substituted with 1 to 3 substituents independently chosen from optionally halogenated $C_{1-6}$ alkyl groups (for example, methyl or difluoromethyl);

(3) piperidyl groups optionally substituted with 1 to 3 substituents independently chosen from halogen atoms (for example, fluorine atoms);

(4) mono- or di-$C_{1-6}$ alkylamino groups (for example, methylamino or dimethylamino) optionally substituted with 1 to 3 substituents independently chosen from $C_{3-6}$ cycloalkyl groups (for example, cyclobutyl) optionally substituted with 1 to 3 substituents independently chosen from halogen atoms (for example, fluorine atoms); and (5) a tetrahydropyranyloxy group.

In some embodiments,

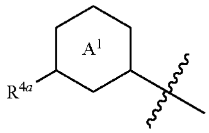

is chosen from:

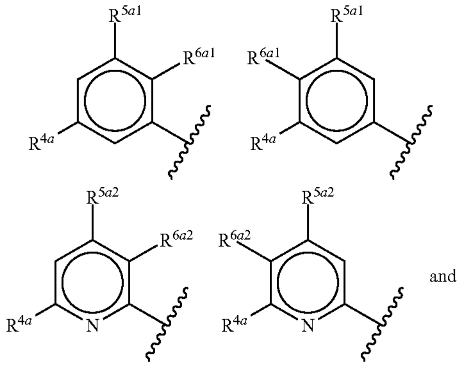

and

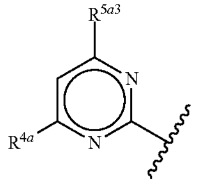

wherein $R^{4a}$ is as defined above;

$R^{5a}$ is chosen from:

(a) halogen atoms (for example, a bromine atom);
(b) optionally halogenated $C_{1-6}$ alkyl groups (for example, isopropyl, trifluoromethyl, or 2,2,2-trifluoroethyl);
(c) optionally halogenated $C_{1-6}$ alkoxy groups (for example, trifluoromethoxy); and
(d) $C_{3-10}$ cycloalkyl groups (for example, cyclopropyl) optionally substituted with 1 to 3 substituents independently chosen from halogen atoms (for example, fluorine atoms);

$R^{5a2}$ is chosen from:

(a) optionally halogenated $C_{1-6}$ alkyl groups (for example, difluoromethyl or trifluoromethyl); and
(b) optionally halogenated $C_{1-6}$ alkoxy groups (for example, 2,2-difluoroethoxy or 2,2,2-trifluoroethoxy);

$R^{5a3}$ is chosen from optionally halogenated $C_{1-6}$ alkyl groups (for example, trifluoromethyl);

$R^{6a1}$ is chosen from a hydrogen atom and halogen atoms (for example, a fluorine atom); and $R^6$ is chosen from:

(a) a hydrogen atom;

(b) a cyano group;

(c) halogen atoms (for example, a fluorine atom); and (d) $C_{1-6}$ alkyl groups (for example, methyl);

ring B is chosen from pyridone groups optionally further substituted with 1 to 3 substituents independently chosen from:

(1) halogen atoms (for example, fluorine atoms); and (2) $C_{1-6}$ alkyl groups (for example, methyl);

$R^2$ and $R^3$ are both hydrogen atoms; and ring C is chosen from pyrazole rings (for example, 1H-pyrazole-4-yl) optionally further substituted with 1 to 3 (for example, 1) substituents chosen from $C_{1-6}$ alkyl groups (for example, ethyl or isopropyl).

In some embodiments, ring C is

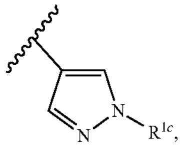

wherein $R^{1c}$ is chosen from a hydrogen atom and $C_{1-6}$ alkyl groups (for example, ethyl or isopropyl).

Also disclosed herein is a compound (also referred to herein as Compound E) chosen from compounds of Formula (IE):

(IE)

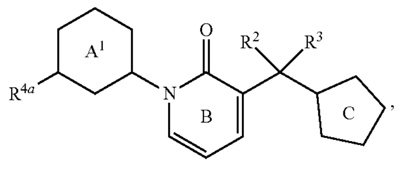

and pharmaceutically acceptable salts thereof, wherein:

ring $A^1$ is chosen from benzene rings further substituted with 1 or 2 substituents independently chosen from:

(a) halogen atoms (for example, fluorine atoms);

(b) $C_{1-6}$ alkyl groups (for example, isopropyl); and (c) $C_3$—, cycloalkyl groups (for example, cyclopropyl);

$R^{4a}$ is chosen from morpholinyl groups optionally substituted with 1 to 3 substituents independently chosen from $C_{1-6}$ alkyl groups (for example, methyl);

ring B is a pyridone ring having no additional substituents:

$R^2$ and $R^3$ are both hydrogen atoms; and ring C is chosen from pyrazole rings (for example, 1H-pyrazole-4-yl) further substituted with one $C_{1-6}$ alkyl group (for example, ethyl).

In some embodiments,

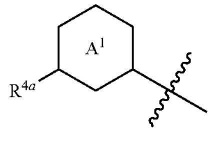

is a group represented b the formula:

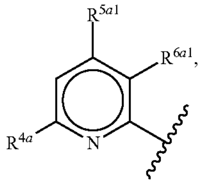

wherein:

$R^{4a}$ is as defined above;

$R^{5a1}$ is chosen from:

(a) $C_{1-6}$ alkyl groups (for example, isopropyl); and (b) $C_{3-6}$ cycloalkyl groups (for example, cyclopropyl); and $R^{6a1}$ is a halogen atom (for example, a fluorine atom).

In some embodiments, ring C is:

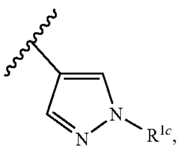

wherein $R^{1c}$ is chosen from $C_{1-6}$ alkyl groups (for example, ethyl).

Also disclosed herein is a compound (also referred to herein as Compound F) chosen from compounds of Formula (IF):

(IF)

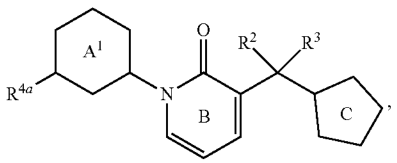

and pharmaceutically acceptable salts thereof, wherein:

ring $A^1$ is chosen from benzene rings further substituted with 1 or 2 substituents independently chosen from:

(a) halogen atoms (for example, fluorine atoms); and (b) $C_{3-6}$ cycloalkyl groups (for example, cyclopropyl);

$R^{4a}$ is chosen from morpholinyl groups substituted with one $C_{1-6}$ alkyl group (for example, methyl);

ring B is a pyridone ring having no additional substituents;

$R^2$ and $R^3$ are both hydrogen atoms; and ring C is chosen from pyrazole rings (for example, 1H-pyrazole-4-yl) further substituted with one $C_{1-6}$ alkyl group (for example, ethyl).

In some embodiments, ring C is:

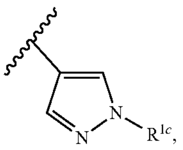

wherein $R^{1c}$ is chosen from $C_{1-6}$ alkyl groups (for example, ethyl).

In some embodiments,

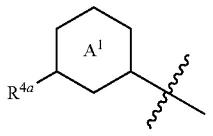

is a group represented by the formula:

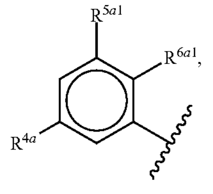

wherein:

$R^{4a}$ is as defined above;

$R^{5a1}$ is chosen from $C_{3-6}$ cycloalkyl groups (for example, cyclopropyl); and $R^{6a1}$ is chosen from halogen atoms (for example, a fluorine atom).

Compounds of Formula (I) include, but are not limited to, the compounds of Examples 1 to 33.

When Compound (I) is a salt, such as a pharmaceutically acceptable salt, non-limiting examples of such a salt include metal salts, ammonium salts, salts with organic bases, salts with inorganic acids, salts with organic acids, and salts with basic or acidic amino acids. Illustratively, non-limiting examples of metal salts include alkali metal salts such as sodium salts and potassium salts; alkali earth metal salts such as calcium salts, magnesium salts, and barium salts; and aluminum salts. Non-limiting examples of salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine, and the like. Non-limiting examples of salts with inorganic acids include salts with hydrochloric acid, hydrobromic acid, nitric acid, phosphoric acid, and the like. Non-limiting examples of salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, and the like. Non-limiting examples of salts with basic amino acids include salts with arginine, lysine, ornithine, and the like. Non-limiting examples of salts with acidic amino acids include salts with aspartic acid, glutamic acid, and the like. For example, when a compound of the present disclosure contains acidic functional groups, inorganic salts such as alkali metal salts (for example, sodium salts, potassium salts, or the like) or alkali earth metal salts (for example, calcium salts, magnesium salts, barium salts, or the like), ammonium salts, or the like may be used. Additionally, when the compound contains basic functional groups, salts with inorganic acids such as hydrochloric acid, hydrobromic acid, nitric acid, sulfuric acid, or phosphoric acid or salts with organic acids such as acetic acid, phthalic acid, fumaric acid, oxalic acid, tartaric acid, maleic acid, citric acid succinic acid, methanesulfonic acid or p-toluenesulfonic acid may be used.

When Compound (I) contains an isomer, such as a tautomer, an enantiomer, a stereoisomer, a regioisomer, or a rotamer, any one of the isomers and mixtures thereof are also included in Compound (I). Further, when there is an enantiomer in Compound (I), an enantiomer split from a racemic body is also included in Compound (I).

In some embodiments, Compound (I) may be a crystal; accordingly, a single crystal form and a mixed crystal form are included in Compound (I).

In some embodiments, Compound (I) may be a pharmaceutically acceptable cocrystal or cocrystal salt. As used herein, a cocrystal or cocrystal salt refers to a crystalline substance comprising two or more unique solids at room temperature, each of which has different physical characteristics (for example, structure, melting point, heat of fusion, hygroscopicity, solubility, stability, and the like). A cocrystal or cocrystal salt may be produced in accordance with a known co-crystallization method.

In some embodiments, Compound (1) may be a solvate (for example, a hydrate or the like) or a solvent-free substance, and both of these are included in Compound (I).

In some embodiments, compounds labeled or substituted with isotopes (for example, $^{2}H$, $^{3}H$, $^{11}C$, $^{14}C$, $^{18}F$, $^{35}S$, $^{125}I$, or the like) are also included in Compound (I). For example, in some embodiments, a compound labeled or substituted with an isotope can be used as a tracer (PET tracer) for Positron Emission Tomography (PET). In some embodiments, a compound labeled or substituted with an isotope may be useful in fields such as medical diagnosis.

A method for producing a compound of the present disclosure will be described hereinafter.

The starting materials or reagents used in each step of the following production methods and the resulting compounds may respectively form salts. Examples of such salts include the same salts as those of a compound of the present disclosure described above.

When the compound obtained in each step is a free form, it may be converted to a target salt using a method known per se. Conversely, when the compound obtained in each step is a salt, it can be converted to a free form or another type of target salt with a method known per se.

The compound obtained in each step can be used in the next reaction directly as a reaction solution or after it is isolated as a crude product. Alternatively, the compound obtained in each step can be isolated and/or purified from the reaction mixture with a separation means such as concentration, crystallization, recrystallization, distillation, solvent extraction, fractional distillation, or chromatography in accordance with conventional techniques.

When the starting materials or reagents in each step are commercially available, commercially available products can be used directly.

In the reaction of each step, the reaction time may vary based on the reagents or solvents that are used. However, unless specified otherwise, the reaction time is ordinarily from 1 minute to 48 hours, for example, from 10 minutes to 8 hours.

In the reaction of each step, the reaction temperature may vary based on the reagents or solvents that are used, but unless specified otherwise, the reaction temperature is ordinarily from −78° C. to 300° C., for example, from −78° C. to 150° C.

In the reaction of each step, the pressure may vary based on the reagents or solvents that are used, but unless specified otherwise, the pressure is ordinarily from 1 atm to 20 atm, for example, from 1 atm to 3 atm.

In the reaction of each step, for example, a microwave synthesizer such as an Initiator available from Biotage can be used. The reaction temperature may vary based on the reagents or solvents that are used, but unless specified otherwise, the reaction temperature is ordinarily from room temperature to 300° C., for example, from 50° C. to 250° C. The reaction time may vary based on the reagents or solvents that are used, but unless specified otherwise, the reaction time is ordinarily from 1 minute to 48 hours, for example, from 1 minute to 8 hours.

In the reaction of each step, unless specified otherwise, reagents are used in an amount of from 0.5 to 20 equivalents, for example, from 0.8 to 5 equivalents with respect to the substrate. When a reagent is used as a catalyst, the reagent is used in an amount of from 0.001 to 1 equivalent, for example, from 0.01 to 0.2 equivalents with respect to the substrate. When a reagent also serves as a reaction solvent, the reagent is used in a solvent amount.

In the reaction of each step, unless specified otherwise, the reactions are performed without a solvent or after dissolution or suspension in an appropriate solvent. Non-limiting examples of solvents are the solvents described in the Examples or those described below.

Alcohols: methanol, ethanol, tert-butyl alcohol, 2-methoxyethanol, and the like;

Ethers: diethyl ether, diphenyl ether, tetrahydrofuran, 1,2-dimethoxyethane, and the like;

Aromatic hydrocarbons: chlorobenzene, toluene, xylene, and the like;

Saturated hydrocarbons: cyclohexane, hexane, and the like;

Amides: N,N-dimethylformamide, N-methylpyrrolidone, and the like;

Halogenated hydrocarbons: dichloromethane, carbon tetrachloride, and the like;

Nitriles: acetonitrile and the like;

Sulfoxides: dimethylsulfoxide and the like;

Aromatic organic bases: pyridine and the like;

Acid anhydrides: acetic anhydride and the like;

Organic acids: formic acid, acetic acid, trifluoroacetic acid, and the like;

Inorganic acids: hydrochloric acid, sulfuric acid, and the like;

Esters: ethyl acetate and the like;

Ketones: acetone, methyl ethyl ketone, and the like;

Water.

In some embodiments, two or more types of the above solvents may be mixed in appropriate ratios and used in the described methods.

In some embodiments, when a base is used in the reaction of each step, the bases listed below or the bases described in the Examples may be used.

Inorganic bases: sodium hydroxide, magnesium hydroxide, sodium carbonate, calcium carbonate, sodium bicarbonate, and the like;

Organic bases: triethylamine, diethylamine, pyridine, 4-dimethylaminopyridine, N,N-dimethylaniline, 1,4-diazabicyclo[2. 2. 2]octane, 1,8-diazabicyclo[5. 4. 0]-7-undecene, imidazole, piperidine, and the like;

Metal oxides: sodium ethoxide, potassium tert-butoxide, and the like;

Alkali metal hydrides: sodium hydride and the like;

Metal amides: sodium amide, lithium diisopropylamide, lithium hexamethyldisilazide, and the like;

Organic lithiums: n-butyllithium and the like.

In some embodiments, when an acid or an acidic catalyst is used in the reaction of each step, the acids or acidic catalysts listed below or the acids or acidic catalysts described in the Examples may be used.

Inorganic acids: hydrochloric acid, sulfuric acid, nitric acid, hydrobromic acid, phosphoric acid, and the like;

Organic acids: acetic acid, trifluoroacetic acid, citric acid, p-toluenesulfonic acid, 10-camphorsulfonic acids, and the like;

Lewis acids: boron trifluoride diethyl ether complex; zinc iodide, anhydrous aluminum chloride, anhydrous zinc chloride, anhydrous iron chloride, and the like.

Unless specified otherwise, the reactions of each step may be performed in accordance with methods known per se—for example, the methods described in Experimental Chemistry, 5th Edition, Vol. 13-19 (edited by the Chemical Society of Japan); New Experimental Chemistry, Vol. 14-15 (edited by the Chemical Society of Japan); Fine Organic Chemistry, Revised 2nd Edition (L. F. Tietze, Th. Eicher, Nankodo Co., Ltd.); Revised Organic Named Reactions: Reaction Mechanism and Essence (by Hideo Togo, Kodansha); ORGANIC SYNTHESES Collective Volume I-VII (John Willey & Sons Inc.); Modern Organic Synthesis in the Laboratory, A Collection of Standard Experimental Procedures (by Jie Jack Li, published by OXFORD UNIVERSITY); Comprehensive Heterocyclic Chemistry III, Vol. 1 to Vol. 14 (Elsevier Japan KK); Strategic Applications of Named Reactions in Organic Synthesis (translation supervised by Kiyoshi Tomioka, published by Kagaku-Dojin Publishing); Comprehensive Organic Transformations (VCH Publishers Inc.), 1989 Edition, or the like—or in accordance with a method described in the Examples.

In each step, protection or deprotection reactions of functional groups are performed in accordance with methods known per se—for example, the methods described in Wiley-Interscience 2007 Edition "Protective Groups in Organic Synthesis, 4th Ed." (by Theodora W. Greene, Peter G. M. Wuts); Thieme 2004 Edition "Protecting Groups 3rd Ed." (by P. J. Kocienski) or the like—or in accordance with a method described in the Examples.

Non-limiting examples of protecting groups of hydroxyl groups such as alcohols or phenolic hydroxyl groups include ether-type protecting groups such as methoxymethyl ethers, benzyl ethers, tert-butyldimethylsilyl ethers, and tetrahydropyranyl ethers; carboxylic acid ester-type protecting groups such as acetic acid esters; sulfonic acid ester-type protecting groups such as methanesulfonic acid esters; and carbonic acid ester-type protecting groups such as tert-butylcarbonate.

Non-limiting examples of protecting groups of carbonyl groups of aldehydes include acetal-type protecting groups such as dimethylacetal; and cyclic acetal-type protecting groups such as 1,3-dioxane.

Non-limiting examples of protecting groups of carbonyl groups of ketones include ketal-type protecting groups such as dimethyl ketal; cyclic ketal-type protecting groups such as 1,3-dioxane; oxime-type protecting groups such as O-methyloxime; and hydrazone-type protecting groups such as N,N-dimethylhydrazone.

Non-limiting examples of protecting groups of carboxyl groups include ester-type protecting groups such as methyl ester; and amide-type protecting groups such as N,N-dimethylamide.

Non-limiting examples of protecting groups of thiols include ether-type protecting groups such as benzylthioethers; and ester-type protecting groups such as thioacetic acid esters, thiocarbonates, and thiocarbamates.

Non-limiting examples of protecting groups of amino groups or aromatic heterocycles such as imidazole, pyrrole, and indole include carbamate-type protecting groups such as benzylcarbamate; amide-type protecting groups such as acetamide; alkylamine-type protecting groups such as N-triphenylmethylamine; and sulfonamide-type protecting groups such as methanesulfonamide.

Protecting groups can be removed using a method known per se such as, for example, a method using an acid, a base, UV light, hydrazine, phenylhydrazine, sodium N-methyldithiocarbamate; tetrabutylammonium fluoride, palladium acetate, a trialkylsilyl hydride (for example, trimethylsilyl iodide or trimethylsilyl bromide), a reduction method, or the like.

When a reduction reaction is performed in a step, non-limiting examples of reducing agents that may be used include metal hydrides such as lithium aluminum hydride, sodium triacetoxyborohydride, sodium cyanoborohydride, diisobutylaluminum hydride (DIBAL-H), sodium borohydride, and tetramethylammonium triacetoxyborohydride; boranes such as borane tetrahydrofuran complexes; Raney nickel; Raney cobalt, hydrogen; formic acid; and triethylsilane. When reducing a carbon-carbon double bond or triple bond, there is a method of using a catalyst such as palladium-carbon or a Lindlar catalyst. When an oxidation reaction is performed in each step, examples of the oxidizing agent that is used include peracids such as m-chloroperbenzoic acid (mCPBA), hydrogen peroxide, and tert-butyl hydroperoxide; perchlorates such as tetrabutylammonium perchlorate; chlorites such as sodium chlorite; periodates such as sodium periodate, hypervalent iodine reagents such as iodosylbenzene; reagents containing manganese such as manganese dioxide and potassium permanganate; leads such as lead tetraacetate; reagents containing chromium such as pyridinium chlorochromate (PCC), pyridinium dichromate (PDC), and Jones reagent; halogen compounds such as N-bromosuccinimide (NBS); oxygen; ozone; sulfur trioxide-pyridine complex; osmium tetraoxide; selenium dioxide; and 2,3-dichloro-5,6-dicyano-1,4-benzoquinone (DDQ).

When a radical cyclization reaction is performed in a step, non-limiting examples of the radical initiator that may be used include azo compounds such as azobisisobutyronitrile (AIBN); water-soluble radical initiators such as 4-4'-azobis-4-cyanopentanoic acid (ACPA); triethyl boron in the presence of air or oxygen; and benzoyl peroxide. In addition, non-limiting examples of the radical reaction reagent that may be used include tributylstannane, tris-trimethylsilylsilane, 1,1,2,2-tetraphenyldisilane, diphenylsilane, and samarium diiodide.

When a Wittig reaction is performed in a step, non-limiting examples of the Wittig reagent that may be used include alkylidene phosphoranes. Alkylidene phosphoranes can be prepared by a method known per se, for example, by reacting a phosphonium salt and a strong base.

When a Horner-Emmons reaction is performed in a step, non-limiting examples of the reagent that may be used include phosphonoacetic acid esters such as methyl dimethylphosphonoacetate and ethyl diethylphosphonoacetate; and bases such as alkali metal hydrides and organic lithiums.

When a Friedel-Crafts reaction is performed in a step, non-limiting examples of the reagent that may be used include combinations of Lewis acids and acid chlorides or combinations of Lewis acids and alkylating agents (for example, alkyl halides, alcohols, olefins, and the like). Alternatively, an organic acid or an inorganic acid may also be used instead of a Lewis acid, and an acid anhydride such as acetic anhydride, may also be used instead of an acid chloride.

When an aromatic nucleophilic substitution reaction is performed in a step, a nucleophilic agent (for example, amines, 2-pyridone, imidazole, or the like) and a base (for example, organic or inorganic bases or the like) may be used as reagents When a carbanion-mediated nucleophilic addition reaction, a carbanion-mediated nucleophilic 1,4-addition reaction (Michael addition reaction), or a carbanion-mediated nucleophilic substitution reaction is performed in a step, non-limiting examples of a base used to generate a carbanion include organic lithiums, metal alkoxides, inorganic bases, and organic bases.

When a Grignard reaction is performed in a step, non-limiting examples of the Grignard reagent include arylmagnesium halides such as phenylmagnesium bromide; and alkylmagnesium halides such as methylmagnesium bromide. A Grignard reagent can be prepared with a method known per se such as, for example, by reacting an alkyl halide or an aryl halide with metallic magnesium using an ether or tetrahydrofuran as a solvent.

When a Knoevenagel reaction is performed in a step, an active methylene compound (for example, malonic acid, diethyl malonate, malononitrile, or the like) sandwiched between two electron-withdrawing groups and a base (for example, organic bases, metal oxides, or inorganic bases) may be used as reagents.

When a Vilsmeier-Haack reaction is performed in a step, phosphoryl chloride and an amide derivative (for example, N,N'-dimethylformamide or the like) may be used as reagents.

When an azidation reaction of alcohols, alkyl halides, and sulfonic acid esters is performed in a step, non-limiting examples of the azidation agent include diphenylphosphoryl azide (DPPA), trimethylsilyl azide, and sodium azide. For example, when azidating an alcohol, a method using diphenylphosphoryl azide and 1,8-diazabicyclo[5. 4. 0]undeca-7-ene (DBU) or a method using trimethylsilyl azide and a Lewis acid may be employed.

When a reductive amination reaction is performed in a step, non-limiting examples of the reducing agent that is used include sodium triacetoxyborohydride, sodium cyanoborohydride, sodium borohydride, hydrogen, and formic acid. When the substrate is an amine compound, non-limiting examples of the carbonyl compound that is used include paraformaldehyde, as well as aldehydes such as acetaldehyde and ketones such as cyclohexanone. When the substrate is a carbonyl compound, non-limiting examples of the amines to be used include primary amines such as ammonia and methylamine; and secondary amines such as dimethylamine.

When a Mitsunobu reaction is performed in a step, azodicarboxylic acid esters (for example, diethyl azodicarboxylate (DEAD), diisopropyl azodicarboxylate (DIAD), and the like) and triphenylphosphine are used as reagents. In addition, (cyanomethylene)tributylphosphorane (CMBP), (cyanomethylene)trimethylphosphorane (CMMP), or the like may also be used as a reagent.

When an esterification reaction, an amidation reaction, or a urea formation reaction is performed in a step, non-limiting examples of the reagent that is used include acyl halides such as acid chlorides and acid bromides; and activated carboxylic acids such as acid anhydrides, active esters, and sulfuric acid esters. Non-limiting examples of activators of carboxylic acids include carbodiimide-based condensing agents such as 1-ethyl-3-(3-dimethylaminopropyl)carbodiimide hydrochloride (WSCD); triazine-based condensing agents such as 4-(4,6-dimethoxy-1,3,5-triazine- 2-yl)-4-methylmorpholinium chloride-n-hydrate (DMT-MM); carbonic acid ester-based condensing agents such as 1,1-carbonyldiimidazole (CDI); benzotriazole-1-yloxy-tris-dimethylaminophosphonium salt (BOP reagent); 2-chloro-1-methyl-pyridinium iodide (Mukaiyama reagent); thionyl chloride; lower alkyl haloformates such as ethyl chloroformate; O-(7-azabenzotrazole-1-yl)-N,N,N',N'-tetramethyluronium hexafluorophosphate (HATU); sulfuric acid; or combinations thereof. When a carbodiimide-based condensing agent is used, additives such as 1-hydroxybenzotriazole (HOBt), N-hydroxysuccinimide (HOSu), and dimethylaminopyridine (DMAP) may be further added to the reaction.

When a coupling reaction is performed in a step, non-limiting examples of the metal catalyst that is used include palladium compounds such as palladium(II) acetate, tetrakis (triphenylphosphine) palladium(0), dichlorobis(triphenylphosphine) palladium(II), dichlorobis(triethylphosphine) palladium(II), tris(dibenzylideneacetone) dipalladium(0), and 1,1'-bis(diphenylphosphino) ferrocene palladium(II) chloride; nickel compounds such as tetrakis (triphenylphosphine) nickel(0); rhodium compounds such as tris(triphenylphosphine) rhodium(III) chloride; cobalt compounds; copper compounds such as copper oxide and copper (I) iodide; and platinum compounds. A base may be further added to the reaction, and non-limiting examples of such bases include inorganic bases.

When a thiocarbonylation reaction is performed in a step, diphosphorus pentasulfide is typically used as a thiocarbonylating agent; in addition to diphosphorus pentasulfide, reagents having a 1,3,2,4-dithiadiphosphetane-2,4-disulfide structure such as 2,4-bis(methoxyphenyl)-1,3,2,4-dithiadiphosphetane-2,4-disulfide (Lawesson reagent) may also be used.

When a Wohl-Ziegler reaction is used in a step, non-limiting examples of the halogenating reagent that is used include N-iodosuccinimide, N-bromosuccinimide (NBS), N-chlorosuccinimide (NCS), bromine, and sulfuryl chloride. Further, the reaction can be accelerated by adding heat, light, or a radical initiator such as benzoylperoxide or azobis isobutyronitrile to the reaction.

When a halogenation reaction of a hydroxy group is performed in a step, non-limiting examples of the halogenating agent that is used include acid halides of hydrohalic acids and inorganic acids; specifically, in the case of chlorination, hydrochloric acid, thionyl chloride, phosphorus oxychloride, or the like may be used, and in the case of bromination, 48% hydrobromic acid or the like may be used. In addition, a method of obtaining an alkyl halide from an alcohol by the action of triphenylphosphine and carbon tetrachloride or carbon tetrabromide may be used. Alternatively, a method of synthesizing an alkyl halide via a two-step reaction in which an alcohol is converted to a sulfonic acid ester and then reacted with lithium bromide, lithium chloride, or lithium iodide may be used.

When an Arbuzov reaction is performed in a step, non-limiting examples of the reagent that is used include alkyl halides such as ethyl bromoacetate; and phosphites such as triethylphosphite or tri(isopropyl)phosphite.

When a sulfonic acid esterification reaction is performed in a step, non-limiting examples of the sulfonylating agent that is used include methanesulfonyl chloride, p-toluenesulfonyl chloride, methanesulfonic anhydride, and p-toluenesulfonic acid anhydride.

When a hydrolysis reaction is performed in a step, an acid or a base may be used as a reagent. In addition, when an acid hydrolysis reaction of a tert-butyl ester is performed, formic acid, triethylsilane, or the like may be added to reductively trap the tert-butyl cations produced as a by-product.

When a dehydration reaction is performed in a step, non-limiting examples of the dehydrating agent that is used include sulfuric acid, diphosphorus pentasulfide, phosphorus oxychloride, N,N'-dicyclohexylcarbodiimide, alumina, and polyphosphoric acid.

Compound (I) can be produced in accordance with the reaction formulas illustrated below or methods conforming to these formulas. The starting materials may be commercially available products or may be produced using methods known per se. Unless specified otherwise, the abbreviations in each general formula in the reaction formula are as defined above.

For example, a compound of Formula (Ia) in which $R^1$ is

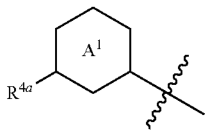

can be produced from compound (1) using the following method. In the formula, $L^1$ and $L^2$ are each independently a leaving group: $R^{101}$, $R^{12}$, and $R^{13}$ are each independently a hydrogen atom or a substituent; and other symbols are each as defined above.

Non-limiting examples of the "leaving group" indicated by $L^1$ or $L^2$ include halogen atoms, nitro groups, optionally halogenated $C_{1-6}$ alkylsulfonyloxy groups (for example, methanesulfonyloxy, ethanesulfonyloxy, or trifluoromethanesulfonyloxy), and $C_{6-14}$ arylsulfonyloxy groups (for example, benzenesulfonyloxy or toluenesulfonyloxy) optionally substituted with $C_{1-6}$ alkyl groups.

Non-limiting examples of the "substituents" indicated by $R^{101}$ include halogen atoms and optionally substituted alkyl groups. Examples of the "substituents" indicated by $R^{12}$ or $R^{13}$ include $C_{1-6}$ alkyl groups, and $R^{12}$ and $R^{13}$ may form an optionally further substituted ring together with the adjacent boron atoms (for example, $BOR^{12}OR^{13}$ is dimethoxyboranyl or 4,4,5,5-tetramethyl-1,3,2-dioxaborolane-2-yl).

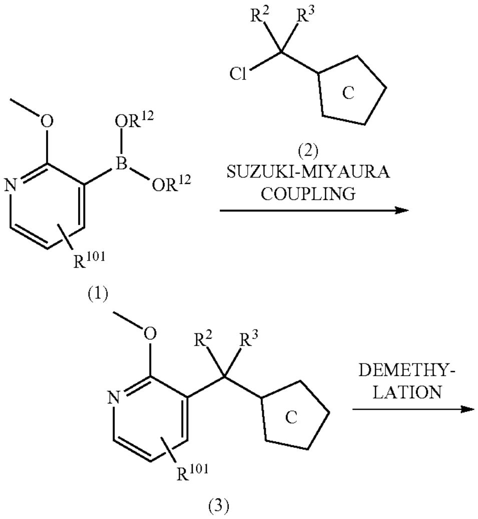

-continued

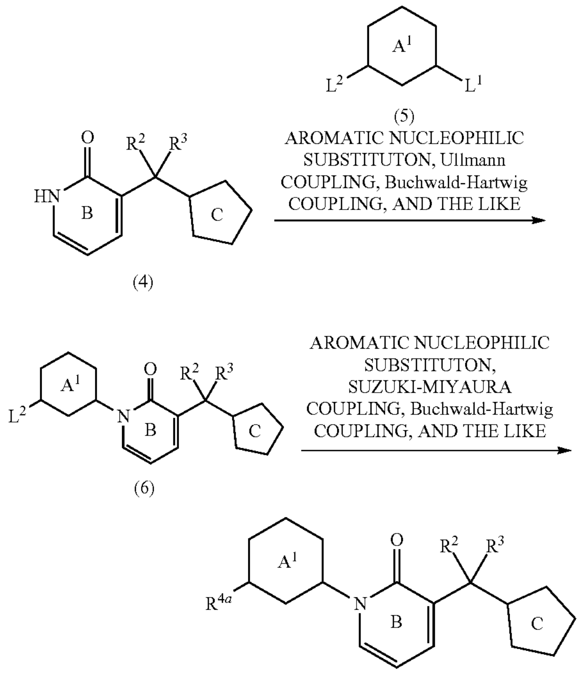

(4) (5) (6)

(Ia)

Compound (3) can be produced by a Suzuki-Miyaura coupling reaction between compound (1) and compound (2).

Compound (4) can be produced by a demethylation reaction of compound (3). Non-limiting examples of demethylation reagents include pyridine hydrochloride and the combination of trimethylsilyl chloride and sodium iodide. Non-limiting examples thereof include those listed in the "Removal of protecting groups" described above.

Compound (6) can be produced by various coupling reactions of compound (4) and compound (5) such as an aromatic nucleophilic substitution reaction, an Ullmann coupling reaction, or a Buchwald-Hartwig coupling reaction.

Compound (Ia) can be produced by various coupling reactions of compound (6) such as an aromatic nucleophilic substitution reaction, a Suzuki-Miyaura coupling reaction, or a Buchwald-Hartwig coupling reaction.

Compound (Ia) can be further transformed in accordance with a method known per se.

Compound (Ia) can also be produced from compound (5) using the following method. The symbols are each as defined above.

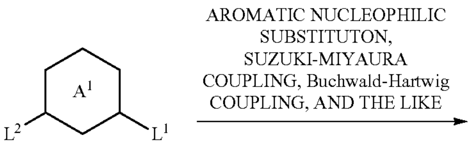

(5)

-continued

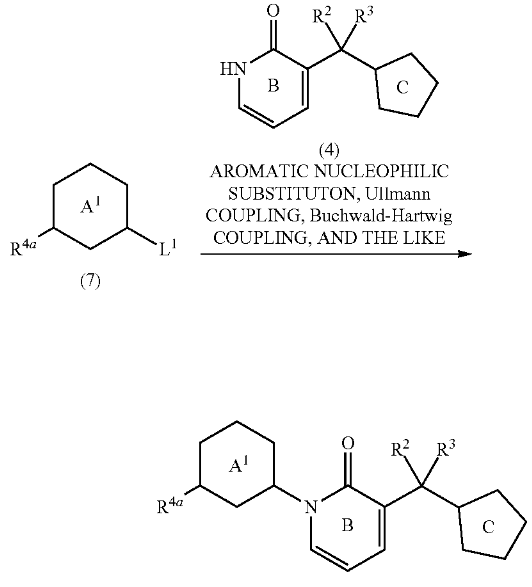

(4) (7)

(Ia)

Compound (7) can be produced from compound (5) using various coupling reactions, such as, for example, an aromatic nucleophilic substitution reaction, a Suzuki-Miyaura coupling reaction, or a Buchwald-Hartwig coupling reaction.

Compound (Ia) can be produced by various coupling reactions between compound (7) and compound (4), such as, for example, an aromatic nucleophilic substitution reaction, an Ullmann coupling reaction, or a Buchwald-Hartwig coupling reaction.

Compound (Ib), in which ring $A^1$ in compound (Ia) is a benzene ring having substituents $R^{14}$ and $R^{15}$, can be produced by a Chan-Lam-Evans coupling reaction between compound (8) and compound (4). In the formula, $R^{14}$, $R^{15}$, $R^{16}$, and $R^{17}$ are each independently a hydrogen atom or a substituent, and other symbols are as defined above.

Non-limiting examples of the substituents indicated by $R^{14}$ or $R^{15}$ include those listed as examples of the "substituents" of ring $A^1$. Examples of the "substituents" indicated by $R^{16}$ or $R^{17}$ include $C_{1-6}$ alkyl groups, and $R^{16}$ and $R^{17}$ may form an optionally further substituted ring together with the adjacent boron atoms (for example, $BOR^{16}OR^{17}$ is dimethoxyboranyl or 4,4,5,5-tetramethyl-1,3,2-dioxaborolane-2-yl).

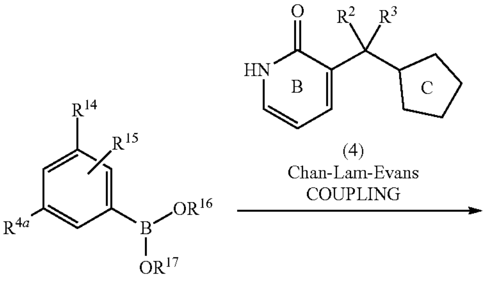

(4) (8)

-continued

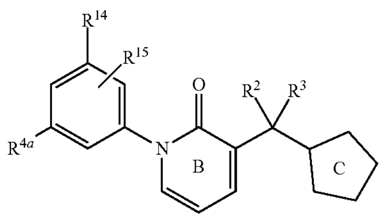

(Ib)

In some embodiments, compound (8), compound (8a) and compound (8b) can be produced from compound (9) using the following method. The symbols are each as defined above.

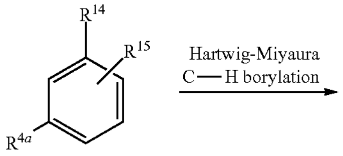

(9)

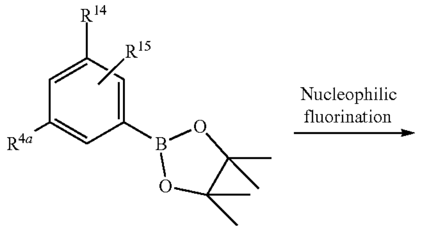

(8a)

-continued

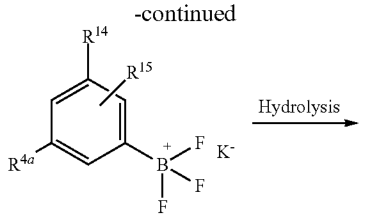

(10)

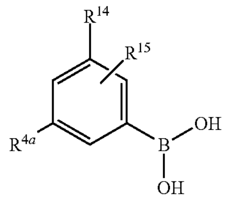

(8b)

Compound (8a) can be produced by a Hartwig-Miyaura C—H borylation reaction of compound (9). A non-limiting example of the metal catalyst that is used is di-μ-methoxobis (1,5-cyclooctadiene)diiridium(I).

Compound (10) can be produced by a nucleophilic fluorination reaction of compound (8a). A non-limiting example of the reagent used for the nucleophilic fluorination reaction is potassium hydrogen fluoride.

Compound (8b) can be produced by a hydrolysis reaction of compound (10). Non-limiting examples of the reagent used for the hydrolysis reaction include trimethylsilyl chloride and lithium hydroxide.

Compound (9) can be produced from compound (11), compound (14), compound (15), or compound (16) using the following method. In the formula, $L^3$ is a leaving group, and other symbols are as defined above.

Non-limiting examples of the "leaving group" indicated by $L^3$ include those listed as examples of the "leaving groups" of $L^1$ or $L^2$ above.

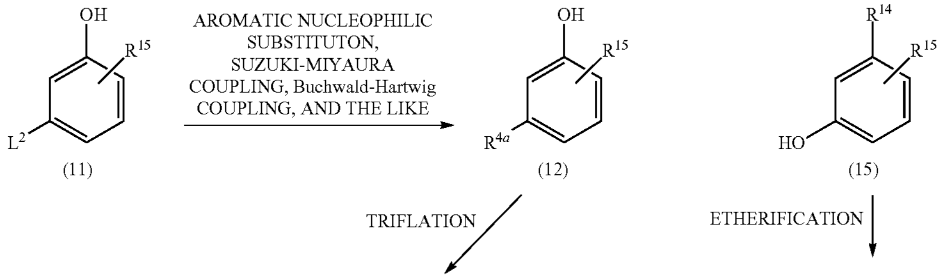

(11) (12) (15)

-continued

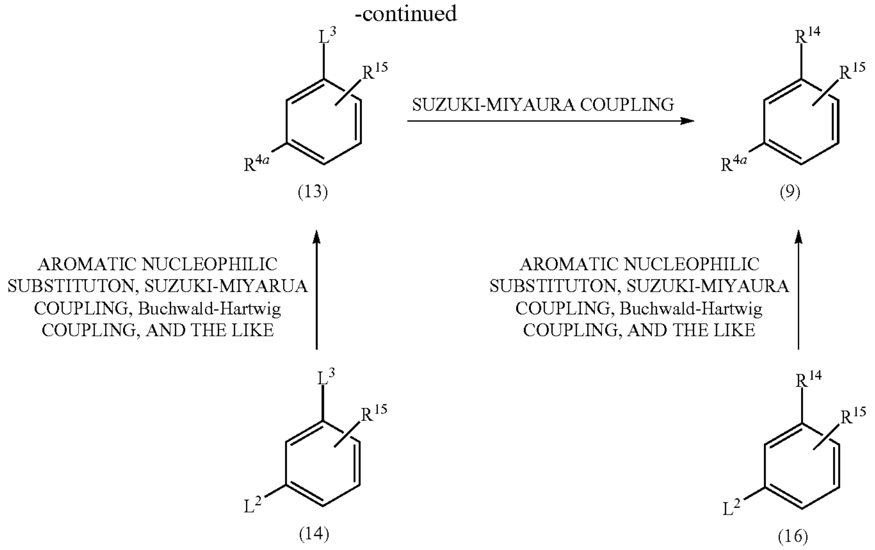

(13) (9) (14) (16)

Compound (12) can be produced from compound (11) using various coupling reactions, such as, for example, an aromatic nucleophilic substitution reaction, a Suzuki-Miyaura coupling reaction, or a Buchwald-Hartwig coupling reaction.

Compound (13) can be produced by a triflate reaction of compound (12), wherein L; is a trifluoromethanesulfonyloxy group.

Compound (13) can also be produced from compound (14) using various coupling reactions, such as, for example, an aromatic nucleophilic substitution reaction, a Suzuki-Miyaura coupling reaction, or a Buchwald-Hartwig coupling reaction.

Compound (9) can be produced by a Suzuki-Miyaura coupling reaction using compound (13). Compound (9) can also be produced by an etherification reaction of compound (15). Compound (9) can also be produced by various coupling reactions using compound (16) such as an aromatic nucleophilic substitution reaction, a Suzuki-Miyaura coupling reaction, or a Buchwald-Hartwig coupling reaction.

Compound (9) can be further transformed in accordance with a method known per se.

Compound (5a), in which ring $A^1$ in compound (5) is a pyridine ring having a substituent $OR^{16}$, can be produced by an aromatic nucleophilic substitution reaction using compound (17) and alcohol:$R^{16}OH$. In the formula, $R^{15}$ is a substituent, and other symbols are each as defined above. A non-limiting example of the "substituent" indicated by $R^{16}$ is a benzyl group.

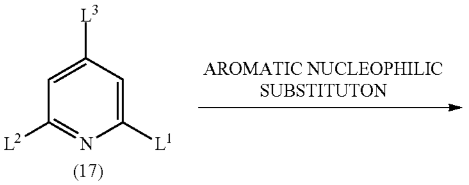

(17)

-continued

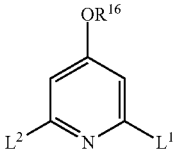

(5a)

Compounds (1), (4), (5), (11), and (14) to (17) can be obtained as commercially available products or produced in accordance with methods known per se or methods conforming to these methods or with the methods described in the Examples.

In Compound (I) obtained in this way, a functional group in the molecule can be converted to a target functional group by combining chemical reactions known per se. Here, examples of chemical reactions include oxidation reactions, reduction reactions, alkylation reactions, acylation reactions, urea formation reactions, hydrolysis reactions, amination reactions, esterification reactions, aryl coupling reactions, and deprotection reactions.

In the production method described above, when the starting material compound includes an amino group, a carboxyl group, a hydroxy group, a carbonyl group, or a mercapto group as a substituent, a protecting group that would be typically used in peptide chemistry or the like for these groups may be introduced, and the target compound can be obtained by removing the protecting group after the reaction as needed.

Configurational isomers (E- and Z-isomers) of Compound (I) can be isolated and purified by a separation means such as extraction, recrystallization, distillation, or chromatography at the point when isomerization occurs, and a pure compound can thus be produced. In addition, corresponding pure isomers can also be obtained by allowing the isomerization of double bonds to progress by heating, an acid catalyst, a transition metal complex, a metal catalyst, a radical species catalyst, photoirradiation, a strongly basic catalyst, or the like in accordance with the methods described on pages 251 to 253 of New Experimental Chemistry Vol. 14 (edited by the Chemical Society of Japan) and pages 273 to 274 of the 4th Edition of Experimental Chemistry Vol. 19 (edited by the Chemical Society of Japan) or methods conforming to these methods.

While a stereoisomer may be generated depending on which type of substituent is used in Compound (I), compounds in which this isomer is unaccompanied and mixtures thereof are also included within the scope of the present disclosure.

When the target product is to be obtained in a free state by the reaction described above, it may be converted to a salt in accordance with a conventional method, and when it is to be obtained as a salt, it may be converted to a free form or another salt in accordance with a conventional method. Illustratively, Compound (I) obtained in this way can be isolated and purified from the reaction solution by a known means such as, for example, dissolution, concentration, solvent extraction, fractional distillation, crystallization, recrystallization, or chromatography.

When Compound (I) exists as a configurational isomer, a diastereomer, a conformer, or the like, it can be respectively isolated by the aforementioned separation and purification means as desired. In addition, when Compound (1) is a racemate, it can be separated into a d-form and an 1-form or an S-form and an R-form by an ordinary optical resolution means.

Compound (I) obtained in this way, as well as other reaction intermediates and the starting material compounds, can be isolated and purified from the reaction mixture by methods known per se—for example, by using a means such as extraction, concentration, neutralization, filtration, distillation, recrystallization, column chromatography, thin film chromatography, preparative high performance liquid chromatography (preparative HPLC), or medium-pressure preparative liquid chromatography (medium-pressure preparative LC).

Compound (I), which is a salt, can be produced in accordance with a known means—for example, by adding an inorganic acid or an organic acid when Compound (I) is a basic compound or by adding an organic base or an inorganic base when Compound (I) is an acidic compound.

When enantiomers are present in Compound (I), these individual enantiomers and mixtures thereof are also included in the scope of the present disclosure. These isomers can also be optically resolved or produced individually as desired in accordance with a known means.

In the present specification, a GPR139 receptor antagonist action includes a GPR139 receptor inverse agonist action. In some embodiments, a compound having a GPR139 receptor antagonist action is a compound having a GPR139 receptor inverse agonist action.

As described in detail in the test examples below, the GPR139 receptor inverse agonist action can be confirmed, for example, by the reduced production or inhibited production of inositol monophosphate (also abbreviated as $IP_1$ in the present specification), a metabolite of inositol triphosphate, which is the second messenger in the downstream of signal transmission in GPR139 (also abbreviated as $IP_3$ in the present specification).

Compound (I) can be used as a drug for preventing, treating, or diagnosing various diseases described below in mammals (for example, mice, rats, hamsters, rabbits, cats, dogs, cows, sheep, monkeys, humans, and the like). For example, Compound (I) is expected to be useful as a drug for preventing or treating diseases such as:

(1) Psychiatric disorders (for example, depression, major depression, depressive episodes, minor depressive disorder, bipolar depression, dysthymic disorder, persistent depressive disorder, emotional disturbance (for example, seasonal affective disorder or the like), recurrent depression, postpartum depression, stress disorder, major depression disorder accompanying mental illness (including delusional disorder and schizophrenia), manic illness or mixed mood episodes, hypomanic mood episodes, depressive episodes with atypical features, depressive episodes with depressive features, depressive episodes with catatonic features, post-stroke depressive episodes, depression with anhedonia, major depression with anhedonia, minor depressive disorder with anhedonia, bipolar depression with anhedonia, dysthymic disorder with anhedonia, persistent depressive disorder with anhedonia, emotional disturbance with anhedonia, recurrent depression with anhedonia, postpartum depression with anhedonia, stress disorder with anhedonia, bipolar disorder with anhedonia, schizophrenia with anhedonia, anxiety disorder with anhedonia, mood disorder with anhedonia, Alzheimer's disease with anhedonia, dementia with Lewy bodies, Parkinson's disease with anhedonia, Huntington's disease with anhedonia, refractory major depression with anhedonia, refractory bipolar disorder with anhedonia, depressive symptoms, manic illness, manic episodes, hypomanic episodes, maniform episodes, hypomaniform episodes, delirium, symptoms peripheral to dementia (psychiatric symptoms or behavioral disorders), anxiety, generalized anxiety disorder, anxiety syndrome, mood disorder, cyclothymic disorder, premenstrual dysphoric disorder, generalized anxiety disorder, anxiety syndrome, panic disorder, phobia, social phobia, social anxiety disorder, obsessive-compulsive disorder, post-traumatic stress syndrome, post-traumatic stress disorder, schizoaffective psychosis, paranoid-type or depression-type schizoaffective psychosis, paranoid-type personality disorder, Tourette syndrome, autism spectrum disorder, fragile X syndrome, Rett syndrome, maladjustment, bipolar disorder (including type I bipolar disorder and type 11 bipolar disorder), neurosis, drug addiction, schizophrenia (for example, positive symptom, negative symptom, cognitive impairment, paranoid schizophrenia, disorganized schizophrenia, catatonic schizophrenia, unspecialized schizophrenia, and residual schizophrenia), schizophrenia spectrum disorder, dyskinesia, mental retardation, paranoid tendency, schizophreniform disorder, catatonia, neurosis, fatigue, chronic fatigue syndrome, lack of energy, anxiety neurosis, obsessional neurosis, panic disorder, epilepsy, anxiety symptoms, unpleasant mental state, emotional abnormality, emotional circulation temperament, nervousness, fainting, addiction, sexual debility, attention deficit hyperactivity disorder (ADHD), psychotic major depression, intractable major depression, refractory depression, refractory major depression, cognitive impairment accompanying major depression, refractory bipolar disorder, temper tantrum, weight gain, weight loss, psychomotor agitation, psychomotor retardation, worthlessness, guilt feeling, impaired ability to think or concentrate, suicidal thoughts, suicide attempt, melancholia, psychotic disorder (for example, short-term psychotic disorder and shared psychotic disorder), obesity-induced mental illness, paranoia, Noonan's syndrome, Angelman syndrome, Prader-Willi syndrome, Beckwith-Wiedemann syndrome, Silver-Russell syndrome, tuberous sclerosis, Williams' syndrome, Kallmann syndrome, Rubinstein-Taybi syndrome, eating behavior disorder and food intake disorder groups, disorders, pica, merycism, avoidant/restrictive food intake disorder, anorexia, anorexia mentalis (anorexia nervosa and anorexia), psychogenic loss of appetite, atypical psychogenic loss of appetite, bulimia, neurogenic bulimia (bulimia nervosa), nervous increase in appetite, atypical neurogenic bulimia, binge eating disorder, psychogenic hyperphagia, psychogenic pregnancy vomiting, and psychogenic vomiting);

(2) Neurodegenerative disease (for example, Alzheimer's disease, senile dementia of the Alzheimer type, Parkinson's disease, Huntington's disease, dementia accompanying Huntington's disease, multi-infarct dementia, frontotemporal dementia, Parkinson type dementia, Parkinson type frontotemporal dementia, alcohol-related dementia or other drug-related dementia, dementia accompanying intracranial tumor or cerebral trauma, neurodegeneration accompanying cerebral trauma, neurodegeneration accompanying stroke, neurodegeneration accompanying cerebral infarction, neurodegeneration accompanying hypoglycemia, neurodegeneration accompanying epileptic seizure, neurodegeneration accompanying neurotoxin poisoning, multiple system atrophy, spinal cord injury, AIDS-related dementia, progressive supranuclear palsy, Pic's syndrome, Niemann-Pick syndrome, corticobasal degeneration, Down's syndrome, vascular dementia (VaD) (for example, multi-infarct dementia, strategic single infarct VaD, small vessel lesion dementia, hypoperfusion VaD, cerebral hemorrhage VaD, chronic subdural hematoma, and the like), postencephalitic Parkinsonism, Lewy body dementia, HIV dementia, amyotrophic lateral sclerosis (ALS), motor neuron disease (MND), Creutzfeldt-Jakob disease, prion disease, cerebral palsy, multiple sclerosis, and neuromyopathy);

(3) Amnestic disorders, mild cognitive impairment, learning disabilities (for example, dyslexia, dyscalculia, and dysgraphia], or cognitive/memory impairment with aging (for example, age-related memory impairment and senile dementia);

(4) Sleep disorders (for example, intrinsic sleep disorders (for example, psychophysiological insomnia and the like), extrinsic sleep disorders, Circadian rhythm disorders (for example, time zone change syndrome (jet lag), shift work sleep disorder, irregular sleep-wake pattern, delayed sleep phase syndrome, advanced sleep phase syndrome, non-24-hour sleep-wake syndrome, and the like), parasomnia (for example, arousal disorder from non-REM sleep (for example, sleepwalking type, sleep terror type, and the like), nightmare disorder, REM sleep disorder, and restless legs syndrome), sleep disorders accompanying internal medicine or psychiatric disorders (for example, chronic obstructive pulmonary disease, Alzheimer's disease, Parkinson's disease, cerebrovascular dementia, schizophrenia, depression, and anxiety), stress insomnia, insomnia, insomnia neuropathy, sleep apnea syndrome (for example, obstructive sleep apnea, central sleep apnea, and the like), sleep-related hypoventilation (for example, primary alveolar hypoventilation syndrome, congenital central hypoventilation syndrome, and the like), narcolepsy, cataplexy, and hypersomnia);

(5) Drug addiction (substance-related disorders and substance addiction) (for example, substance use disorders (for example, alcohol dependence, marijuana (including synthetic cannabinoids) dependence, hallucinogen (for example, ketamine, phencyclidine, and the like) dependence, inhalant dependence, opioid dependence, painkiller addiction, hypnotic addiction, anxiolytic dependence, psychostimulant (for example, amphetamine-type substances, cocaine, cathinone, synthetic catione, NMDA, NMDA-related drug (for example, MDA and the like), and the like) dependence, caffeine addiction, tobacco dependence, nicotine dependence, alcohol use disorder, cannabis (including synthetic cannabinoids) use disorder, hallucinogen use disorder, inhalant use disorder, opioid use disorder, painkiller use disorder, hypnotic use disorder, anxiolytic use disorder, psychostimulant use disorder, caffeine use disorder, tobacco use disorder, nicotine use disorder, substance-induced disorders (for example, alcoholism, alcohol withdrawal, caffeinism, caffeine withdrawal, marijuana (including synthetic cannabinoids) addiction, marijuana (including synthetic cannabinoids) withdrawal, hallucinogen addiction, hallucinogen persistent perceptual disorder, inhalant addiction, opioid addiction, opioid withdrawal, painkiller addiction, hypnotic addiction, anxiolytic addiction, painkiller withdrawal, hypnotic withdrawal, anxiolytic withdrawal, psychostimulant addiction, psychostimulant withdrawal, caffeine withdrawal, tobacco withdrawal, nicotine withdrawal, substance (including alcohol, caffeine, marijuana, (including synthetic cannabinoids), hallucinogens, inhalants, opioids, painkillers, sleeping drugs, anti-anxiety drugs, psychostimulants, caffeine, tobacco, nicotine, and the like)-induced mental illness (for example, psychotic disorder, bipolar disorder and related disorders, depressive disorder, anxiety, obsessive-compulsive disorder and related disorders, sleeping disorders, sexual dysfunction, delirium, neurocognitive disorders, and the like), acute intoxication, harmful use (for example, antidepressant abuse, drug abuse, and the like), dependence syndrome (for example, drug dependence, non-narcotic painkiller addiction, and the like), withdrawal state (for example, drug withdrawal syndrome and the like), withdrawal state with delirium, psychotic disorders (for example, addictive psychosis, steroid psychosis, and the like), amnesia syndrome, residual and delayed psychotic disorders (for example, drug addiction depression and the like), psychiatric side effects, addictive mental disorders, drug-induced psychiatric disorders, drug preference, pharmacophobia, pharmacomania, and drug withdrawal);

(6) Respiratory depression induced by anesthetics, traumatic disease, neurodegenerative disease or the like;

(7) Pain (for example, psychogenic pain (somatoform disorder, pain disorder, somatization disorder, hypochondria, conversion disorder, chronic pain with depression, psychogenic glossodynia, psychogenic headache, psychogenic backache, psychogenic stomachache, neurologic ear pain, physical pain disorder, mental pain, and psychogenic dyspareunia), inflammatory pain, acute pain, cancer-related persistent pain, cancer-related breakthrough pain, cancer-related pain, persistent pain, somatic pain, breakthrough pain, chronic pain (for example, intractable pain, post thoracotomy pain syndrome, peripheral neuropathic pain, peripheral neuropathic pain, neuropathic pain, central nervous system disorder pain, central neuropathic pain, central post-stroke pain, and the like), tenderness, pantalgia, dull pain, skin pain, radiating pain, headache (for example, inflammatory headache, facial pain, occipital pain, dental facial pain, chronic daily headache, neuralgic headache, frontal headache, temporal headache, neck pain, heaviness of the head, pain in top of head, paroxysmal headache, cheek pain, traction headache, burning mouth syndrome, primary headache, headache due to mental illness, migraine, chronic cluster headache, cluster headache, trigeminal nerve/autonomic cephalalgia, recurrent cluster headache, paroxysmal hemicrania, recurrent paroxysmal hemicrania, chronic paroxysmal hemicrania, short-lasting unilateral neuralgiform headache with conjunctival injection and tearing, vascular headache, muscle contraction headache, tension-type headache, recurrent tension-type headache, chronic tension-type headache, cephalalgia traumatica, post-chronic trauma headache, medication overuse headache, Sluder neuralgia, Tolosa-Hunt syndrome, ocular headache, combined headache, hemicrania continua, primary cough headache, headache during primary exercise, primary headache associated with sexual activity, cold-stimulus headache, primary thunderclap headache, primary puncture-like headache, nummular headache, hypnic headache, new daily persistent headache, headache due to epileptic seizure, hypertensive headache, headache due to nasal/sinus disease, tension headache, and the like), trigeminal nerve disorders (for example, trigeminal neuralgia, atypical facial pain, trigeminal nerve hypersensitivity, trigeminal neuropathy, and the like), glossopharyngeal nerve disorders (for example, glossopharyngeal neuralgia and the like), vagus nerve disorders (for example, superior laryngeal neuralgia, vagal neuralgia, and the like), hypoglossal nerve disorder, multiple cranial neuropathy, postherpetic neuralgia, post-herpes zoster trigeminal neuralgia, multiple neuropathy after herpes zoster, neuralgic amyotrophy, phantom pain, stump neuralgia, deafferentation pain, lumbar sciatic neuralgia, upper limb mononeuropathy (for example, median nerve neuralgia, ulnar neuralgia, and the like), lower limb mononeuropathy (for example, meralgia paraesthetica and the like), rib neuropathy (for example, intercostal neuralgia and the like), neuropathic pain, diabetic neuropathic pain, diabetic neuralgia (for example, type 1 diabetic neuralgia, type 2 diabetic neuralgia, and the like), cardiac neuralgia, persistent somatic symptom disorder, epidemic pleural pain, autonomic reflex pain, myelalgia, lumbar puncture headache, ophthalmalgia, otalgia, thalamic pain, pharyngodynia, rhinalgia, toothache, jaw pain, glossodynia, rectalgia, arthralgia, back pain, spondylalgia, myalgia, and neuralgia); and (8) Traumatic brain injury and associated disorders or complications, post-concussion syndrome, shaken baby syndrome, stroke, age-related macular degeneration (ARMD), ocular palatal tremor, convulsion, cerebral infarction, cerebral hemorrhage, hearing loss, radiation lethargy syndrome, anorexia nervosa, eating disorder, psychogenic loss of appetite, hyperphagia, other eating disorders, gambling addiction, video game addiction, obesity, diabetes, muscle spasm, Ménière disease, autonomic ataxia, alopecia, glaucoma, hypertension, heart disease, tachycardia, cardiac insufficiency, hyperpnea, bronchial asthma, apnea, sudden infant death syndrome, inflammatory disease, allergic disease, impotence, menopause disorder, infertility, cancer, immunodeficiency syndrome due to HIV infection, autoimmune encephalitis (for example, autoimmune limbic encephalitis), stress-induced immune deficiency syndrome, meninx, acromegaly, incontinence, metabolic syndrome, osteoporosis, peptic ulcer, irritable bowel syndrome, inflammatory bowel disease, ulcerative colitis, Crohn's disease, stress gastrointestinal disorders, vomiting, peptic ulcer, diarrhea, constipation, and postoperative ileus.

Compound (I) may also be used in the form of a prodrug. A prodrug of Compound (I) refers to a compound that is converted to Compound (I) by a reaction induced by enzymes, gastric acids, or the like under physiological conditions in the body; that is, a compound that is transformed into Compound (I) by enzymatically inducing oxidation, reduction, hydrolysis, or the like, or a compound that is transformed into Compound (I) by inducing hydrolysis or the like with gastric acid or the like.

Examples of prodrugs of Compound (I) include compounds in which an amino group of Compound (I) is acylated, alkylated, or phosphorylated (for example, compounds in which an amino group of Compound (I) is eicosanoylated, alanylated, pentylaminocarbonylated, (5-methyl-2-oxo-1,3-dioxol-4-yl)methoxycarbonylated, tetrahydrofuranylated, pyrrolidylmethylated, pivaloyloxymethylated or tert-butylated, and the like); compounds in which a hydroxy group of Compound (1) is acylated, alkylated, phosphorylated, or borated (for example, compounds in which a hydroxyl group of Compound (I) is acetylated, palmitoylated, propanoylated, pivaloylated, succinylated, fumarylated, alanylated, or dimethylaminomethylcarbonylated, and the like); and compounds in which a carboxy group of Compound (I) is esterified or amidated (for example, compounds in which a carboxyl group of Compound (I) is ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxol-4-yl) methyl esterified, cyclohexyloxycarbonylethyl esterified, or methylamidated, and the like). These compounds can be produced from Compound (I) in accordance with a method known per se. A prodrug of Compound (I) may be a compound that transforms into Compound (I) under physiological conditions such as those as described in "Development of Pharmaceutical Products" vol. 7, Molecule Design, p. 163-198, Hirokawa Shoten (1990).

A compound of Formula (I) may exhibit favorable pharmacokinetics properties (for example, drug half-life in blood, intracerebral transferability, and metabolic stability) and low toxicity (for example, superior as a pharmaceutical from the perspectives of acute toxicity, chronic toxicity, genetic toxicity, reproduction toxicity, cardio-toxicity, drug interactions, carcinogenicity, and the like), allowing safe administration orally or non-orally to mammals (for example, humans, monkeys, cows, horses, pigs, mice, rats, hamsters, rabbits, cats, dogs, sheep, goats, and the like) either directly as a pharmaceutical or as a pharmaceutical composition mixed with at least one pharmaceutically acceptable carrier or the like.

As used herein, "non-oral administration" includes intravenous, intramuscular, subcutaneous, intraorgan, intranasal, intradermal, instillation, intracerebral, intrarectal, intravaginal, intraperitoneal, intratumoral, and proximal tumor administration, as well as direct administration into a lesion.

In some embodiments, the dose of Compound (I) differs depending on the administration route, symptoms, and the like. In some embodiments, when administered orally to a patient with depression (for example, an adult with a weight in the range of 40 kg to 80 kg, for example, 60 kg), the dose is, for example, 0.001 to 1000 mg/kg of body weight per day, for example, from 0.01 to 100 mg/kg of body weight per day, and, for example, from 0.1 to 10 mg/kg of body weight per day. This amount can be spread out over, for example, 1 to 3 doses per day.

A pharmaceutical comprising Compound (I) can be used as Compound (I) alone or as a pharmaceutical composition prepared by mixing Compound (I) and at least one pharmaceutically acceptable carrier in accordance with a method known per se as a production method for pharmaceutical preparations (for example, a method described in the Japanese Pharmacopoeia. A pharmaceutical comprising Compound (I) may be administered orally or non-orally (intravenous, intramuscular, subcutaneous, intraorgan, intranasal, intradermal, instillation, intracerebral, intrarectal, intravaginal, intraperitoneal, or lesion administration or the like), for example, as a tablet (including sugar-coated tablets, film-coated tablets, sublingual tablets, orally disintegrating tablets, buccal tablets, and the like), a pill, a powdered drug, granules, a capsule (including soft capsules and microcapsules), a lozenge, a syrup, a liquid preparation, an emulsion, a suspension, a controlled-release formulation (for example, a rapid-release preparation, a sustained-release preparation, or a sustained-release microcapsule), an aerosol agent, a film agent (for example, an orally disintegrating film or an oral mucosal film), an injection (for example, a subcutaneous injection, an intravenous injection, an intramuscular injection, or an intraperitoneal injection), intravenous drip, a percutaneous absorption type preparation, an ointment, a lotion, a patch, a suppository (for example, a rectal suppository or a vaginal suppository), a pellet, a transnasal agent, a transpulmonary agent (inhalant), an ophthalmic solution, or the like.

Various organic or inorganic carriers commonly used as starting materials for preparations may be used as the "pharmaceutically acceptable carrier" described above. For example, in solid preparations, excipients, lubricants, binders, disintegrators, and the like may be used, and in liquid preparations, solvents, dissolution aids, suspending agents, isotonizing agents, buffers, analgesics, and the like may be used. In addition, additives for preparations such as preservatives, antioxidants, colorants, and sweeteners can also be used as necessary.

Non-limiting examples of excipients include lactose, sucrose, D-mannitol, starch, corn starch, crystalline cellulose, and light silicic anhydride.

Non-limiting examples of lubricants include magnesium stearate, calcium stearate, talc, and colloidal silica.

Non-limiting examples of binders include crystalline cellulose, sucrose, D-mannitol, dextrin, hydroxypropylcellulose, hydroxypropylmethylcellulose, polyvinylpyrrolidone, starch, saccharose, gelatin, methylcellulose, and sodium carboxymethylcellulose.

Non-limiting examples of disintegrants include starch, carboxymethylcellulose, carboxymethylcellulose calcium, sodium carboxymethyl starch, and L-hydroxypropylcellulose.

Non-limiting examples of solvents include water for injection, alcohol, propylene glycol, macrogol, sesame oil, corn oil, and olive oil.

Non-limiting examples of dissolution aids include polyethylene glycol, propylene glycol, D-mannitol, benzyl benzoate, ethanol, trisaminomethane, cholesterol, triethanolamine, sodium carbonate, and sodium citrate.

Non-limiting examples of suspending agents include surfactants such as stearyltriethanolamine, sodium lauryl sulfate, lauryl aminopropionate, lecithin, benzalkonium chloride, benzethonium chloride, and glycerol monostearate; and hydrophilic polymers such as polyvinyl alcohol, polyvinylpyrrolidone, sodium carboxymethylcellulose, methylcellulose, hydroxymethylcellulose, hydroxyethylcellulose, and hydroxypropylcellulose.

Non-limiting examples of isotonizing agents include glucose, D-sorbitol, sodium chloride, glycerin, and D-mannitol.

Non-limiting examples of buffers include buffer solutions such as phosphate, acetate, carbonate, and citrate.

Non-limiting examples of analgesics include benzyl alcohol and the like. Non-limiting examples of preservatives include paraoxybenzoate esters, chlorobutanol, benzyl alcohol, phenethyl alcohol, dehydroacetic acid, and sorbic acid.

Non-limiting examples of antioxidants include sulfite, ascorbic acid, and a-tocopherol.

Although differing depending on the dosage form, the administration method, the carrier, and the like, in some embodiments, the pharmaceutical composition may be produced in accordance with a conventional method by adding Compound (I) at a ratio of, for example, 0.01% to 100% (w/w), for example, 0.1% to 95% (w/w), with respect to the total amount of the pharmaceutical composition.

Compound (I) may also be used in combination with other active ingredients, referred to as combination drugs herein.

Non-limiting examples of combination drugs include: acetylcholinesterase inhibitors (for example, donepezil, rivastigmine, galanthamine, and zanapezil), P-amyloid protein production, secretion, accumulation, aggregation and/or deposition inhibitors, P-secretase inhibitors (for example, 6-(4-biphenylyl)methoxy-2-[2-(N,N-dimethylamino)ethyl]tetralin, 6-(4-biphenylyl)methoxy-2-(N,N-dimethylamino)methyltetralin, 6-(4-biphenylyl)methoxy-2-(N,N-dipropylamino)methyltetralin, 2-(N,N-dimethylamino)methyl-6-(4'-methoxybiphenyl-4-yl)methoxytetralin, 6-(4-biphenylyl)methoxy-2-[2-(N,N-diethylamino)ethyl]tetralin, 2-[2-(N,N-dimethylamino)ethyl]-6-(4'-methylbiphenyl-4-yl)methoxytetralin, 2-[2-(N,N-dimethylamino)ethyl]-6-(4'-methoxybiphenyl-4-yl)methoxytetralin, 6-(2',4'-dimethoxybiphenyl-4-yl)methoxy-2-[2-(N,N-dimethylamino)ethyl]tetralin, 6-[4-(1,3-benzodioxole-5-yl)phenyl]methoxy-2-[2-(N,N-dimethylamino)ethyl]tetralin, and 6-(3',4'-dimethoxyphenyl-4-yl)methoxy-2-[2-(N,N-dimethylamino)ethyl]tetralin, optically active substances thereof, salts thereof, hydrates thereof, and OM99-2 (WO 01/00663)), γ-selectase inhibitors, β-amyloid protein aggregation inhibitors (for example, PTI-00703, Tramiprosate, PPI-368 (Japanese Translation of PCT Application No. H11-514333), PPI-558 (Japanese Translation of PCT Application No. 2001-500852), SKF-74652 (2-(4-Methoxyphenyl)-3-[4-[3-(diethylamino)propoxy]benzoyl]-5-chlorobenzofuran, Biochem. J. (1999), 340(1), 283-289)), β-amyloid vaccines, β-amyloid degrading enzymes and the like, brain function enhancers (for example, aniracetam and nicergoline), other Parkinson's disease medicines [(for example, dopamine receptor agonists (for example, L-dopers, bromocriptine, pergolide, talipexole, pramipexole, cabergoline, and amantadine), monoamine oxidase (MAO) inhibitors (for example, deprenyl, selegiline (selegiline), remacemide, and riluzole), anticholinergic agents (for example, trihexyphenidyl and biperiden), and COMT inhibitors (for example, entacapone)], amyotrophic lateral sclerosis therapeutics (for example, riluzole and neurotrophic factor), medicines for abnormal behavior, wandering, or the like accompanying the progression of dementia (for example, sedatives and anxiolytics), apoptosis inhibitors (for example, CPI-1189, Emricasan, CEP-1347), neuronal differentiation/regeneration promoters (for example, leteprinim, Xaliproden (SR-57746-A), SB-216763, Y-128, VX-853, prosaptide, 5,6-methoxy-2-[2,2,4,6,7-pentamethyl-3-(4-methylphenyl)-2,3-dihydro-1-benzofuran-5-yl]isoindoline, 5,6-dimethoxy-2-[3-(4-isopropylphenyl)-2,2,4,6,7-pentamethyl-2,3-dihydro-1-benzofuran-5-yl]isoindoline, 6-[3-(4-isopropylphenyl)-2,2,4,6,7-pentamethyl-2,3-dihydro-1-benzofuran-5-yl]-6,7-dihydro-5H-[1,3]dioxolo[4,5-f]isoindole, and optically active substances, salts, and hydrates thereof), nonsteroidal anti-inflammatory drugs (meloxicam, tenoxicam, indomethacin, ibuprofen, celecoxib, rofecoxib, aspirin, indomethacin, and the like), steroids (dexamethasone, hexestrol, cortisone acetate, and the like), disease-modifying antirheumatic drugs (DMARDs), anti-cytokine drugs (for example, TNF inhibitors and MAP kinase inhibitors), pollakiuria and urinary incontinence medicines (for example, flavoxate hydrochloride, oxybutynn hydrochloride, and propiverine hydrochloride), phosphodiesterase inhibitors (for example, sildenafil (citrate)), dopaminergic drugs (for example, apomorphine), antiarrhythmic drugs (for example, mexiletine), sex hormones or derivatives thereof (for example, progesterone, estradiol, and estradiol benzoate), osteoporosis medicines (for example, alfacalcidol, calcitriol, elcatonin, salmon calcitonin, estriol, iprivlavone, pamidronate disodium, alendronate sodium hydrate, and incadronate disodium), parathyroid hormone (PTH), calcium receptor antagonists, insomnia medicines (for example, benzodiazepine-based drugs, non-benzodiazepine-based drugs, melatonin agonists, and orexin receptor antagonists), schizophrenia medicines (for example, typical antipsychotics such as haloperidol; atypical antipsychotics such as clozapine, olanzapine, risperidone, and aripiprazole; drugs which affect metabotropic glutamate receptors or ion channel conjugate-type glutamate receptors; and phosphodiesterase inhibitors), benzodiazepin-based drugs (chlordiazepoxide, diazepam, potassium clorazepate, lorazepam, clonazepam, alprazolam, and the like), L-type calcium channel inhibitors (pregabalin and the like), tricyclic or tetracyclic antidepressants (imipramine hydrochloride, amitriptyline hydrochloride, desipramine hydrochloride, clomipramine hydrochloride, and the like), selective serotonin reuptake inhibitors (fluvoxamine maleate, fluoxetine hydrochloride, citalopram hydrobromide, sertraline hydrochloride, paraxetine hydrochloride, escitalopram oxalate, and the like), serotonin and norepinephrine reuptake inhibitors (venlafaxine hydrochloride, duloxetine hydrochloride, desvenlafacine hydrochloride, and the like), noradrenaline reuptake inhibitors (reboxetine mesylate and the like), mirtazapine, trazodone hydrochloride, nefazodone hydrochloride, bupropion hydrochloride, setiptiline maleate, 5-HT2A antagonists (for example, pimavanserin tartrate), 5-HT2A inverse agonists, 5-HT3 antagonists (cyamemazine and the like), non-heart-selective β inhibitors (propranolol hydrochloride, oxiprenolol hydrochloride, and the like), histamine H1 antagnoists (hydroxyzine hydrochloride and the like), schizophrenia medicines (chlorpromazine, haloperidol, sulpiride, clozapine, trifluoperazine hydrochloride, fluphenazine hydrochloride, olanzapine, quetiapine fumarate, risperidone, aripiprazole, and the like), CRF antagonists, other antianxiety drugs (meprobamate and the like), tachykinin antagonists (aprepitant, saredutant, and the like), drugs which affect metabotropic glutamate receptors, drugs which affect GABA receptors, drugs which affect acetylcholine receptors, CCK antagonists, β3 -adrenaline antagonists (amibegron and the like), GAT-1 inhibitors (tiagabine hydrochloride and the like), N-type calcium channel inhibitors, type-2 carbonate dehydrase inhibitors, NMDA glycine site agonists, NMDA antagonists (ketamine, S-ketamine, R-ketamine, ketamine metabolites (for example, (2S,6S;2R,6R)-hydroxynorketamine, (2R,6R)-hydroxynorketamine, and the like), memantine, and the like), peripheral benzodiazepine receptor agonists, vasopressin antagonists, vasopressin V1b antagonists, vasopressin V1a antagonists, phosphodiesterase inhibitors, opioid inhibitors, opioid agonists, uridine, nicotinic acid agonists, thyroid hormones (T3 and T4), TSH, TRH, MAO inhibitors (phenylzine sulfate, tranylcypromine sulfate, moclobemide, and the like), bipolar disorder medicines (lithium carbonate, sodium valproate, lamotrigine, riluzole, felbamate, and the like), cannabinoid CB1 antagonists (rimonabant and the like), FAAH inhibitors, sodium channel inhibitors, anti-ADHD drugs (methylphenidate hydrochloride, methamphetamine hydrochloride, and the like), alcohol dependence medicines, autism medicines, chronic fatigue syndrome medicines, seizure medicines, fibromyalgia medicines, headache medicines, medicines for quitting smoking, myasthenia gravis medicines, cerebral infarction medicines, mania medicines, hypersomnia medicines, pain medicines, dysthymia medicines, autonomic ataxia medicines, male and female sextual dysfunction medicines, migraine medicines, pathological gambling medicines, restless legs syndrome medicines, substance dependence medicines, alcohol-related disease medicines, irritable bowel syndrome medicines, dyslipidemia medicines such as hypocholesterolemic drugs (statin series (pravastatin sodium, atorvastatin, simvastatin, rosuvastatin, and the like), fibrates (clofibrate and the like), and squalene synthesis inhibitors), abnormal behavior medicines or drugs for suppressing dementia-induced wandering (sedatives, antianxiety drugs, and the like), anti-obesity drugs, antidiabetic drugs, diabetic complication medicines, antihypertensive drugs, antihypotensive drugs, diuretics, chemotherapeutic agents, immune modifiers, antithrombotic agents, anticancer agents, and the like.

Two or more types of the combination drugs described above may also be used in combinations at appropriate ratios.

Further, when using a compound of the present disclosure to treat or prevent one or more of the diseases described above, the compound can also be used in combination with biologics (for example, antibody drugs, nucleic acids (for example, antisense oligonucleotide, siRNA, decoys, and the like) or nucleic acid derivatives, aptamer drugs, peptide drugs, and vaccine preparations). Additionally, the compound may be used in combination with gene therapy or the like or used in combination with treatments employed in psychiatric cases in which drugs are not used.

Non-limiting examples of antibody drugs and vaccine preparations include vaccine preparations for angiotensin II, vaccine preparations for CETP, CETP antibodies, TNFα antibodies and antibodies against other cytokines, amyloid β vaccine preparations, type 1 diabetes vaccines (for example, DIAPEP-277 available from Peptor), anti-HIV antibodies or HIV vaccine preparations, antibodies or vaccine preparations for cytokines, renin/angiotensin enzymes or products thereof, antibodies or vaccine preparations for enzymes or proteins involved in lipid metabolism in blood, antibodies or vaccines related to enzymes or proteins involved in the blood congealing fibrinogenolysis system, and antibodies or vaccine preparations for proteins involved in carbohydrate metabolism or insulin resistance. In addition, Compound (I) may also be used in combination with biologics related to growth factors such as GH or IGF.

Non-limiting examples of gene therapies include therapies using genes related to cytokines, renin/angiotensin enzymes and products thereof, G-proteins, and G-protein coupled receptors and phosphoric acid enzymes thereof, therapies using DNA decoys such as NFκB decoys, therapies using antisense, therapies using genes related to enzymes or proteins involved in lipid metabolism in blood (for example, genes related to the metabolism, excretion, and absorption of cholesterol, triglyceride, HDL cholesterol, or phospholipids in blood), therapies using genes related to enzymes or proteins involved in angiogenic therapy for peripheral vascular disease or the like (for example, growth factors such as HGF and VEGF), therapies using genes related to proteins involved in carbohydrate metabolism or insulin resistance, and gene therapies using antisense for cytokines such as TNF, virus vectors (for example, adenovirus, lentivirus, adeno-associated virus, retrovirus, vaccinia virus, herpes virus, human papillomavirus, Sendai virus, and the like), or non-virus vectors (for example, plasmids, lipid particles, and the like).

Non-limiting examples of treatments employed in psychiatric cases that do not use drugs include psychotherapies including modified electroconvulsive therapy, deep brain stimulation, repetitive transcranial magnetic stimulation, and cognitive behavior therapy.

In addition, a compound of the present disclosure can be used in combination with various organ regeneration methods such as heart regeneration, kidney regeneration, pancreas regeneration, and blood vessel regeneration, cell transplantation therapy utilizing bone marrow cells (marrow monocytes and marrow stem cells), or artificial organs utilizing tissue engineering (for example, artificial blood vessels and myocardial cell sheets), each of which uses internal or external cells (including genetic modification).

In some embodiments, combining Compound (I) with a combination drug yields may enable one or more of the following outcomes:

(1) the dose can be reduced in comparison to cases in which Compound (I) or the combination drug is administered alone;
(2) a drug to be used in combination with Compound (I) can be selected in accordance with the symptoms (mild symptoms, severe symptoms, or the like) of the patient;
(3) a long treatment period can be established by selecting a combination drug with a different mechanism of action than that of Compound (I);
(4) therapeutic effects can be maintained by selecting a combination drug with a different mechanism of action than that of Compound (I); and
(5) a synergistic effect can be achieved by using Compound (I) in combination with the combination drug.

The use of Compound (I) and a combination drug in combination will be referred to as the "combination agent of the present disclosure" hereinafter.

When using the combination agent of the present disclosure, the administration periods of Compound (I) and the combination drug are not limited, and Compound (I) or a pharmaceutical composition thereof and the combination drug or a pharmaceutical composition thereof may be administered to the subject simultaneously or at different times. The dose of the combination drug need only conform to a dose that is used clinically and may be selected appropriately based on the subject, the administration route, the disease, the combination, or the like.

The administration form of the combination agent of the present disclosure is not limited as long as Compound (I) and the combination drug are combined at the time of administration. Non-limiting examples of such administration forms include: (1) administration of a single preparation obtained by formulating Compound (I) and the combination drug simultaneously; (2) simultaneous administration of two types of preparations obtained by separately formulating Compound (I) and the combination drug for the same administration route; (3) administration of two types of preparations obtained by separately formulating Compound (I) and the combination drug for the same administration route at different times; (4) simultaneous administration of two types of preparations obtained by separately formulating Compound (I) and the combination drug for different administration routes; and (5) administration of two types of preparations obtained by separately formulating Compound (I) and the combination drug for different administration routes at different times (for example, administration in the order of Compound (I) followed by the combination drug, or administration in the reverse order).

In some embodiments, the combination agent of the present disclosure has low toxicity, and Compound (1) and/or the combination drug described above can be mixed with at least one pharmaceutically acceptable carrier in accordance with a known method and safely administered orally or non-orally (for example, via topical, rectal, or intravenous administration) as a pharmaceutical composition, for example, a tablet (for example, sugar-coated tablets and film-coated tablets), a powdered drug, granules, a capsule (for example, soft capsules), a liquid preparation, an injection, a suppository, a sustained-release preparation, or the like. An injection can be administered by intravenous, intramuscular, subcutaneous or intraorgan administration or administered directly into the lesion.

Non-limiting examples of pharmaceutically acceptable carriers that may be used in the production of the combination agent of the present disclosure include those described above.

The blending ratio of Compound (I) and the combination drug in the combination agent of the present disclosure can be selected appropriately based on the subject, the administration route, the disease, and the like.

For example, although the content of Compound (T) in the combination agent of the present disclosure differs depending on the form of the preparation, in some embodiments, the content is around 0.01 to 100 wt. %, for example, around 0.1 to 50 wt. %, for example, around 0.5 to 20 wt. % with respect to the entire preparation.

Although the content of the combination drug in the combination agent of the present disclosure varies based on the form of the preparation, in some embodiments, the content is around 0.01 to 100 wt. %, for example, around 0.1 to 50 wt. %, for example, around 0.5 to 20 wt. % with respect to the entire preparation.

EXAMPLES

The present disclosure will be described in further detail hereinafter using examples, test examples, and formulation examples. However, these examples, test examples, and formulation examples do not limit the present disclosure and may be modified without departing from the scope of the present disclosure.

"Room temperature" in the examples below ordinarily refers to a temperature between about 10° C. and about 35° C. Unless specified otherwise, the ratio indicated in a mixed solvent refers to the volume ratio. Additionally, unless specified otherwise, % refers to wt. %.

Unless specified otherwise, elution in column chromatography in the examples was performed under observation by Thin Layer Chromatography (TLC). In TLC observations, 60 $F_{254}$ available from Merck was used as a TLC plate, and the solvent used as an eluting solvent in column chromatography was used as a developing solvent. In addition, a UV detector was used for detection. In silica gel column chromatography, an aminopropylsilane-bonded silica gel was used when indicated as NH, and a 3-(2,3-dihydroxypropoxy)propylsilane-bonded silica gel was used when indicated as Diol. In preparative high-performance liquid chromatography (HPLC), an octadecyl-bonded silica gel was used when indicated as C18. Unless specified otherwise, the ratio indicated in an eluting solvent refers to the volume ratio.

ADC/SpecManager software or the like was used for $^1$HNMR analysis. Subtle proton peaks of hydroxyl groups, amino groups, or the like may not be noted.

MS was measured by LC/MS. An ESI method or an APCI method was used as an ionization method. Data indicates actual measurements (found). Molecular ion peaks are ordinarily observed, but data may also be observed as fragment ions. In the case of a salt, a molecular ion peak or fragment ion peak of the free form is observed.

The unit of sample concentration (c) in the optical rotation ($[\alpha]_D$) is g/100 mL.

Elemental analysis values (Anal.) are indicated as calculated values (Calcd) and actual measurements (Found).

Peaks according to powder X-ray diffraction in the examples refer to peaks measured at room temperature with ULtima IV (Rigaku Corporation, Japan) using CuKα rays as a radiation source. The measurement conditions were as follows.

Electric pressure/Electric current: 40 kV/50 mA

Scan speed: 6 degree/min

Scan range of 2 Theta: 2-35 degrees

The degree of crystallization according to powder X-ray diffraction in the examples was calculated by Hermans method.

The following abbreviations are used in the examples below.

mp: melting point

MS: mass spectrum

M: molar concentration

N: normality $CDCl_3$: heavy chloroform

DMSO-$d_6$: heavy dimethylsulfoxide

DMSO: dimethylsulfoxide $^1$H NMR: proton nuclear magnetic resonance

LC/MS: liquid chromatography-mass spectrometry

ESI: electrospray ionization

APCI: atmospheric pressure chemical ionization $Pd_2(dba)_3$: tris(dibenzylideneacetone)dipalladium(0)

TFA: trifluoroacetic acid

DIPEA: N-ethyl-N-isopropylpropane-2-amine $PdCl_2$: palladium(II) chloride $PdCl_2$(dppf): dichloro(1,1'-bis(diphenylphosphino)ferrocene)palladium $PdCl_2(dppf)\cdot CHCl_2$: dichloro(1,1'-bis(diphenylphosphino)ferrocene)palladium dichloromethane adduct n-BuLi: n-butyllithium DMF: N,N-dimethylformamide THF: tetrahydrofuran DME: 1,2-dimethoxyethane EtOH: ethanol AcOH: acetic acid HMPA: hexamethylphosphortriamide NBS: 1-bromopyrrolidine-2,5-dione XPhos: 2-dicyclohexylphosphino-2',4',6'-triisopropyl-1,1'-biphenyl Xantphos: 4,5-bis(diphenylphosphino)-9,9-dimethylxanthene RuPhos: dicyclohexyl(2',6'-diisopropoxy-[1,1'-biphenyl]-2-yl)phosphine SPhos: 2-dicyclohexylphosphino-2',6'-dimethoxy-1,1'-biphenyl dbbpy: 4,4'-di-tert-butyl-2,2'-bipyridine IPE: diisopropyl ether BINAP: 2,2'-bis(diphenylphosphino)-1,1'-binaphthyl

Example 1

3-[(1-Ethyl-1H-pyrazole-4-yl)methyl]-6'-(4-fluorophenyl)-4'-(trifluromethyl)-2H-[1,2'-bipyridine]-2-one

A) Ethyl 1-ethyl-1H-pyrazole-4-carboxylate

A mixture of potassium carbonate (197 g), ethyl 1H-pyrazole-4-carboxylate (100 g), ethyl iodide (122 g), and DMF (200 mL) was stirred overnight at room temperature. Water was added to the mixture at room temperature, which was then extracted with ethyl acetate. After the organic layer was separated and washed with water and a saturated saline solution, it was dried with anhydrous magnesium sulfate and concentrated under reduced pressure to obtain the title compound (121 g).

$^1$H NMR (300 MHz, DMSO-$d_6$) δ 1.26 (3H, t, J=7.2 Hz), 1.37 (3H, t, J=7.2 Hz), 4.12-4.27 (4H, dq, J=11.5, 7.2 Hz), 7.84 (1H, s), 8.33 (1H, s).

B) (1-Ethyl-1H-pyrazole-4-yl)methanol

A mixture of ethyl 1-ethyl-1H-pyrazole-4-carboxylate (48.0 g) and THF (100 mL) was dropped into a mixture of lithium aluminum hydride (16.3 g) and THF (400 mL) at 0-10° C., and the mixture was stirred for one hour at room temperature. After the mixture was diluted with THF (150 mL) and cooled to 0° C., sodium sulfate decahydrate (110 g) was added at 0-10° C. and stirred for one hour at room temperature. The insoluble matter was filtered out, and the filtrate was distilled out under reduced pressure to obtain the title compound (29.9 g).

$^1$H NMR (300 MHz, DMSO-$d_6$) δ 1.33 (3H, t, J=7.3 Hz), 4.07 (2H, q, J=7.2 Hz), 4.32 (2H, d, J=5.3 Hz), 4.77 (1H, t, J=5.5 Hz), 7.32 (1H, s), 7.59 (1H, s). C) 4-(Chloromethyl)-1-ethyl-1H-pyrazole hydrochloride Thionyl chloride (4.39 g) was added to a mixture of (1-ethyl-1H-pyrazole-4-yl)methanol (2.33 g) and acetonitrile (20 mL) at room temperature, and the mixture was stirred overnight at the same temperature. The mixture was concentrated to obtain the title compound (3.23 g).

$^1$H NMR (300 MHz, DMSO-$d_6$) δ 1.34 (3H, t, J=7.2 Hz), 4.10 (2H, q, J=7.4 Hz), 4.69 (2H, s), 7.50 (1H, s), 7.85 (1H, s), 12.32 (1H, m).

D) 3-[(1-Ethyl-1H-pyrazole-4-yl)methyl]-2-methoxypyridine

A mixture of 4-(chloromethyl)-1-ethyl-1H-pyrazole hydrochloride (2.87 g), cesium carbonate (20.7 g), $PdCl_2$(dppf) (2.32 g), (2-methoxypyridine-3-yl)boronic acid (3.15 g), DME (25 mL), and water (2.5 mL) was stirred for one hour at 110° C. in an argon atmosphere. The mixture was diluted with water and extracted with ethyl acetate. After the organic layer was separated and washed with water and a saturated saline solution, it was dried with anhydrous sodium sulfate and concentrated under reduced pressure. The residue was purified by silica gel column chromatography (NH, ethyl acetate/hexane) to obtain the title compound (2.88 g).

MS: $[M+H]^+$ 218.0.

E) 3-[(1-Ethyl-1H-pyrazole-4-yl)methyl]-pyridine-2(1H)-one

Pyridine hydrochloride (1.61 g) was added to a DMF (3 mL) solution of 3-[(1-ethyl-1H-pyrazole-4-yl)methyl]-2- methoxypyridine (302 mg). The mixture was stirred for 16 hours at 90° C. After the mixture was concentrated under reduced pressure, the residue was purified by HPLC (C18, mobile phase: water/acetonitrile (10 mM ammonium bicarbonate system)). The resulting fraction was concentrated under reduced pressure to obtain the title compound (194 mg).

MS: $[M+H]^+$ 204.0.

F) 2-Chloro-6-(4-fluorophenyl)-4-(trifluoromethyl) pyridine

First, 4-(fluorophenyl)boronic acid (6.8 g), potassium carbonate (19.2 g), water (50 mL), bis(triphenylphoshine) palladium(II) chloride (3.25 g), and tri-o-triphosphine (1.41 g) were added to a DMF (150 mL) solution of 2,6-dichloro-4-(trifluoromethyl)pyridine (10 g), and the mixture was stirred overnight at room temperature in an argon atmosphere. Water was added to the mixture at room temperature, which was then extracted with ethyl acetate. After the organic layer was separated and washed with water and a saturated saline solution, it was dried with anhydrous sodium sulfate and concentrated under reduced pressure. The residue was purified by silica gel column chromatography (hexane) to obtain the title compound (10.6 g).

MS: [M+H]~276.3.

G) 3-[(1-Ethyl-1H-pyrazole-4-yl)methyl]-6'-(4-fluorophenyl)-4'-(trifluoromethyl)-2H-[1,2'-bipyridine]-2-one A mixture of 2-chloro-6-(4-fluorophenyl)-4-(trifluoromethyl)pyridine (27.1 mg), 3-[(1-ethyl-1H-pyrazole-4-yl) methyl]pyridine-2(1H)-one (20 mg), cesium carbonate (96 mg), Xantphos (11.4 mg), $Pd_2(dba)_3$ (9.01 mg), and toluene (0.5 mL) was stirred for three hours at 100° C. in an argon atmosphere. After the mixture was concentrated, the residue was purified by silica gel column chromatography (NH, ethyl acetate/hexane) to obtain the title compound (11.1 mg).

$^1H$ NMR (300 MHz, DMSO-$d_6$) δ 1.33 (3H, t, J=7.3 Hz), 3.57-3.66 (2H, m), 4.02-4.12 (2H, m), 6.40 (1H, t, J=7.0 Hz), 7.30-7.43 (4H, m), 7.57 (1H, s), 8.02 (1H, dd, J=7.0, 2.1 Hz), 8.18 (1H, s), 8.27-8.34 (2H, m), 8.42 (1H, s).

Example 3

3-[(1-Ethyl-1H-pyrazole-4-yl)methyl]-6'-(4-fluorophenyl)-2-oxo-4'-(2,2,2-trifluoroethoxy)-2H-[1,2'-bipyridine]-3-carbonitrile A) 4-(Benzyloxy)-2,6-dichloropyridine-3-carbonitrile Benzyl alcohol (79 mg) was added to a DMF (1 mL) solution of sodium hydride (60% content, 31.7 mg) at 0° C. The mixture was stirred for 10 minutes at 0° C. A DMF (1 mL) solution of 2,4,6-trichloropyridine-3-carbonitrile (137 mg) was added to the mixture at 0° C. The mixture was stirred for four hours at 0° C. Water was added to the mixture at 0° C., which was then extracted with ethyl acetate. After the organic layer was separated and washed with water and a saturated saline solution, it was dried with anhydrous sodium sulfate and concentrated under reduced pressure. The residue was purified by silica gel column chromatography (ethyl acetate/hexane) to obtain the title compound (62.4 mg).

$^1H$ NMR (300 MHz, $CDCl_3$) δ 5.29 (2H, s), 6.95 (1H, s), 7.37-7.46 (5H, m).

B) 4-(Benzyloxy)-2-chloro-6-(4-fluorophenyl)pyridine-3-carbonitrile

After a mixture of 4-(benzyloxy)-2,6-dichloropyridine-3-carbonitrile (1.56 g), (4-fluorophenyl)boronic acid (0.938 g), $PdCl_2$(dppf) (0.204 g), cesium carbonate (3.28 g), THF (20 mL), and water (20 mL) was stirred for three hours at 80° C. in a nitrogen atmosphere, the reaction solution was concentrated. Water was added to the resulting residue at room temperature, which was then extracted with ethyl acetate. After the organic layer was separated and washed with water and a saturated saline solution, it was dried with anhydrous sodium sulfate and concentrated under reduced pressure. The residue was purified by silica gel column chromatography (ethyl acetate/hexane) to obtain the title compound (1.70 g).

MS: $[M+H]^+$ 339.0.

C) 4'-(Benzyloxy)-3-[(1-ethyl-1H-pyrazole-4-yl) methyl]-6'-(fluorophenyl)-2-oxo-2H-[1,2'-bipyridine]-3'-carbonitrile A mixture of 4-(benzyloxy)-2-chloro-6-(4-fluorophenyl) pyridine-3-carbonitrile (60.8 mg), 3-[(1-ethyl-1H-pyrazole-4-yl)methyl]pyridine-2(1H)-one (36.5 mg), $Pd_2(dba)_3$ (16.4 mg), Xantphos (20.8 mg), cesium carbonate (175 mg), and toluene (1.5 mL) was stirred for one hour at 100° C. in a sealed tube in an argon atmosphere. The mixture was further irradiated with microwaves for one hour at 100° C. Water was added to the mixture at room temperature, which was then extracted with ethyl acetate. After the organic layer was separated and washed with water and a saturated saline solution, it was dried with anhydrous sodium sulfate and concentrated under reduced pressure. The residue was purified by silica gel column chromatography (ethyl acetate/hexane) to obtain the title compound (34.3 mg).

MS: $[M+H]^+$ 506.2.

D) 3-[(1-Ethyl-1H-pyrazole-4-yl)methyl]-6'-(4-fluorophenyl)-4'-hydroxy-2-oxo-2H-[1,2'-bipyridine]-3'-carbonitrile A mixture of 4'-(benzyloxy)-3-[(1-ethyl-1H-pyrazole-4-yl)methyl]-6'-(fluorophenyl)-2-oxo-2H-[1,2'-bipyridine]-3'-carbonitrile (34.3 mg), 10% palladium-carbon (2.89 mg), THF (1 mL), and methanol (0.5 mL) was stirred for two hours at room temperature in a hydrogen atmosphere at normal pressure. The catalyst was filtered out, and the filtrate was concentrated under reduced pressure to obtain the title compound (26.4 g).

MS: $[M+H]^+$ 416.1.

E) 3-[(1-Ethyl-1H-pyrazole-4-yl)methyl]-6'-(4-fluorophenyl)-2-oxo-4'-(2,2,2-trifluoroethoxy)-2H-[1,2'-bipyridine]-3'-carbonitrile First, 2,2,2-trifluoroethyl trifluoromethanesulfonate (27.4 mg) was added to a mixture of 3-[(1-ethyl-1H-pyrazole-4-yl)methyl]-6'-(4-fluorophenyl)-4'-(trifluoromethyl)-4'-hydroxy-2-oxo-2H-[1,2'-pyridine]-3'-carbonitrile (26.4 mg), potassium carbonate (17.6 mg), and DMF (1 mL) at room temperature. The mixture was stirred for one hour at 80° C. Water was added to the mixture at room temperature, which was then extracted with ethyl acetate. After the organic layer was separated and washed with water and a saturated saline solution, it was dried with anhydrous sodium sulfate and concentrated under reduced pressure. The residue was purified by HPLC (C18, mobile phase: water/acetonitrile (10 mM ammonium bicarbonate system)). The resulting fraction was concentrated under reduced pressure to obtain the title compound (9.3 mg).

$^1$H NMR (300 MHz, DMSO-$d_6$) δ 1.33 (3H, t, J=7.3 Hz), 3.60 (2H, s), 4.05 (2H, q, J=7.3 Hz), 5.37 (2H, q, J=8.7 Hz), 6.39 (1H, t, J=6.8 Hz), 7.29-7.32 (1H, m), 7.36-7.47 (3H, m), 7.55-7.58 (1H, m), 7.75 (1H, dd, J=6.9, 2.0 Hz), 8.09-8.13 (1H, m), 8.24-8.32 (2H, m).

Example 7

3-[(1-Ethyl-1H-pyrazole-4-yl)methyl]-3' fluoro-6'-[(2R)-2-methylmorpholine-4-yl]-4'-(trifluoromethyl)-2H-[1,2'-bipyridine]-2-one A) 3-[(1-Ethyl-1H-pyrazole-4-yl)methyl]-3',6'-difluoro-4'-(trifluoromethyl)-2H-[1,2'-bipyridine]-2-one First, 3-((1-ethyl-1H-pyrazole-4-yl)methyl)pyridine-2(1H)-one (657 mg) was added to an N,N-dimethylacetamide (5 mL) solution of 2,3,6-trifluoro-4-(trifluoromethyl)pyridine (500 mg). Sodium hydride (60% content, 90 mg) was added to the mixture portionwise while maintaining a temperature of −20° C. or lower; the resulting mixture was heated to 0° C. and stirred for one hour at 0° C. After a saturated ammonium chloride aqueous solution was added to the mixture, it was diluted with water and extracted with ethyl acetate. After the organic layer was separated and washed with water and a saturated saline solution, it was dried with anhydrous sodium sulfate and concentrated under reduced pressure. The residue was purified by silica gel column chromatography (ethyl acetate/hexane) to obtain the title compound (373 mg).

MS: $[M+H]^+$ 385.1.

B) 3-[(1-Ethyl-1H-pyrazole-4-yl)methyl]-3'-fluoro-6'-[(2R)-2-methylmorpholine-4-yl]-4'-(trifluoromethyl)-2H-[1,2'-bipyridine]-2-one A mixture of 3-[(1-ethyl-1H-pyrazole-4-yl)methyl]-3',6'-difluoro-4'-(trifluoromethyl)-2H-[1,2'-bipyridine]-2-one (100 mg), (2R)-2-methlmoropholine hydrochloride (39.4 mg), cesium carbonate (93 mg), and DMSO (1 mL) was stirred for one hour at 100° C. The mixture was added to water and extracted with ethyl acetate. After the organic layer was separated and washed with water and a saturated saline solution, it was dried with anhydrous sodium sulfate and concentrated under reduced pressure. After the residue was purified by silica gel column chromatography (ethyl acetate/hexane), it was further purified by silica gel column chromatography (NH, ethyl acetate/hexane) to obtain the title compound (119 mg).

$^1$H NMR (300 MHz, $CDCl_3$) δ 1.24-1.28 (3H, m), 1.47 (3H, t, J=7.3 Hz), 2.64 (1H, dd, J=12.4, 10.5 Hz), 3.00 (1H, td, J=12.3, 3.6 Hz), 3.56-3.79 (4H, m), 3.88-4.07 (3H, m), 4.09-4.17 (2H, m), 6.22 (1H, t, J=7.0 Hz), 6.82 (1H, d, J=3.0 Hz), 7.17-7.24 (1H, m), 7.27-7.41 (3H, m).

Example 9

3-[(1-Ethyl-1H-pyrazole-4-yl)methyl]-1-{2-fluoro-5-[(2R)-2-methylmorpholine-4-yl]-3-(trifluoromethyl)phenyl}pyridine-2(1H)-one A) 5-Bromo-2-fluoro-1-nitro-3-(trifluoromethyl)benzene A mixture of 2-fluoro-1-nitro-3-(trifluoromethyl)benzene (4.90 g), NBS (5.01 g), TFA (20 mL), and concentrated sulfuric acid (30 mL) was stirred overnight at 60° C. After the mixture was added to ice water, the mixture was added to water and extracted with ethyl acetate. After the organic layer was separated and washed with a saturated sodium bicarbonate aqueous solution and a saturated saline solution, it was dried with anhydrous sodium sulfate and concentrated under reduced pressure. The residue was purified by silica gel column chromatography (ethyl acetate/hexane) to obtain the title compound (6.50 g).

$^1$H NMR (300 MHz, DMSO-$d_6$) δ 8.46 (1H, dd, J=5.3, 2.3 Hz), 8.70 (1H, dd, J=6.4, 2.3 Hz).

B) (2R)-4-[4-Fluoro-3-nitro-5-(trifluoromethyl)phenyl]-2-methylmorpholine

A mixture of 5-bromo-2-fluoro-1-nitro-3-(trifluoromethyl)benzene (1.00 g), (2R)-2-methylmorpholine hydrochloride (0.717 g), $Pd_2(dba)_3$ (0.318 g), sodium tert-butoxide (1.67 g), XPhos (0.331 g), and toluene (13 mL) was stirred for two hours at 110° C. under microwave irradiation. After the mixture was diluted with ethyl acetate and washed with water and a saturated saline solution, it was dried with anhydrous magnesium sulfate and concentrated under reduced pressure. The residue was purified by silica gel column chromatography (NH, ethyl acetate/hexane) to obtain the title compound (530 mg).

MS: $[M+H]^+$ 309.1.

C) 2-Fluoro-5-[(2R)-2-methylmorpholine-4-yl]-3-(trifluoromethyl)aniline

A mixture of (2R)-4-[4-fluoro-3-nitro-5-(trifluoromethyl)phenyl]-2-methylmorpholine (1.85 g), 10% palladium-carbon (0.319 g), and EtOH (60 mL) was stirred for two hours at room temperature in a hydrogen atmosphere at normal pressure. The catalyst was filtered out, and the filtrate was concentrated under reduced pressure. The residue was purified by silica gel column chromatography (NH, ethyl acetate/hexane) to obtain the title compound (1.67 g).

MS: $[M+H]^+$ 279.2.

D) (2R)-4-[4-Fluoro-3-nitro-5-(trifluoromethyl)phenyl]-2-methylmorpholine

Concentrated sulfuric acid (15 mL) and water (15 mL) were added to a mixture of 2-fluoro-5-[(2R)-2-methylmorpholine-4-yl]-3-(trifluoromethyl)aniline (3.1 g) and water (50 mL). A water (10 mL) solution of sodium nitrite (1.32 g) was dropped into the mixture at 0° C. After the mixture was stirred for one hour at 0° C., a water (10 mL) solution of potassium iodide (6.36 g) was dropped into the mixture at 0° C.

The mixture was heated to room temperature and stirred overnight at room temperature. The mixture was extracted with ethyl acetate. After the organic layer was separated and washed with a saturated sodium sulfite aqueous solution, it was dried with anhydrous sodium sulfate and concentrated under reduced pressure. The residue was purified by silica gel column chromatography (NH, ethyl acetate/hexane) to obtain the title compound (2.37 g).

MS: $[M+H]^+$ 390.0.

E) 3-[(1-Ethyl-1H-pyrazole-4-yl)methyl]-1-{2-fluoro-5-[(2R)-2-methylmorpholine-4-yl]-3-(trifluoromethyl)phenyl}pyridine-2(1H)-one A mixture of 3[(1-ethyl-1H-pyrazole-4-yl)methyl]pyridine-2(1H)-one (102 mg), (2R)-4-[4-fluoro-3-iodo-4-(trifluoromethyl)phenyl]-2-methylmorpholine (292 mg), copper (I) iodide (28.6 mg), quinoline-8-ol (21.8 mg), cesium carbonate (326 mg), and DMSO (4 mL) was heated for three hours at 120° C. under microwave irradiation. Ethyl acetate and water were added to the mixture, and after the organic layer was separated, it was dried with anhydrous sodium sulfate and concentrated under reduced pressure. The residue was purified by silica gel column chromatography (NH, ethyl acetate/hexane) to obtain the title compound (4.5 mg).

$^1$H NMR (300 MHz, $CDCl_3$) δ 1.25 (3H, d, J=6.0 Hz), 1.47 (3H, t, J=7.3 Hz), 2.53 (1H, dd, J=11 5, 10.4 Hz), 2.88 (1H, td, J=11.7, 3.8 Hz), 3.31-3.44 (2H, m), 3.67-3.82 (4H, m), 3.97-4.06 (1H, m), 4.13 (2H, q, J=7.2 Hz), 6.20 (1H, t, J=7.0 Hz), 7.01 (1H, dd, J=5.7, 3.0 Hz), 7.09-7.17 (2H, m), 7.21 (1H, dt, J=6.8, 0.9 Hz), 7.34 (1H, s), 7.39 (1H, s).

Example 20

1-{3-Cyclopropyl-2-fluoro-5-[(2R)-2-methylmorpholine-4-yl]phenyl}-3-[(1-ethyl-1H-pyrazole-4-yl)methyl]pyridine-2(1H)-one A) Ethyl 1-ethyl-1H-pyrazole-4-carboxylate A mixture of potassium carbonate (197 g), ethyl 1H-pyrazole-4-carboxylate (100 g), ethyl iodide (122 g), and DMF (200 mL) was stirred overnight at room temperature. The mixture was added to water at room temperature and extracted with ethyl acetate. After the organic layer was separated and washed with water and a saturated saline solution, it was dried with anhydrous magnesium sulfate and concentrated under reduced pressure to obtain the title compound (121 g).

$^1$H NMR (300 MHz, DMSO-$d_6$) δ 1.26 (3H, t, J=7.2 Hz), 1.37 (3H, t, J=7.2 Hz), 4.12-4.27 (4H, m), 7.84 (1H, s), 8.33 (1H, s).

B) (1-Ethyl-1H-pyrazole-4-yl)methanol

A mixture of ethyl 1-ethyl-1H-pyrazole-4-carboxylate (48.0 g) and THF (100 mL) was dropped into a mixture of lithium aluminum hydride (16.3 g) and THF (400 mL) at 0-10° C., and the mixture was stirred for one hour at room temperature. After the mixture was diluted with THF (150 mL) and cooled to 0° C., sodium sulfate decahydrate (110 g) was added at 0-10° C. and stirred for one hour at room temperature. The insoluble matter was filtered out, and the filtrate was distilled out under reduced pressure to obtain the title compound (29.9 g).

$^1$H NMR (300 MHz, DMSO-$d_6$) δ 1.33 (3H, t, J=7.3 Hz), 4.07 (2H, q, J=7.2 Hz), 4.32 (2H, d, J=5.3 Hz), 4.77 (1H, t, J=5.5 Hz), 7.32 (1H, s), 7.59 (1H, s).

C) 4-(Chloromethyl)-1-ethyl-1H-pyrazole hydrochloride

Thionyl chloride (4.39 g) was added to a mixture of (1-ethyl-1H-pyrazole-4-yl)methanol (2.33 g) and acetonitrile (20 mL) at room temperature, and the mixture was stirred overnight at the same temperature. The mixture was concentrated to obtain the title compound (3.23 g).

$^1$H NMR (300 MHz, DMSO-$d_6$) δ 1.34 (3H, t, J=7.2 Hz), 4.10 (2H, q, J=7.4 Hz), 4.69 (2H, s), 7.50 (1H, s), 7.85 (1H, s), 12.32 (1H, m).

D) 3-[(1-Ethyl-1H-pyrazole-4-yl)methyl]-2-methoxypyridine

A mixture of 4-(chloromethyl)-1-ethyl-1H-pyrazole hydrochloride (2.87 g), cesium carbonate (20.7 g), $PdCl_2$ (dppf) (2.32 g), (2-methoxypyridine-3-yl)boronic acid (3.15 g), DME (25 ml), and water (2.5 mL) was stirred for one hour at 110° C. in an argon atmosphere. The mixture was diluted with water and extracted with ethyl acetate. After the organic layer was separated and washed with water and a saturated saline solution, it was dried with anhydrous sodium sulfate and concentrated under reduced pressure. The residue was purified by silica gel column chromatography (NH, ethyl acetate/hexane) to obtain the title compound (2.88 g).

MS: $[M+H]^+$ 218.0.

E) 3-[(1-Ethyl-1H-pyrazole-4-yl)methyl]-pyridine-2(1H)-one

Pyridine hydrochloride (1.61 g) was added to a DMF (3 mL) solution of 3-[(1-ethyl-1H-pyrazole-4-yl)methyl]-2-methoxypyridine. The mixture was stirred for 16 hours at 90° C. After the mixture was concentrated under reduced pressure, the residue was purified by HPLC (C18, mobile phase: water/acetonitrile (10 mM ammonium bicarbonate system)). The resulting fraction was concentrated under reduced pressure to obtain the title compound (194 mg).

MS: $[M+H]^+$ 204.0.

F) 2-Bromo-1-fluoro-4-iodobenzene

A water (20 mL) solution of sodium nitrite (2.00 g) was slowly added to a mixture of 3-bromo-4-fluoroaniline (5 g) and concentrated hydrochloric acid (16.5 mL) at 0° C. After the mixture was stirred for 30 minutes at 0° C., a water (20 mL) solution of potassium iodide (13.1 g) was added at 0° C. and stirred for three hours at room temperature. Water was added to the mixture and extracted with ethyl acetate. After the organic layer was separated, it was washed with a saturated saline solution, dried with anhydrous sodium sulfate, and concentrated under reduced pressure. The residue was purified by silica gel column chromatography (ethyl acetate/hexane) to obtain the title compound (6.90 g).

$^1$H NMR (300 MHz, DMSO-$d_6$) δ 7.21 (1H, t, J=8.8 Hz), 7.77 (1H, ddd, J=8.7, 4.7, 2.1 Hz), 8.02-8.13 (1H, m).

G) (2R)-4-(3-Bromo-4-fluorophenyl)-2-methylmorpholine

A mixture of 2-bromo-1-fluoro-4-iodobenzene (1 g), (2R)-2-methylmorpholine hydrochloride (0.457 g), palladium(II) acetate (0.0750 g), BINAP (0.207 g), cesium carbonate (3.25 g), and toluene (30 mL) was stirred for one hour at 120° C. The mixture was filtered using Celite®, and the filtrate was concentrated under reduced pressure. The residue was purified by silica gel column chromatography (ethyl acetate/hexane) to obtain the title compound (0.56 g).

MS: $[M+H]^+$ 274.1.

H) (2R)-4-(3-Cyclopropyl-4-fluorophenyl)-2-methylmorpholine $Pd_2(dba)_3$ (84 mg) was added to a mixture of (2R)-4-(3-bromo-4-fluorophenyl)-2-methylmorpholine (250 mg), cyclopropylboronic acid (157 mg), SPhos (74.9 mg), sodium carbonate (193 mg), and DME (1 mL) at room temperature in an argon atmosphere. The mixture was stirred for one hour at 120° C. in a sealed tube under an argon atmosphere. The mixture was purified by silica gel column chromatography (NH, ethyl acetate/hexane) to obtain the title compound (177 mg).

MS: $[M+H]^+$ 236.2.

I) (2R)-4-[3-Cyclopropyl-4-fluoro-5-(4,4,5,5-tetramethyl-1,3,2-dioxaborolane-2-yl)phenyl]-2-methylmorpholine A mixture of (2R)-4-(3-cyclopropyl-4-fluorophenyl)-2-methylmorpholine (343 mg), 4,4,4',4',5,5,5',5'-octamethyl-2,2'-dioxaborolane (407 mg), di-p-methoxobis(1,5-cyclooctadiene)diiridium(I) (19.3 mg), dbbpy (15.7 mg), and 2-methoxy-2-methylpropane (3 ml) was heated for one hour at 80° C. under microwave irradiation. The mixture was filtered using Celite®, and the filtrate was distilled out under reduced pressure to obtain the title compound (527 mg).

MS: $[M+H]^+$ 362.3.

J) 1-{3-Cyclopropyl-2-fluoro-5-[(2R)-2-methylmorpholine-4-yl]phenyl}-3-[(1-ethyl-1H-pyrazole-4-yl)methyl]pyridine-2(1H)-one A mixture of (2R)-4-[3-cyclopropyl-4-fluoro-5-(4,4,5,5-tetramethyl-1,3,2-dioxaborolane-2-yl)phenyl]-2-methylmorpholine (711 mg), 3-[(1-ethyl-1H-pyrazole-4-yl)methyl]pyridine-2(1H)-one (200 mg), copper(II) acetate (357 mg), pyridine (311 mg), and acetonitrile (10 mL) was stirred for 12 hours at 40° C. and then for 10 hours at 60° C. Next, (2R)-4-[3-cyclopropyl-4-fluoro-5-(4,4,5,5-tetramethyl-1,3,2-dioxaborolane-2-yl)phenyl]-2-methylmorpholine (527 mg) was added to the mixture, and the mixture was stirred for 13 hours at 60° C. The mixture was filtered using Celite®, and the filtrate was concentrated under reduced pressure. The residue was purified by silica gel column chromatography (NH, ethyl acetate/hexane). The resulting fraction was concentrated under reduced pressure, and the resulting residue was crystallized from ethyl acetate/hexane to obtain the title compound (131 mg).

$^1$H NMR (300 MHz, DMSO-$d_6$) δ 0.75-0.88 (2H, m), 0.92-1.03 (2H, m), 1.12 (3H, d, J=6.0 Hz), 1.33 (3H, t, J=7.3 Hz), 1.98-2.07 (, m), 2.26 (1H, t, J=11.3 Hz), 2.53-2.64 (1H, m), 3.47 (1H, br d, J=11.3 Hz), 3.52-3.63 (5H, m), 3.87 (1H, dd, J=11.3, 2.3 Hz), 4.06 (2H, q, J=7.4 Hz), 6.24 (1H, t, J=6.8 Hz), 6.54 (1H, dd, J=5.8, 2.8 Hz), 6.74 (1H, dd, J=6.0, 3.0 Hz), 7.22-7.29 (2H, m), 7.47 (1H, dd, J=6.8, 1.9 Hz), 7.54 (1H, s).

Example 23

1-{3-Bromo-2-fluoro-5-[(oxane-4-yl)oxy]phenyl}-3-[(1-ethyl-1H-pyrazole-4-yl)methyl]pyridine-2(1H)-one A) 4-(3-Bromo-4-fluorophenoxy)tetrahydro-2H-pyran After ethyl azodicarboxylate (5.74 ml) was dropped into a mixture of tetrahydro-2H-pyran-4-ol (1.07 g), 4-fluoro-3-(trifluoromethyl)phenol (2 g), triphenylphosphine (3.30 g), and THF (20 mL) at room temperature, the mixture was stirred overnight. After the mixture was concentrated under reduced pressure, the residue was purified by silica gel column chromatography (ethyl acetate/hexane) to obtain the title compound (2.3 g).

$^1$H NMR (300 MHz, DMSO-$d_6$) δ 1.55 (2H, dtd, J=13.3, 9.0, 4.1 Hz), 1.89-1.97 (2H, m), 3.46 (2H, ddd, J=11.9, 9.4, 2.8 Hz), 3.83 (2H, dt, J=11.7, 4.5 Hz), 4.57 (1H, tt, J=8.6, 4.2 Hz), 6.99-7.06 (1H, m), 7.23-7.38 (2H, m).

B) 1-{3-Bromo-2-fluoro-5-[(oxane-4-yl)oxy]phenyl}-3-[(1-ethyl-1H-pyrazole-4-yl)methyl]pyridine-2(1H)-one Di-p-methoxobis(1,5-cyclooctadiene)diiridium(I) (185 mg) was added to a degassed THF (2 mL) solution of 4,4,4',4',5,5,5',5'-octamethyl-2,2'-bi(1,3,2-dioxaborolane) (9.64 mg) at room temperature in an argon atmosphere. Next, dbbpy (7.8 mg) was added to the mixture at room temperature in an argon atmosphere. A mixture of 4-(3-bromo-4-fluorophenoxy)tetrahydro-2H-pyran (200 mg) and THF (1 mL) was added to the mixture at room temperature in an argon atmosphere, and the mixture was stirred for three hours at 40° C. in an argon atmosphere. The mixture was concentrated under reduced pressure. A mixture of the resulting residue (292 mg), 3-[(1-ethyl-1H-pyrazole-4-yl)methyl]pyridine-2(1H)-one (59.2 mg), copper(II) acetate (79 mg), pyridine (0.047 ml), and acetonitrile (3 mL) was stirred for 12 hours at 80° C. After the mixture was concentrated under reduced pressure, the residue was purified by silica gel column chromatography (ethyl acetate/hexane) to obtain the title compound (5.60 mg).

$^1$H NMR (300 MHz, DMSO-$d_6$) δ 1.33 (3H, t, J=7.3 Hz), 1.50-1.62 (2H, m), 1.89-1.98 (2H, m), 3.38-3.56 (4H, m), 3.84 (2H, dt, J=11.6, 4.2 Hz), 4.02-4.10 (2H, m), 4.64 (1H, dt, J=8.8, 4.6 Hz), 6.28 (1H, t, J=6.8 Hz), 7.15-7.32 (3H, m), 7.46 (1H, dd, J=5.3, 3.0 Hz), 7.52-7.56 (2H, m).

Example 27

3-[(1-Ethyl-H n-pyrazole-4-yl)methyl]-1-{2-fluoro-5-[(2R)-2-methylmorpholine-4-yl]-3-(propane-2-yl)phenyl}pyridine-2(1H)-one A) 2-Fluoro-5-[(2R)-2-methylmorpholine-4-yl]phenol A mixture of 5-bromo-2-fluorophenol (5.00 g), (2R)-2-methylmorpholine hydrochloride (5.40 g), palladium(II) acetate (0.588 g), BINAP (1.63 g), sodium tert-butoxide (10.1 g), and toluene (250 mL) was stirred for four hours at 120° C. in a nitrogen atmosphere. The mixture was filtered using Celite®, and the filtrate was concentrated under reduced pressure. The residue was purified by silica gel column chromatography (ethyl acetate/hexane) to obtain the title compound (1.10 g).

MS: $[M+H]^+$ 212.1

B) 2-Fluoro-5-[(2R)-2-methylmorpholine-4-yl]phenyl trifluoromethanesulfonate

A toluene (4 mL) solution of trifluoromethanesulfonic acid anhydride (1.12 mL) was dropped into a mixture of 2-fluoro-5-[(2R)-2-methylmorpholine-4-yl]phenol (1.08 g) and pyridine (8 mL) at 0° C. over the course of 5 minutes. After the mixture was heated to room temperature and stirred overnight at the same temperature, it was concentrated under reduced pressure. The residue was purified by silica gel column chromatography (ethyl acetate/hexane) to obtain the title compound (1.30 g).

MS: $[M+H]^+$ 344.0.

C) (2R)-4-[4-Fluoro-3-(prop-1-ene-2-yl)phenyl]-2-methylmorpholine

A mixture of 2-fluoro-5-[(2R)-2-methylmorpholine-4-yl] phenyl trifluoromethanesulfonate (1.00 g), 4,4,5,5-tetramethyl-2-(prop-1-ene-2-yl)-1,3,2-dioxabrolane (0.979 g), $PdCl_2(dppf)\cdot CH_2Cl_2$ (0.238 g), sodium carbonate (0.617 g), DME (10 mL), and water (3 mL) was stirred for 12 hours at 120° C. in a nitrogen atmosphere. Water was added to the mixture and extracted with ethyl acetate. The organic layer was separated, dried with anhydrous magnesium sulfate, and concentrated under reduced pressure. The residue was purified by silica gel column chromatography (ethyl acetate/hexane) to obtain the title compound (0.145 g).

MS: [M+H]236.1.

D) (2R)-4-[4-Fluoro-3-(propane-2-yl)phenyl]-2-methylmorpholine

A mixture of (2R)-4-[4-fluoro-3-(prop-1-ene-2-yl)phenyl]-2-methylmorpholine (145 mg), 10% palladium-carbon (30 mg), and EtOH (8 mL) was stirred for four hours at room temperature in a hydrogen atmosphere. The catalyst was filtered out, and the filtrate was concentrated under reduced pressure to obtain the title compound (144 mg).

MS: $[M+H]^+$ 238.2.

E) 3-[(1-Ethyl-1H-pyrazole-4-yl)methyl]-1-{2-fluoro-5-[(2R)-2-methylmorpholine-4-yl]-3-(propane-2-yl)phenyl}pyridine-2(1H)-one A mixture of (2R)-4-[4-fluoro-3-(propane-2-yl)phenyl]-2-methylmorpholine (144 mg), 4,4,4',4',5,5,5',5'-octamethyl-2,2'-bi-1,3,2-dioxaborolane (169 mg), di-p-methoxobis(1,5-cyclooctadiene)diiridium(I) (8.04 mg), dbbpy (6.51 mg), and 2-methoxy-2-methylpropane (2 mL) was irradiated with microwaves for one hour at 80° C. The mixture was filtered using Celite®, and the filtrate was concentrated under reduced pressure. Acetonitrile (2 mL) was added to the resulting residue (solution A). A mixture of solution A (1 mL), 3-[(1-ethyl-1H-pyrazole-4-yl)methyl]pyridine-2(1H)-one (62.0 mg), copper(II) acetate (111 mg), and pyridine (97.0 mg) was stirred for 12 hours at 60° C. Solution A (1 mL) was further added to the mixture and stirred for 12 more hours at 60° C. The mixture was filtered, and the filtrate was concentrated under reduced pressure. After the residue was purified by silica gel column chromatography (NH, ethyl acetate/hexane), it was further purified by silica gel column chromatography (ethyl acetate/hexane) to obtain the title compound (19.0 mg).

$^1H$ NMR (400 MHz, $CDCl_3$) δ 1.22-1.25 (3H, m), 1.28 (6H, d, J=7.0 Hz), 1.47 (3H, t, J=7.3 Hz), 2.48 (1H, t, J=10.9 Hz), 2.78-2.86 (1H, m), 3.21-3.39, (3H, m), 3.69-3.81 (4H, m), 3.95-4.03 (1H, m), 4.13 (2H, q, J=7.3 Hz), 6.16 (1H, t, J=6.8 Hz), 6.66 (1H, dd, J=5.6, 2.9 Hz), 6.85 (1H, dd, J=5.3, 2.9 Hz), 7.17 (2H, br t, J=8.1 Hz), 7.35 (1H, s), 7.40 (1H, s).

Example 31

1-{3-Cyclopropyl-S-[(2R)-2-methylmorpholine-4-yl]phenyl}-3-[(1-ethyl-1H-pyrazole-4-yl)methyl]-6-fluoropyridine-2(1H)-one A) 3-[(1-Ethyl-1H-pyrazole-4-yl)methyl]-6-fluoro-2-methoxypyridine A sodium methoxide/methanol solution (28% content, 3.2 g) was added to a mixture of 2,6-difluoro-3-iodopyridine (4.0 g) and methanol (40 mL) at 0° C. The mixture was stirred for 12 hours at room temperature and concentrated under reduced pressure. The residue was purified by silica gel column chromatography (ethyl acetate/hexane) to obtain a mixture of 6-fluoro-3-iodo-2-methoxypyridine and 2-fluoro-3-iodo-6-methoxypyridine (4.0 g). A mixture of the resulting mixture (4.0 g), 4,4,4',4',5,5,5',5'-octamethyl-2,2'-bi-1,3,2-dioxaborolane (6.0 g), $PdCl_2(dppf)\cdot CH_2Cl_2$ (0.65 g), potassium acetate (4.65 g), and DME (80 mL) was stirred for 36 hours at 100° C. The mixture was filtered using Celite®, and the filtrate was concentrated under reduced pressure to obtain a mixture of 6-fluoro-2-methoxy-3-(4,4,5,5-tetramethyl-1,3,2-dioxaborolane-2-yl)pyridine and 2-fluoro-6-methoxy-3-(4,4,5,5-tetramethyl-1,3,2-dioxaborolane-2-yl)pyridine. A mixture of the resulting mixture, 4-(chloromethyl)-1-ethyl-1H-pyrazole hydrochloride (4.3 g), $PdCl_2(dppf)\cdot CH_2Cl_2$ (1.3 g), cesium carbonate (25.7 g), DME (70 mL), and water (15 mL) was stirred for four hours at 90° C. in a nitrogen atmosphere. Water was added to the mixture, and the resulting mixture was extracted with ethyl acetate. The organic layer was separated, dried with anhydrous magnesium sulfate, and concentrated under reduced pressure. The residue was purified by silica gel column chromatography (NH, ethyl acetate/hexane) to obtain a mixture of the title compound and 3-[(1-ethyl-1H-pyrazole-4-yl)methyl]-2-fluoro-6-methoxypyridine (2.3 g).

MS: $[M+H]^+$ 236.1.

B) 3-[(1-Ethyl-1H-pyrazole-4-yl)methyl]-6-fluoropyridine-2(1H)-one

A mixture of the mixture of 3-[(1-ethyl-1H-pyrazole-4-yl)methyl]-6-fluoro-2-methoxypyridine and 3-[(1-ethyl-1H-pyrazole-4-yl)methyl]-2-fluoro-6-methoxypyridine obtained in step A (1.0 g), trimethylsilylchloride (2.31 g), sodium iodide (0.64 g), and acetonitrile (15 mL) was irradiated with microwaves for four hours at 180° C. Water was added to the mixture, which was then extracted with ethyl acetate. The organic layer was separated, dried with anhydrous magnesium sulfate, and concentrated under reduced pressure. The residue was purified by silica gel column chromatography (ethyl acetate/hexane) to obtain a mixture of the title compound and 5-[(1-ethyl-1H-pyrazole-4-yl) methyl]-6-fluoropyridine-2(1H)-one (0.25 g).

MS: $[M+H]^+$ 222.1.

C) (2R)-4-(3-Chlorophenyl)-2-methylmorpholine

A mixture of 1-chloro-3-iodobenzene (5 g), (2R)-2-methylmorpholine hydrochloride (3.2 g), palladium(II) acetate (0.47 g), BINAP (1.3 g), sodium tert-butoxide (8.1 g), and toluene (250 mL) was stirred for four hours at 120° C. in a nitrogen atmosphere. The mixture as filtered using celite, and the filtrate was concentrated under reduced pressure.

The residue was purified by silica gel column chromatography (ethyl acetate/hexane) to obtain the title compound (1.8 g).

MS: $[M+H]^+$ 212.1.

D) (2R)-4-(3-Cyclopropylphenyl)-2-methylmorpholine

A mixture of (2R)-4-(3-chlorophenyl)-2-methylmorpholine (1.80 g), cyclopropylboronic acid (2.19 g), palladium (II) acetate (0.19 g), a tricyclohexylphosphine/toluene solution (20% content, 2.98 g), tripotassium phosphate (8.1 g), toluene (75 mL), and water (15 mL) was stirred for 12 hours at 120° C. in a nitrogen atmosphere. The mixture was filtered, and the filtrate was concentrated under reduced pressure. After the residue was purified by silica gel column chromatography (ethyl acetate/hexane), it was further purified by HPLC (C18, mobile phase: water/acetonitrile (10 mM ammonium bicarbonate system)). The resulting fraction was concentrated under reduced pressure to obtain the title compound (0.83 g).

MS: $[M+H]^+$ 218.2.

E) 1-{3-Cyclopropyl-5-[(2R)-2-methylmorpholine-4-yl]phenyl}-3-[(1-ethyl-1H-pyrazole-4-yl)methyl]-6-fluoropyridine-2(1H)-one A mixture of (2R)-4-(3-cyclopropylphenyl)-2-methylmorpholine (0.83 g), 4,4,4',4',5,5,5',5'-octamethyl-2,2'-dioxaborolane (1.07 g), di-p-methoxobis(1,5-cyclooctadiene) diiridium(I) (50.6 mg), dbbpy (41.0 mg), and 2-methoxy-2-methylpropane (12 mL) was heated for one hour at 80° C. under microwave irradiation. Next, 4,4,4',4',5,5,5',5'-octamethyl-2,2'-bi-1,3,2-dioxaborolane (0.5 g), di-p-methoxobis (1,5-cyclooctadiene)diiridium(I) (50.6 mg), and dbbpy (41.0 mg) were added to the mixture and stirred for 12 hours at 40° C. in a nitrogen atmosphere. The mixture was filtered using Celite®, and the filtrate was concentrated under reduced pressure. Copper (II) acetate (0.52 g) was added to a mixture of the resulting residue, the mixture of 3-[(1-ethyl-1H-pyrazole-4-yl)methyl]-6-fluoropyridine-2(1H)-one and 5-[(1-ethyl-1H-pyrazole-4-yl)methyl]-6-fluoropyridine-2 (1H)-one (0.21 g), pyridine (0.31 mL), and acetonitrile (2 mL) at room temperature. After the mixture was stirred for 48 hours at 40° C., it was stirred for 72 hours at room temperature. The mixture was filtered, and the filtrate was concentrated under reduced pressure. After the residue was purified by silica gel column chromatography (ethyl acetate/hexane), it was purified by HPLC ($C_{18}$, mobile phase: water/acetonitrile (0.1% TFA-containing system)). The resulting fraction was concentrated under reduced pressure to obtain the title compound (4.8 mg).

$^1H$ NMR (300 MHz, $CDCl_3$) δ 0.70-0.73 (2H, m), 0.92-0.98 (2H, m), 1.23 (3H, d, J=6.24 Hz), 1.47 (3H, t, J=7.2 Hz), 1.84-1.93 (1H, m), 2.52 (1H, t, J=10.9 Hz), 2.86 (1H, td, J=11.9, 3.4 Hz), 3.42 (2H, br t, J=12.8 Hz), 3.66 (2H, s), 3.68-3.80 (2H, m), 3.93-4.03 (1H, m), 4.08-4.18 (2H, m), 5.82 (1H, dd, J=7.7, 4.3 Hz), 6.42-6.45 (11H, m), 6.53 (1H, t, J=2.1 Hz), 6.70-6.73 (1H, m), 7.18 (1H, dd, J=8.5, 7.7 Hz), 7.35 (1H, s), 7.39 (1H, s).

The compounds of the examples are shown in Table 1. In Table 1, MS represents actual measurements. The compounds of Table 1 were produced in accordance with the methods described in the examples above or similar methods.

TABLE 1

| Example No. | IUPAC Name | Structure | Salt | MS |
|---|---|---|---|---|
| 1 | 3-[(1-ethyl-1H-pyrazol-4-yl)methyl]-6'-(4-fluorophenyl)-4'-(trifluoromethyl)-2H-[1,2'-bipyridin]-2-one | 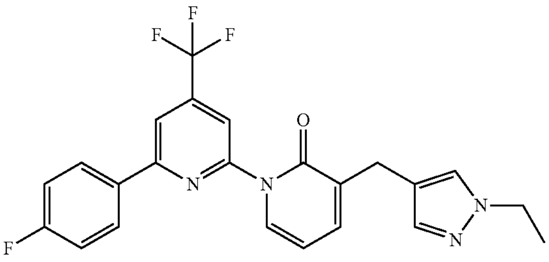 [SMILES: CCn1cc(Cc2cccn(-c3cc(C(F)(F)F)cc(-c4ccc(F)cc4)n3)c2=O)cn1] | | 443.2 |
| 2 | 3-[(1-ethyl-1H-pyrazol-4-yl)methyl]-6'-(4-fluorophenyl)-2-oxo-4'-(trifluoromethyl)-2H-[1,2'-bipyridine]-3'-carbonitrile | 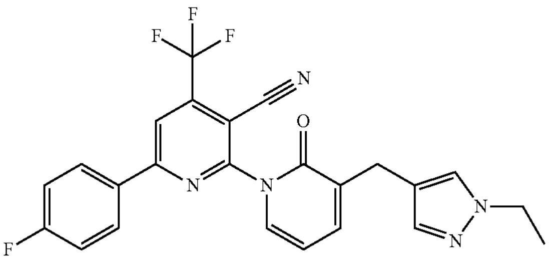 [SMILES: CCn1cc(Cc2cccn(-c3nc(-c4ccc(F)cc4)cc(C(F)(F)F)c3C#N)c2=O)cn1] | | 468.2 |

TABLE 1-continued

| Example No. | IUPAC Name | Structure | Salt | MS |
|---|---|---|---|---|
| 3 | 3-[(1-ethyl-1H-pyrazol-4-yl)methyl]-6'-(4-fluorophenyl)-2-oxo-4'-(2,2,2-trifluoroethoxy)-2H-[1,2'-bipyridine]-3'-carbonitrile | 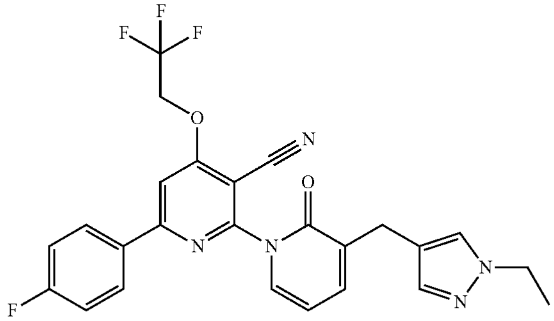 [SMILES: CCn1cc(Cc2cccn(-c3nc(-c4ccc(F)cc4)cc(OCC(F)(F)F)c3C#N)c2=O)cn1] | | 498.1 |
| 4 | 4'-(2,2-difluoroethoxy)-3-[(1-ethyl-1H-pyrazol-4-yl)methyl]-6'-(4-fluorophenyl)-2-oxo-2H-[1,2'-bipyridine]-3'-carbonitrile | 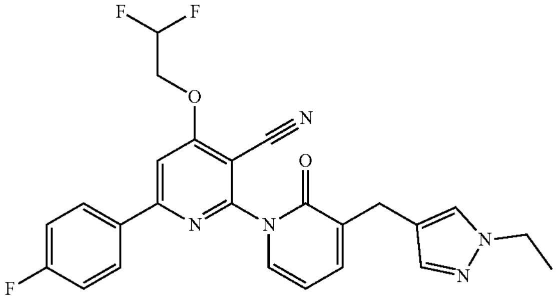 [SMILES: CCn1cc(Cc2cccn(-c3nc(-c4ccc(F)cc4)cc(OCC(F)F)c3C#N)c2=O)cn1] | | 480.1 |
| 5 | 3-[(1-ethyl-1H-pyrazol-4-yl)methyl]-6'-(4-fluorophenyl)-6-methyl-2-oxo-4'-(trifluoromethyl)-2H-[1,2'-bipyridine]-3'-carbonitrile | 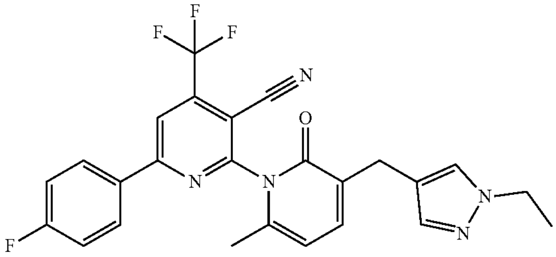 [SMILES: CCn1cc(Cc2ccc(C)n(-c3nc(-c4ccc(F)cc4)cc(C(F)(F)F)c3C#N)c2=O)cn1] | | 482.1 |
| 6 | 4'-(difluoromethyl)-3-[(1-ethyl-1H-pyrazol-4-yl)methyl]-6'-(4-fluorophenyl)-2-oxo-2H-[1,2'-bipyridine]-3'-carbonitrile | 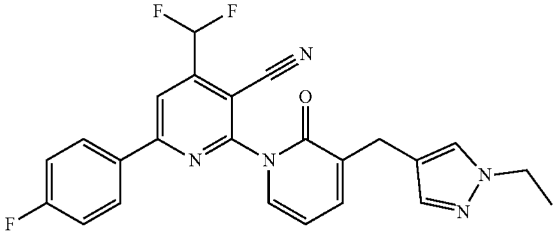 [SMILES: CCn1cc(Cc2cccn(-c3nc(-c4ccc(F)cc4)cc(C(F)F)c3C#N)c2=O)cn1] | | 450.2 |
| 7 | 3-[(1-ethyl-1H-pyrazol-4-yl)methyl]-3'-fluoro-6'-[(2R)-2-methylmorpholin-4-yl]-4'-(trifluoromethyl)-2H-[1,2'-bipyridin]-2-one | 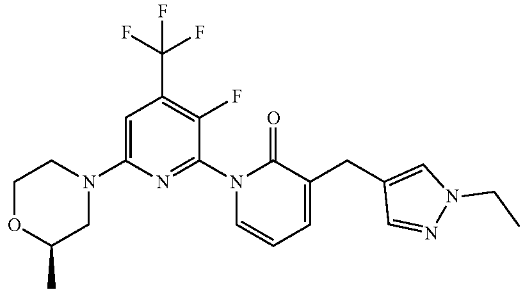 [SMILES: CCn1cc(Cc2cccn(-c3nc(N4CCO[C@H](C)C4)cc(C(F)(F)F)c3F)c2=O)cn1] | | 466.2 |

TABLE 1-continued

| Example No. | IUPAC Name | Structure | Salt | MS |
|---|---|---|---|---|
| 8 | 3-[(1-ethyl-1H-pyrazol-4-yl)methyl]-5'-methyl-6'-[(2R) 2-methylmorpholin-4-yl]-4'-(trifluoromethyl)-2H-[1,2'-bipyridin]-2-one | 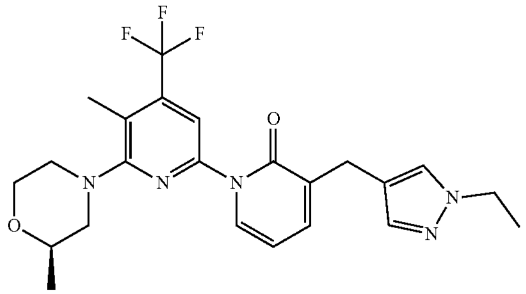 [SMILES: CCn1cc(Cc2cccn(-c3cc(C(F)(F)F)c(C)c(N4CCO[C@H](C)C4)n3)c2=O)cn1] | | 462.2 |
| 9 | 3-[(1-ethyl-1H-pyrazol-4-yl)methyl]-1-{2-fluoro-5-[(2R)-2-methylmorpholin-4-yl]-3-(trifluoromethyl)phenyl} pyridin-2(1H)-one | 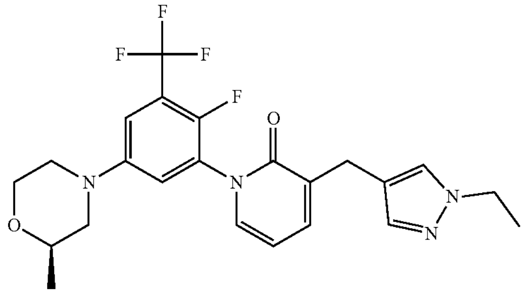 [SMILES: CCn1cc(Cc2cccn(-c3cc(N4CCO[C@H](C)C4)cc(C(F)(F)F)c3F)c2=O)cn1] | | 465.2 |
| 10 | 6'-[2-(difluoromethyl)morpholin-4-yl]-3-[(1-ethyl-1H-pyrazol-4-yl)methyl]-3'-fluoro-4'-(trifluoromethyl)-2H-[1,2'-bipyridin]-2-one | 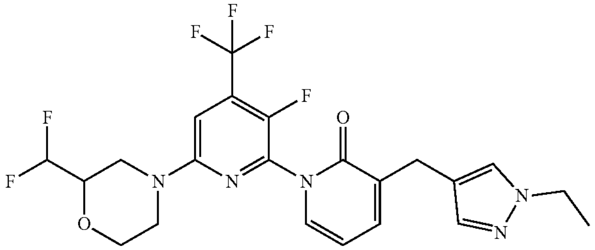 [SMILES: CCn1cc(Cc2cccn(-c3nc(N4CCOC(C(F)F)C4)cc(C(F)(F)F)c3F)c2=O)cn1] | | 502.2 |
| 11 | 3-[(1-ethyl-1H-pyrazol-4-yl)methyl]-3'-fluoro-4-methyl-6'-[(2R)-2-methylmorpholin-4-yl]-4'-(trifluoromethyl)-2H-[1,2'-bipyridin]-2-one | 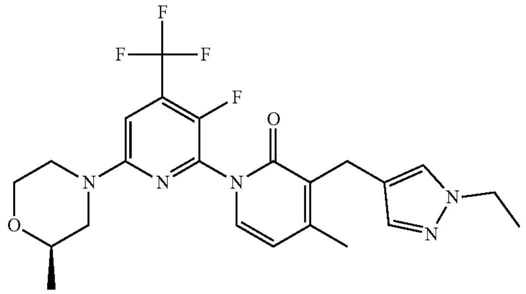 [SMILES: CCn1cc(Cc2c(C)ccn(-c3nc(N4CCO[C@H](C)C4)cc(C(F)(F)F)c3F)c2=O)cn1] | | 479.9 |
| 12 | 3-[(1-ethyl-1H-pyrazol-4-yl)methyl]-3'-fluoro-5-methyl-6'-[(2R)-2-methylmorpholin-4-yl]-4'-(trifluoromethyl)-2H-[1,2'-bipyridin]-2-one | 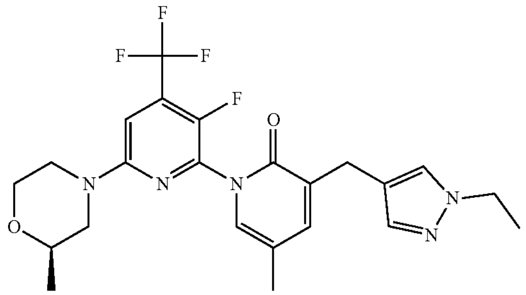 [SMILES: CCn1cc(Cc2cc(C)cn(-c3nc(N4CCO[C@H](C)C4)cc(C(F)(F)F)c3F)c2=O)cn1] | | 480.2 |

TABLE 1-continued

| Example No. | IUPAC Name | Structure | Salt | MS |
|---|---|---|---|---|
| 13 | 6'-[2-(difluoromethyl)morpholin-4-yl]-3-[(1-ethyl-1H-pyrazol-4-yl)methyl]-3'-fluoro-4'-(trifluoromethyl)-2H-[1,2'-bipyridin]-2-one (optical isomers) | 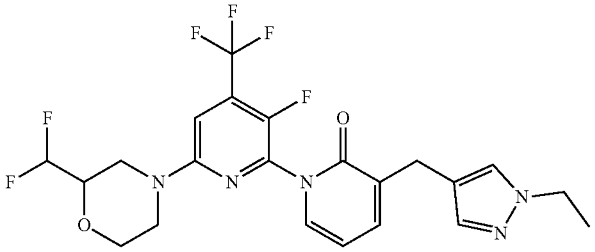 [SMILES: CCn1cc(Cc2cccn(-c3nc(N4CCOC(C(F)F)C4)cc(C(F)(F)F)c3F)c2=O)cn1] | | 501.9 |
| 14 | 6'-[2-(difluoromethyl)morpholin-4-yl]-3-[(1-ethyl-1H-pyrazol-4-yl)methyl]-3'-fluoro-4'-(trifluoromethyl)-2H-[1,2'-bipyridin]-2-one (optical isomers) | 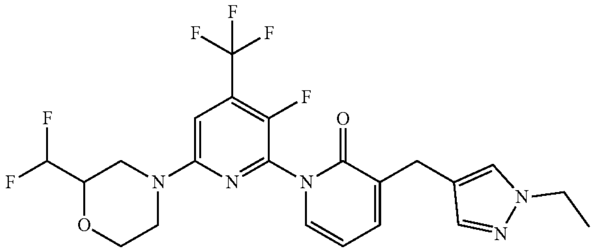 [SMILES: CCn1cc(Cc2cccn(-c3nc(N4CCOC(C(F)F)C4)cc(C(F)(F)F)c3F)c2=O)cn1] | | 501.9 |
| 15 | 3-[(1-ethyl-1H-pyrazol-4-yl)methyl]-3'-fluoro-6'-[(oxan-4-yl)oxy]-4'-(trifluoromethyl)-2H-[1,2'-bipyridin]-2-one | 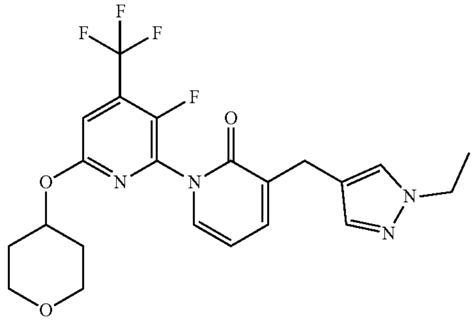 [SMILES: CCn1cc(Cc2cccn(-c3nc(OC4CCOCC4)cc(C(F)(F)F)c3F)c2=O)cn1] | | 467.1 |
| 16 | 3-[(1-ethyl-1H-pyrazol-4-yl)methyl]-1-[4-{[(1-fluorocyclobutyl)methyl]amino}-6-(trifluoromethyl)pyrimidin-2-yl]pyridin-2(1H)-one | 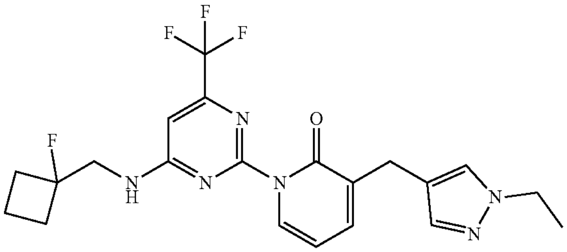 [SMILES: CCn1cc(Cc2cccn(-c3nc(NCC4(F)CCC4)cc(C(F)(F)F)n3)c2=O)cn1] | | 451.1 |
| 17 | 1-[4-{[(3,3-difluorocyclobutyl)methyl]amino}-6-(trifluoromethyl)pyrimidin-2-yl]-3-[(1-ethyl-1H-pyrazol-4-yl)methyl]pyridin-2(1H)-one | 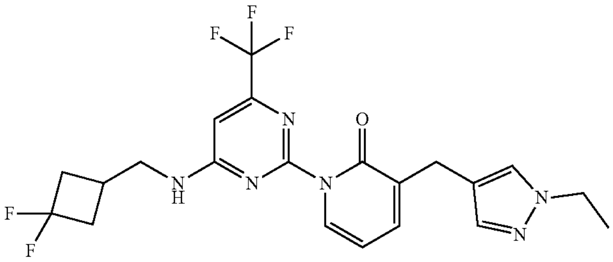 [SMILES: CCn1cc(Cc2cccn(-c3nc(NCC4CC(F)(F)C4)cc(C(F)(F)F)n3)c2=O)cn1] | | 469.0 |

TABLE 1-continued

| Example No. | IUPAC Name | Structure | Salt | MS |
|---|---|---|---|---|
| 18 | 1-[4-{[(3,3-difluorocyclobutyl)methyl](methyl)amino}-6-(trifluoromethyl)pyrimidin-2-yl]-3-[(1-ethyl-1H-pyrazol-4-yl)methyl]pyridin-2(1H)-one | 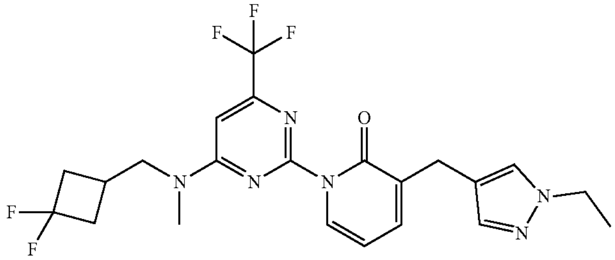 [SMILES: CCn1cc(Cc2cccn(-c3nc(N(C)CC4CC(F)(F)C4)cc(C(F)(F)F)n3)c2=O)cn1] | | 483.1 |
| 19 | 3-[(1-ethyl-1H-pyrazol-4-yl)methyl]-1-[4-{[(1-fluorocyclobutyl)methyl ](methyl)amino}-6-(trifluoromethyl)pyrimidin-2-yl]pyridin-2(1H)-one | 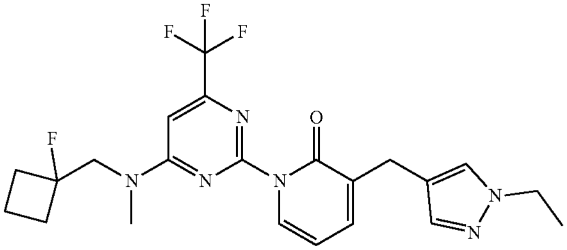 [SMILES: CCn1cc(Cc2cccn(-c3nc(N(C)CC4(F)CCC4)cc(C(F)(F)F)n3)c2=O)cn1] | | 465.1 |
| 20 | 1-{3-cyclopropyl-2-fluoro-5-[(2R)-2-methylmorpholin-4-yl]phenyl}-3-[(1-ethyl-1H-pyrazol-4-yl)methyl]pyridin-2(1H)-one | 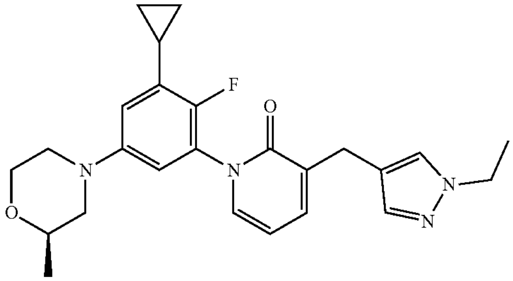 [SMILES: CCn1cc(Cc2cccn(-c3cc(N4CCO[C@H](C)C4)cc(C4CC4)c3F)c2=O)cn1] | | 437.3 |
| 21 | 1-[3-cyclopropyl-5-(2,2-dimethylmorpholin-4-yl)-2-fluorophenyl]-3-[(1-ethyl-1H-pyrazol-4-yl)methyl]pyridin-2(1H)-one | 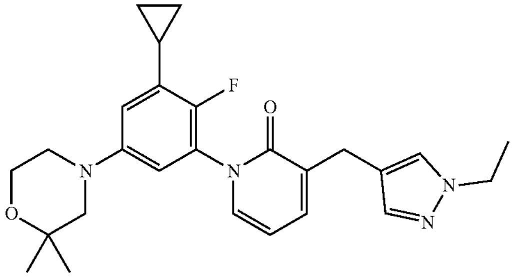 [SMILES: CCn1cc(Cc2cccn(-c3cc(N4CCOC(C)(C)C4)cc(C4CC4)c3F)c2=O)cn1] | | 451.2 |
| 22 | 1-{3-cyclopropyl-2-fluoro-5-[(oxan-4-yl)oxy]phenyl}-3-[(1-ethyl-1H-pyrazol-4-yl)methyl]pyridin-2(1H)-one | 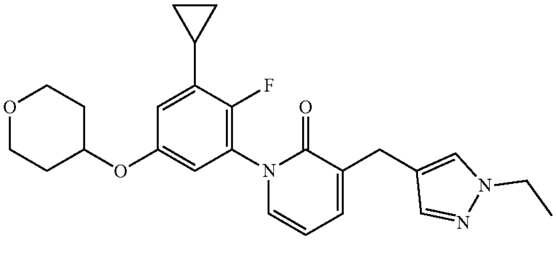 [SMILES: CCn1cc(Cc2cccn(-c3cc(OC4CCOCC4)cc(C4CC4)c3F)c2=O)cn1] | | 438.3 |
| 23 | 1-{3-bromo-2-fluoro-5-[(oxan-4-yl)oxy]phenyl}-3-[(1-ethyl-1H-pyrazol-4-yl)methyl]pyridin-2(1H)-one | 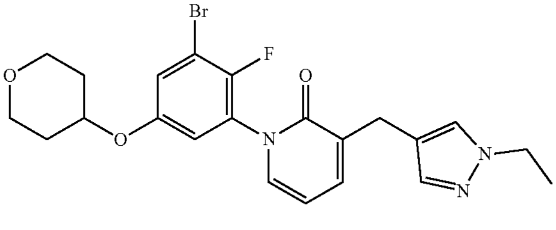 [SMILES: CCn1cc(Cc2cccn(-c3cc(OC4CCOCC4)cc(Br)c3F)c2=O)cn1] | | 476.2 |

TABLE 1-continued

| Example No. | IUPAC Name | Structure | Salt | MS |
|---|---|---|---|---|
| 24 | 3-[(1-ethyl-1H-pyrazol-4-yl)methyl]-1-{2-fluoro-5-[(2R)-2-methylmorpholin-4-yl]-3-(trifluoromethoxy)phenyl} pyridin-2(1H)-one | 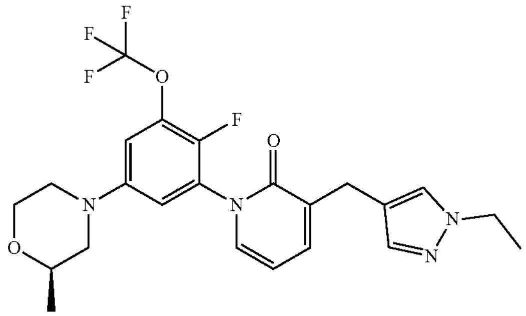 [SMILES: CCn1cc(Cc2cccn(-c3cc(N4CCO[C@H](C)C4)cc(OC(F)(F)F)c3F)c2=O)cn1] | | 481.3 |
| 25 | 1-{3-cyclopropyl-2-fluoro-5-[(2R)-2-methylmorpholin-4-yl]phenyl}-3-{[1-(propan-2-yl)-1H-pyrazol-4-yl]methyl}pyridin-2(1H)-one | 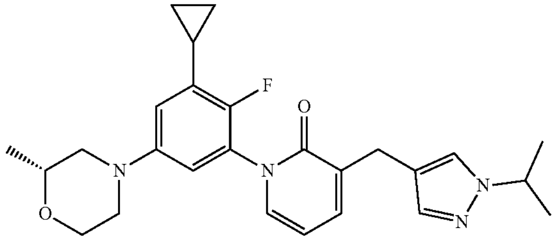 [SMILES: CC(C)n1cc(Cc2cccn(-c3cc(N4CCO[C@H](C)C4)cc(C4CC4)c3F)c2=O)cn1] | | 451.3 |
| 26 | 1-{3-cyclopropyl-2-fluoro-5-[(2R)-2-methylmorpholin-4-yl]phenyl}-3-[(1-ethyl-1H-pyrazol-4-yl)methyl]-4-fluoropyridin-2(1H)-one | 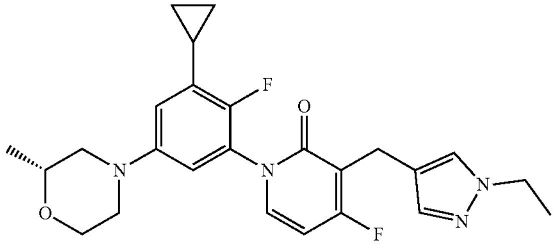 [SMILES: CCn1cc(Cc2c(F)ccn(-c3cc(N4CCO[C@H](C)C4)cc(C4CC4)c3F)c2=O)cn1] | | 455.2 |
| 27 | 3-[(1-ethyl-1H-pyrazol-4-yl)methyl]-1-{2-fluoro-5-[(2R)-2-methylmorpholin-4-yl]-3-(propan-2-yl)phenyl}pyridin-2(1H)-one | 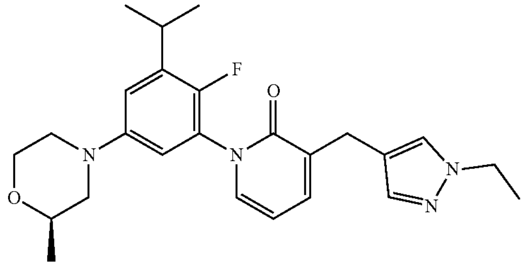 [SMILES: CCn1cc(Cc2cccn(-c3cc(N4CCO[C@H](C)C4)cc(C(C)C)c3F)c2=O)cn1] | | 439.3 |
| 28 | 3-[(1-ethyl-1H-pyrazol-4-yl)methyl]-1-{2-fluoro-5-[(2R)-2-methylmorpholin-4-yl]-3-(2,2,2-trifluoroethyl)phenyl}pyridin-2(1H)-one | 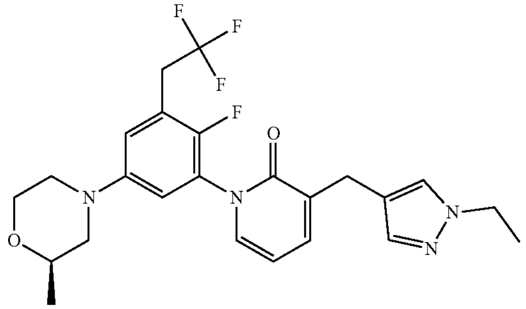 [SMILES: CCn1cc(Cc2cccn(-c3cc(N4CCO[C@H](C)C4)cc(CC(F)(F)F)c3F)c2=O)cn1] | | 479.3 |

TABLE 1-continued

| Example No. | IUPAC Name | Structure | Salt | MS |
|---|---|---|---|---|
| 29 | 1-{3-cyclopropyl-5-[(2R)-2-methylmorpholin-4-yl]phenyl}-3-[(1-ethyl-1H-pyrazol-4-yl)methyl]-6-methylpyridin-2(1H)-one | 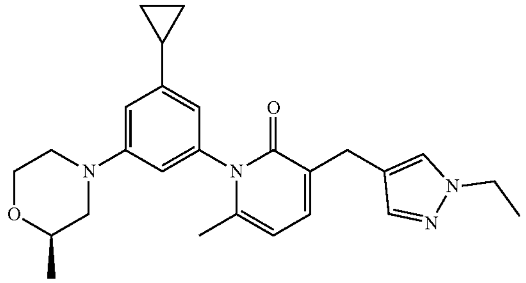 [SMILES: CCn1cc(Cc2ccc(C)n(-c3cc(C4CC4)cc(N4CCO[C@H](C)C4)c3)c2=O)cn1] | | 433.3 |
| 30 | 1-[3-(2,2-difluorocyclopropyl)-5-(4,4-difluoropiperidin-1-yl)-2-fluorophenyl]-3-[(1-ethyl-1H-pyrazol-4-yl)methyl]pyridin-2(1H)-one | 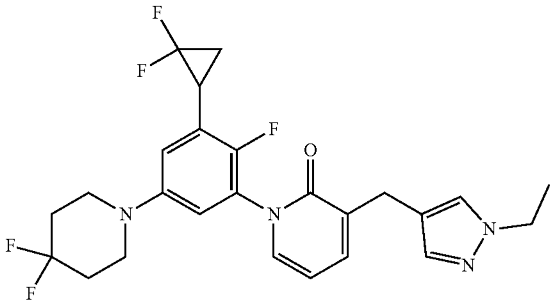 [SMILES: CCn1cc(Cc2cccn(-c3cc(N4CCC(F)(F)CC4)cc(C4CC4(F)F)c3F)c2=O)cn1] | | 492.5 |
| 31 | 1-{3-cyclopropyl-5-[(2R)-2-methylmorpholin-4-yl]phenyl}-3-[(1-ethyl-1H-pyrazol-4-yl)methyl]-6-fluoropyridin-2(1H)-one | 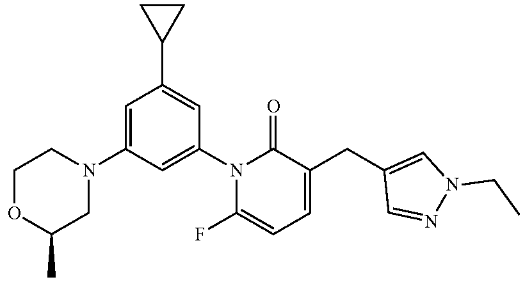 | | 436.5 |
| 32 | 1-{3-cyclopropyl-2-fluoro-5-[(2R)-2-methylmorpholin-4-yl]phenyl}-3-[(1-ethyl-1H-pyrazol-4-yl)methyl]-5-methylpyridin-2(1H)-one | 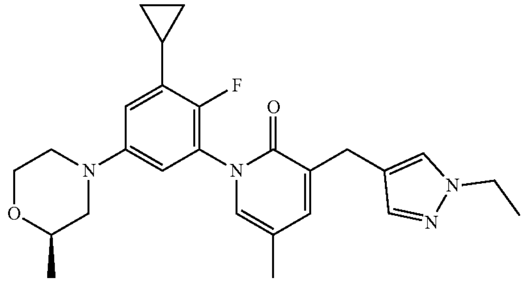 [SMILES: CCn1cc(Cc2cc(C)cn(-c3cc(N4CCO[C@H](C)C4)cc(C4CC4)c3F)c2=O)cn1] | | 451.3 |
| 33 | 1-{3-cyclopropyl-2-fluoro-5-[(2R)-2-methylmorpholin-4-yl]phenyl}-3-[(1-ethyl-1H-pyrazol-4-yl)methyl]-4-methylpyridin-2(1H)-one | 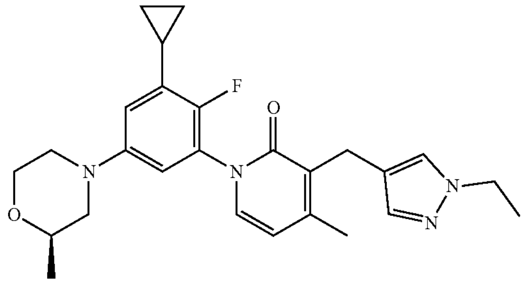 [SMILES: CCn1cc(Cc2c(C)ccn(-c3cc(N4CCO[C@H](C)C4)cc(C4CC4)c3F)c2=O)cn1] | | 451.3 |

Reference Example 1

1-[(1-Ethyl-1H-pyrazole-4-yl)methyl]-3-{2 fluoro-S-[(2R)-2-methylmorpholine-4-yl]-3-(trifluoromethyl)phenyl}-1,3-dihydro-2H-imidazole-2-one

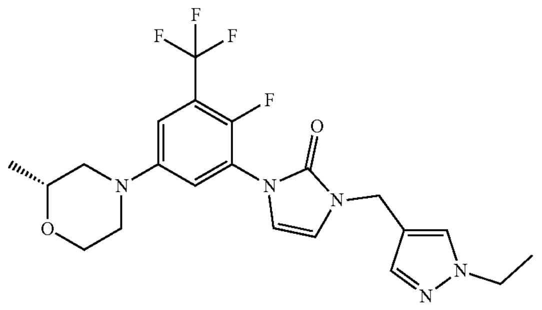 [SMILES: CCn1cc(Cn2ccn(-c3cc(N4CCO[C@H](C)C4)cc(C(F)(F)F)c3F)c2=O)cn1]

A) (2R)-4-[4-Fluoro-3-nitro-5-(trifluoromethyl)phenyl]-2-methylmopholine

A mixture of 5-bromo-2-fluoro-1-nitro-3-(trifluoromethyl)benzene (5.00 g), (2R)-2-methylmorpholine hydrochloride (2.39 g), BINAP (1.08 g), palladium(II) acetate (0.390 g), cesium carbonate (17.0 g), and toluene (40 mL) was stirred for 16 hours at 100° C. in a nitrogen atmosphere. The insoluble matter was filtered out with Celite®, and the filtrate was distilled out under reduced pressure. The residue was purified by silica gel column chromatography (NH, ethyl acetate/hexane) to obtain the title compound (1.85 g).

MS: $[M+H]^+$ 309.2.

B) 2-Fluoro-5-[(2R)-2-methylmorpholine-4-yl]-3-(trifluoromethyl)aniline

A mixture of (2R)-4-[4-fluoro-3-nitro-5-(trifluoromethyl)phenyl]-2-methylmorpholine (1.85 g), 10% palladium-carbon (0.319 g), and EtOH (60 mL) was stirred for two hours at room temperature in a hydrogen atmosphere at normal pressure. The catalyst was filtered out, and the filtrate was concentrated under reduced pressure. The residue was purified by silica gel column chromatography (NH, ethyl acetate/hexane) to obtain the title compound (1.67 g).

MS: $[M+H]^+$ 279.2.

C) N-(2,2-Dimethoxyethyl)-N'-{2-fluoro-5-[(2R)-2-methylmorpholine-4-yl]-3-(trifluoromethyl)phenyl}urea Bis(trichloromethyl) carbonate (0.571 g) was added to a mixture of 2-fluoro-5-[(2R)-2-methylmorpholine-4-yl]-3-(trifluoromethyl)aniline (1.07 g) and THF (30 mL) at 0° C., and the mixture was stirred for four hours at room temperature. Next, 2,2-dimethoxyethaneamine (0.404 g) and TEA (0.389 g) were added to the mixture and stirred overnight at room temperature. Water was added to the mixture, which was then extracted with ethyl acetate. After the organic layer was separated and washed with water and a saturated saline solution, it was dried with anhydrous sodium sulfate and concentrated under reduced pressure. The residue was purified by silica gel column chromatography (NH, ethyl acetate/hexane) to obtain the title compound (1.25 8).

MS: $[M+H]^+$ 410.1.

D) 1-{2-Fluoro-5-[(2R)-2-methylmorpholine-4-yl]-3-(trifluoromethyl)phenyl}-1,3-dihydro-2H-imidazole-2-one TFA (15.4 g) was added to a mixture of N-(2,2-dimethoxyethyl)-N'-{2-fluoro-5-[(2R)-2-methylmorpholine-4-yl]-3-(trifluoromethyl)phenyl}urea (1.25 g), $CH_3CN$ (20 mL), and water (mL). After the mixture was stirred for three hours at 60° C., the reaction mixture was concentrated. The residue was purified by silica gel column chromatography (ethyl acetate/hexane) to obtain the title compound (722 mg).

MS: $[M+H]^+$ 346.2.

E) Ethyl 1-ethyl-1H-pyrazole-4-carboxylate

A mixture of potassium carbonate (197 g), ethyl 1H-pyrazole-4-carboxylate (100 g), ethyl iodide (122 g), and DMF (250 mL) was stirred overnight at room temperature. The mixture was added to water at room temperature and extracted with ethyl acetate. After the organic layer was separated and washed with water and a saturated saline solution, it was dried with anhydrous magnesium sulfate and concentrated under reduced pressure to obtain the title compound (121 g).

$^1H$ NMR (300 MHz, DMSO-$d_6$) δ 1.26 (3H, t, J=7.2 Hz), 1.37 (3H, t, J=7.2 Hz), 4.19 (4H, m), 7.84 (1H, s), 8.33 (1H, s).

F) (1-Ethyl-1H-pyrazole-4-yl)methanol

A mixture of ethyl 1-ethyl-1H-pyrazole-4-carboxylate (48.0 g) and THF (100 mL) was added to a mixture of lithium aluminum hydride (16.3 g) and THF (400 mL) at 0-10° C., and the mixture was stirred for four hours at room temperature. After the mixture was diluted with THF (150 mL) and cooled to 0° C., sodium sulfate decahydrate (110 g) was added at 0-10° C. and stirred for one hour at room temperature. The impurities were filtered out, and the filtrate was distilled out under reduced pressure to obtain the title compound (29.9 g).

$^1H$ NMR (300 MHz, DMSO-$d_6$) δ 1.33 (3H, t, J=7.3 Hz), 4.07 (2H, q, J=7.2 Hz), 4.32 (2H, d, J=5.3 Hz), 4.77 (1H, t, J=5.5 Hz), 7.32 (1H, s), 7.59 (1H, s).

G) 4-(Chloromethyl)-1-ethyl-1H-pyrazole hydrochloride

Thionyl chloride (4.39 g) was added to a mixture of (1-ethyl-1H-pyrazole-4-yl)methanol (2.33 g) and $CH_3CN$ (20 mL) at room temperature, and the mixture was stirred overnight at the same temperature. The mixture was concentrated to obtain the title compound (3.23 g).

$^1H$ NMR (300 MHz, DMSO-$d_6$) δ 1.34 (3H, t, J=7.2 Hz), 4.10 (2H, q, J=7.4 Hz), 4.69 (2H, s), 7.50 (1H, s), 7.85 (1H, s), 12.32 (1H, bs).

H) 1-[(1-Ethyl-1H-pyrazole-4-yl)methyl]-3-{2-fluoro-5-[(2R)-2-methylmorpholine-4-yl]-3-(trifluoromethyl)phenyl}-1,3-dihydro-2H-imidazole-2-one First, 1-{2-fluoro-5-[(2R)-2-methylmorpholine-4-yl]-3-(trifluoromethyl)phenyl}-1,3-dihydro-2H-imidazole-2-one (100 mg) was added to a mixture of sodium hydride (60% content, 29.0 mg) and DMF (3 mL) at room temperature.

After the mixture was stirred for 30 minutes at room temperature, a mixture of 4-(chloromethyl)-1-ethyl-1H-pyrazole hydrochloride (79 mg) and DMF (2 mL) and sodium iodide (43.4 mg) were added and stirred overnight at room temperature. Water was added to the mixture and extracted with ethyl acetate. After the organic layer was separated and washed with water and a saturated saline solution, it was dried with anhydrous sodium sulfate and concentrated under reduced pressure. The residue was purified by silica gel column chromatography (NH, ethyl acetate/hexane) to obtain the title compound (70.0 mg).

$^1$H NMR (300 MHz, DMSO-$d_6$) δ 1.14 (3H, d, J=6.0 Hz), 1.34 (3H, t, J=7.2 Hz), 2.27-2.47 (1H, m), 2.63-2.74 (OH, m), 3.52-3.73 (4H, m), 3.86-3.95 (1H, m), 4.09 (2H, q, J=7.3 Hz), 4.61 (2H, s), 6.74-6.79 (2H, m), 7.19 (1H, dd, J=4.9, 3.4 Hz), 7.34 (1H, dd, J=6.0, 3.0 Hz), 7.43 (1H, s), 7.73 (1H, s).

Test Example 1

Measurement of the inhibition rate of the amount of $IP_1$ in 30 M of the compound of Reference Example 1 in GPR139-expressed CHO cells Changes in the amount of $IP_1$ in GPR139-expressed CHO cells were measured in order to evaluate the activity of the compound via GPR139. GPR139 is a Gq-coupled receptor which varies intracellular calcium (Liu C et al., Mol Pharmacol. 2015 November; 88(5):911-25), so the amount of $IP_1$, which is a stable metabolite of the second messenger $IP_3$, changes due to activity regulation of GPR139. GPR139 is considered to be structurally active when expressed recombinantly in mammal cells, so a compound having a GPR139 receptor inverse agonist action is expected to reduce the amount of $IP_1$ production.

The measurement of $IP_1$ was made using an IP-ONE HTFR assay kit (cis-bio) and CHO-TREx (Life Technologies) cells stably transfected with GPR139. The CHO-TREx cells expressed human GPR139 with a tetracycline-inducing element. The cells were cultured in a medium containing F12K and 10% tetracycline-free FBS, and the expression of human GPR139 was induced over the course of 17 hours under conditions of 37° C. and 5% $CO_2$ in the presence of 2 μg/mL of doxycycline (Clontech, 631311) in the growth medium on the day before assay. On the day of the test, after the cells were washed with 10 mL of PBS, the cells were detached with TrypLE Express (Life Technologies) and centrifuged at 1,000 rpm to form pellets, and a cell suspension was then prepared using a stimulation buffer (cis-bio, included in the IP-ONE HTRF assay kit).

The compound was diluted with the stimulation buffer, and 4 μL was added to a 384-well white assay plate (Greiner). The cell suspension was added so that there were 2000 cells per well, and the assay plate was left to stand for 40 minutes at 37° C. Equal amounts of iP1-d2 and Ab-Crp solutions (both available from cis-bio, included in the IP-ONE HTRF assay kit) prepared with a lysis buffer (cis-bio, included in the IP-ONE HTRF assay kit) were mixed, and 4 μL was added to the assay plate and left to stand for one hour at room temperature. After the fluorescence strengths of two wavelengths were measured by the HTRF settings of Envision (PerkinElmer), the value of Ratio=((Signal 665 nm)/(Signal 615 nm))×10000 was calculated. When the vehicle was set to 0% and the value at which the $IP_1$ concentration is 0 was set to 100%, the inhibition rate of the amount of $IP_1$ in 30 μM of the compound of Reference Example 1 was 84%.

The compound of Reference Example 1 inhibited the amount of $IP_1$, which is a stable metabolite of the second messenger IP3 in the downstream of signal transmission in GPR139, in GPR139-expressed CHO cells. That is, the compound of Reference Example 1 exhibits GPR139 receptor inverse agonist action.

Test Example 2

Measurement of the Inhibition Rate of the Amount of $IP_1$ in GPR139-Expressed CHO Cells (Inverse Agonist Assay)

The activities of the compounds of Examples 20 to 33 were expressed as relative values in Table 2 by measuring the inhibition rate of the amount of $IP_1$ with the same method as in Test Example 1 and defining the inhibition rate of the amount of $IP_1$ of the compound of Reference Example 1 in Test Example 1 as 100%.

TABLE 2

| Example No. | $IP_1$ Inhibition Rate at 30 μM |
|---|---|
| 20 | 96% |
| 21 | 96% |
| 22 | 98% |
| 23 | 100% |
| 24 | 98% |
| 25 | 95% |
| 26 | 97% |
| 27 | 96% |
| 28 | 100% |
| 29 | 102% |
| 30 | 97% |
| 31 | 100% |
| 32 | 99% |
| 33 | 96% |

As shown in Table 2, the compound of the present disclosure inhibited the amount of $IP_1$, which is a stable metabolite of the second messenger IP3 in the downstream of signal transmission in GPR139, in GPR139-expressed CHO cells. That is, the compound of the present disclosure has a GPR139 receptor antagonist action (inverse agonist action).

Formulation Examples

In some embodiments, pharmaceuticals comprising a compound of the present disclosure as an active ingredient can be produced using the following non-limiting example formulations.

TABLE 3

| | |
|---|---|
| (1) Compound obtained in Example 1 | 10 mg |
| (2) Lactose | 90 mg |
| (3) Microcrystalline cellulose | 70 mg |
| (4) Magnesium stearate | 10 mg |
| One capsule | 180 mg |

After the total amounts of (1), (2), and (3) and 5 mg of (4) are mixed and granulated, the remaining 5 mg of (4) is added, and the entire substance mixture is sealed in a gelatin capsule.

TABLE 4

| | |
|---|---|
| (1) Compound obtained in Example 1 | 10 mg |
| (2) Lactose | 35 mg |
| (3) Corn starch | 150 mg |

TABLE 4-continued

| | |
|---|---|
| (4) Microcrystalline cellulose | 30 mg |
| (5) Magnesium stearate | 5 mg |
| One tablet | 230 mg |

After the total amounts of (1), (2), and (3), 20 mg of (4), and 2.5 mg of (5) are mixed and granulated, the remaining 10 mg of (4) and 2.5 mg of (5) are added to the granules and pressure-molded to form a tablet.

What is claimed is:

1. A compound of Formula (I)

(I)

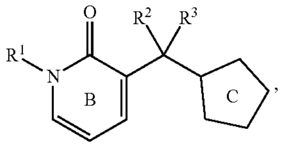

or a pharmaceutically acceptable salt thereof, wherein:

$R^1$ is

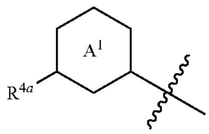

or

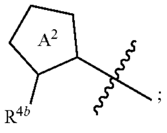

;

ring $A^1$ is chosen from 6-membered aromatic rings optionally further substituted with 1 to 3 substituents chosen from:

(a) halogen atoms;

(b) cyano groups;

(c) optionally halogenated $C_{1-6}$ alkyl groups;

(d) optionally halogenated $C_{1-6}$ alkoxy groups; and (e) $C_{3-10}$ cycloalkyl groups optionally substituted with 1 to 3 halogen atoms;

ring $A^2$ is chosen from 5-membered monocyclic aromatic heterocyclic rings optionally further substituted with 1 to 3 substituents chosen from:

(a) halogen atoms;

(b) cyano groups;

(c) optionally halogenated $C_{1-6}$ alkyl groups;

(d) optionally halogenated $C_{1-6}$ alkoxy groups; and (e) $C_{3-10}$ cycloalkyl groups;

ring B is chosen from pyridone rings optionally further substituted with 1 to 3 substituents chosen from halogen atoms and $C_{1-6}$ alkyl groups;

$R^2$ and $R^3$ are each independently chosen from a hydrogen atom and $C_{1-6}$ alkyl groups;

$R^{4a}$ and $R^{4b}$ are each independently chosen from substituents:

(1) $C_{6-14}$ aryl groups optionally substituted with 1 to 3 halogen atoms;

(2) 3- to 14-membered non-aromatic heterocyclic groups optionally substituted with 1 to 3 substituents chosen from:

(a) halogen atoms; and (b) optionally halogenated $C_{1-6}$ alkyl groups;

(3) mono- or di-$C_{1-6}$ alkylamino groups optionally substituted with 1 to 3 $C_{3-10}$ cycloalkyl groups optionally substituted with 1 to 3 halogen atoms; and (4) 3- to 14-membered non-aromatic heterocyclic oxy groups; and ring C is chosen from 5-membered monocyclic aromatic heterocyclic rings optionally further substituted with 1 to 3 substituents independently chosen from $C_{1-6}$ alkyl groups.

2. The compound or pharmaceutically acceptable salt according to claim 1, wherein the compound is chosen from compounds of Formula (I')

(I')

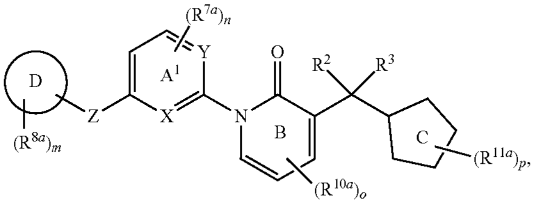

and pharmaceutically acceptable salts thereof, wherein:

X is CH or N;

Y is CH or N;

Z is chosen from a bond, —O—, —$OR^{9a}$—*, —NH—, and —$N(R^{9b})R^{9a}$—*, wherein * denotes the connection point to ring D;

ring C is chosen from 5-membered monocyclic aromatic heterocyclic rings;

ring D is chosen from 6- to 8-membered aromatic rings, 5- to 8-membered monocyclic aromatic heterocyclic rings, $C_{3-8}$ cycloalkyl groups, and 5- to 8-membered heterocyclic groups;

$R^2$ and $R^3$ are each independently chosen from a hydrogen atom and $C_{1-6}$ alkyl groups;

each $R^{7a}$ is independently chosen from cyano, halogen, $C_{3-6}$ cycloalkyl, $C_{1-6}$ alkyl, and $C_{1-6}$ alkoxy groups, wherein the $C_{3-6}$ cycloalkyl, $C_{1-6}$ alkyl, and $C_{1-6}$ alkoxy groups are optionally substituted with 1 to 4 halogen atoms;

each $R^{8a}$ is independently chosen from halogen, $C_{1-6}$ alkyl, and $C_{1-6}$ alkoxy groups, wherein the $C_{1-6}$ alkyl and $C_{1-6}$ alkoxy groups are optionally substituted with 1 to 4 halogen atoms;

$R^{9a}$ is chosen from $C_{1-3}$ alkyl groups;

$R^{9b}$ is chosen from hydrogen atom and $C_{1-3}$ alkyl groups;

each $R^{10a}$ is independently chosen from halogen atoms and $C_{1-3}$ alkyl groups;

each $R^{11a}$ is independently chosen from $C_{1-3}$ alkyl groups;

m is 0, 1, 2, or 3;

n is 0, 1, 2, or 3;

is 0, 1, or 2; and p is 0, 1, or 2.

3. The compound or pharmaceutically acceptable salt according to claim 2, wherein:

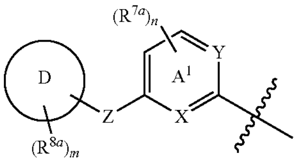

is

-continued

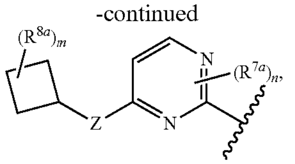

wherein Z, $R^{7a}$, $R^{8a}$, m, and n are as defined in claim 2.

4. The compound or pharmaceutically acceptable salt according to claim 2, wherein Z is a bond.

5. The compound or pharmaceutically acceptable salt according to claim 2, wherein Z is —O—.

6. The compound or pharmaceutically acceptable salt according to claim 2, wherein Z is $—NHCH_2—*$.

7. The compound or pharmaceutically acceptable salt according to claim 2, wherein Z is $—N(CH_3)CH_2—*$.

8. The compound or pharmaceutically acceptable salt according to claim 2, wherein ring D is chosen from benzene, morpholine, oxane, piperidine, and cyclobutane.

9. The compound or pharmaceutically acceptable salt according to claim 2, wherein

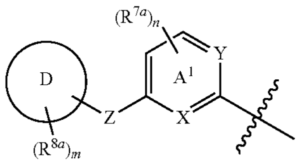

is

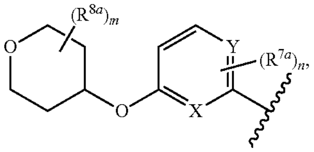

and wherein X, Y, $R^{7a}$, $R^{8a}$, m, and n are as defined in claim 2.

10. The compound or pharmaceutically acceptable salt according to claim 2, wherein X is CH.

11. The compound or pharmaceutically acceptable salt according to claim 2, wherein X is N.

12. The compound or pharmaceutically acceptable salt according to claim 2, wherein Y is CH.

13. The compound or pharmaceutically acceptable salt according to claim 2, wherein Y is N.

14. The compound or pharmaceutically acceptable salt according to claim 2, wherein

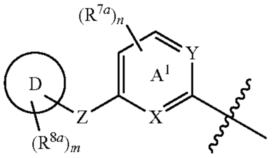

is

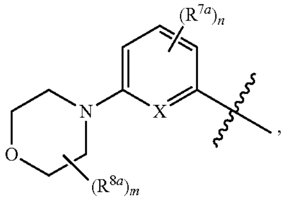

and wherein X, $R^{7a}$, $R^{8a}$, m, and n are as defined in claim 2.

15. The compound or pharmaceutically acceptable salt according to claim 2, wherein

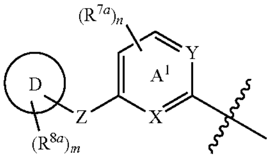

is

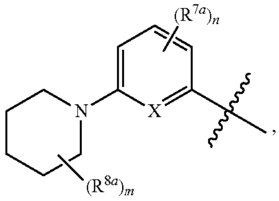

and wherein X, $R^{7a}$, $R^{8a}$, m, and n are as defined in claim 2.

16. The compound or pharmaceutically acceptable salt according to claim 2, wherein $R^2$ and $R^3$ are both hydrogen atoms.

17. The compound or pharmaceutically acceptable salt according to claim 2, wherein ring C is

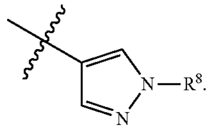

18. The compound or pharmaceutically acceptable salt according to claim 2, wherein o is 1 and $R^{10a}$ is methyl or a fluorine atom.

19. The compound or pharmaceutically acceptable salt according to claim 2, wherein o is 0.

20. A compound chosen from:

3-[(1-ethyl-1H-pyrazol-4-yl)methyl]-6'-(4-fluorophenyl)-4'-(trifluoromethyl)-2H-[1,2'-bipyridin]-2-one;

3-[(1-ethyl-1H-pyrazol-4-yl)methyl]-6'-(4-fluorophenyl)-2-oxo-4'-(trifluoromethyl)-2H-[1,2'-bipyridine]-3'-carbonitrile;

3-[(1-ethyl-1H-pyrazol-4-yl)methyl]-6'-(4-fluorophenyl)-2-oxo-4'-(2,2,2-trifluoroethoxy)-2H-[1,2'-bipyridine]-3'-carbonitrile;

4'-(2,2-difluoroethoxy)-3-[(1-ethyl-1H-pyrazol-4-yl)methyl]-6'-(4-fluorophenyl)-2-oxo-2H-[1,2'-bipyridine]-3'-carbonitrile;

3-[(1-ethyl-1H-pyrazol-4-yl)methyl]-6'-(4-fluorophenyl)-6-methyl-2-oxo-4'-(trifluoromethyl)-2H-[1,2'-bipyridine]-3'-carbonitrile;

4'-(difluoromethyl)-3-[(1-ethyl-1H-pyrazol-4-yl)methyl]-6'-(4-fluorophenyl)-2-oxo-2H-[1,2'-bipyridine]-3'-carbonitrile;

3-[(1-ethyl-1H-pyrazol-4-yl)methyl]-3'-fluoro-6'-[(2R)-2-methylmorpholin-4-yl]-4'-(trifluoromethyl)-2H-[1,2'-bipyridin]-2-one;

3-[(1-ethyl-1H-pyrazol-4-yl)methyl]-5'-methyl-6'-[(2R)-2-methylmorpholin-4-yl]-4'-(trifluoromethyl)-2H-[1,2'-bipyridin]-2-one;

3-[(1-ethyl-1H-pyrazol-4-yl)methyl]-1-{2-fluoro-5-[(2R)-2-methylmorpholin-4-yl]-3-(trifluoromethyl)phenyl}pyridin-2 (1H)-one;

6'-[2-(difluoromethyl) morpholin-4-yl]-3-[(1-ethyl-1H-pyrazol-4-yl)methyl]-3'-fluoro-4'-(trifluoromethyl)-2H-[1,2'-bipyridin]-2-one;

3-[(1-ethyl-1H-pyrazol-4-yl)methyl]-3'-fluoro-4-methyl-6'-[(2R)-2-methylmorpholin-4-yl]-4'-(trifluoromethyl)-2H-[1,2'-bipyridin]-2-one;

3-[(1-ethyl-1H-pyrazol-4-yl)methyl]-3'-fluoro-5-methyl-6'-[(2R)-2-methylmorpholin-4-yl]-4'-(trifluoromethyl)-2H-[1,2'-bipyridin]-2-one;

3-[(1-ethyl-1H-pyrazol-4-yl)methyl]-3'-fluoro-6'-[(oxan-4-yl)oxy]-4'-(trifluoromethyl)-2H-[1,2'-bipyridin]-2-one;

3-[(1-ethyl-1H-pyrazol-4-yl)methyl]-1-[4-{[(1-fluorocyclobutyl)methyl]amino}-6-(trifluoromethyl)pyrimidin-2-yl]pyridin-2 (1H)-one;

1-[4-{[(3,3-difluorocyclobutyl)methyl]amino}-6-(trifluoromethyl)pyrimidin-2-yl]-3-[(1-ethyl-1H-pyrazol-4-yl)methyl]pyridin-2 (1H)-one;

1-[4-{[(3,3-difluorocyclobutyl)methyl](methyl)amino}-6-(trifluoromethyl)pyrimidin-2-yl]-3-[(1-ethyl-1H-pyrazol-4-yl)methyl]pyridin-2 (1H)-one;

3-[(1-ethyl-1H-pyrazol-4-yl)methyl]-1-[4 {[(1-fluorocyclobutyl)methyl](methyl)amino}-6-(trifluoromethyl)pyrimidin-2-yl]pyridin-2 (1H)-one;

1-{3-cyclopropyl-2-fluoro-5-[(2R)-2-methylmorpholin-4-yl]phenyl}-3-[(1-ethyl-1H-pyrazol-4-yl)methyl]pyridin-2 (1H)-one;

1-[3-cyclopropyl-5-(2,2-dimethylmorpholin-4-yl)-2-fluorophenyl]-3-[(1-ethyl-1H-pyrazol-4-yl)methyl]pyridin-2 (1H)-one;

1-{3-cyclopropyl-2-fluoro-5-[(oxan-4-yl)oxy]phenyl}-3-[(1-ethyl-1H-pyrazol-4-yl)methyl]pyridin-2 (1H)-one;

1-{3-bromo-2-fluoro-5-[(oxan-4-yl)oxy]phenyl}-3-[(1-ethyl-1H-pyrazol-4-yl)methyl]pyridin-2 (1H)-one;

3-[(1-ethyl-1H-pyrazol-4-yl)methyl]-1-{2-fluoro-5-[(2R)-2-methylmorpholin-4-yl]-3-(trifluoromethoxy)phenyl}pyridin-2 (1H)-one;

1-{3-cyclopropyl-2-fluoro-5-[(2R)-2-methylmorpholin-4-yl]phenyl}-3-{[1-(propan-2-yl)-1H-pyrazol-4-yl]methyl}pyridin-2 (1H)-one;

1-{3-cyclopropyl-2-fluoro-5-[(2R)-2-methylmorpholin-4-yl]phenyl}-3-[(1-ethyl-1H-pyrazol-4-yl)methyl]-4-fluoropyridin-2 (1H)-one;

3-[(1-ethyl-1H-pyrazol-4-yl)methyl]-1-{2-fluoro-5-[(2R)-2-methylmorpholin-4-yl]-3-(propan-2-yl)phenyl}pyridin-2 (1H)-one;

3-[(1-ethyl-1H-pyrazol-4-yl)methyl]-1-{2-fluoro-5-[(2R)-2-methylmorpholin-4-yl]-3-(2,2,2-trifluoroethyl)phenyl}pyridin-2 (1H)-one;

1-{3-cyclopropyl-5-[(2R)-2-methylmorpholin-4-yl]phenyl}-3-[(1-ethyl-1H-pyrazol-4-yl)methyl]-6-methylpyridin-2 (1H)-one;

1-[3-(2,2-difluorocyclopropyl)-5-(4,4-difluoropiperidin-1-yl)-2-fluorophenyl]-3-[(1-ethyl-1H-pyrazol-4-yl)methyl]pyridin-2 (1H)-one;

1-{3-cyclopropyl-5-[(2R)-2-methylmorpholin-4-yl]phenyl}-3-[(1-ethyl-1H-pyrazol-4-yl)methyl]-6-fluoropyridin-2 (1H)-one;

1-{3-cyclopropyl-2-fluoro-5-[(2R)-2-methylmorpholin-4-yl]phenyl}-3-[(1-ethyl-1H-pyrazol-4-yl)methyl]-5-methylpyridin-2 (1H)-one; and 1-{3-cyclopropyl-2-fluoro-5-[(2R)-2-methylmorpholin-4-yl]phenyl}-3-[(1-ethyl-1H-pyrazol-4-yl)methyl]-4-methylpyridin-2 (1H)-one, or a pharmaceutically acceptable salt of any of the foregoing.

21. A pharmaceutical composition comprising:

at least one compound or pharmaceutically acceptable salt according to claim 1; and at least one pharmaceutically acceptable carrier.

22. A method of treating or preventing a disease in a mammal in need thereof, the method comprising administering to the mammal at least one compound or pharmaceutically acceptable salt according to claim 1.

23. The method according to claim 22, wherein the disease is chosen from depression, Alzheimer's disease, schizophrenia, drug addiction, sleep disorders, pain, and attention deficit hyperactivity disorder.

24. The method according to claim 22, wherein the mammal is a human.

25. The method according to claim 22, further comprising administering to the mammal at least one combination drug.

26. A pharmaceutical composition comprising:

at least one compound or pharmaceutically acceptable salt according to claim 2; and at least one pharmaceutically acceptable carrier.

27. A method of treating or preventing a disease in a mammal in need thereof, the method comprising administering to the mammal at least one compound or pharmaceutically acceptable salt according to claim 2.

* * * * *